United States Patent
Kol et al.

(10) Patent No.: US 9,193,813 B2
(45) Date of Patent: Nov. 24, 2015

(54) PHENYLENE-BRIDGED SALALEN CATALYSTS

(71) Applicants: ExxonMobil Chemical Patents Inc., Baytown, TX (US); Ramot at Tel-Aviv University Ltd., Tel Aviv (IL)

(72) Inventors: Moshe Kol, Ramat Gan (IL); Matthew W. Holtcamp, Huffman, TX (US); Konstantin Press, Rishon LeZion (IL); Ayellet Stopper, Yarkona (IL)

(73) Assignees: ExxonMobil Chemical Patents Inc., Baytown, TX (US); Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 14/565,307

(22) Filed: Dec. 9, 2014

(65) Prior Publication Data
US 2015/0274858 A1 Oct. 1, 2015

Related U.S. Application Data

(60) Provisional application No. 61/972,860, filed on Mar. 31, 2014.

(51) Int. Cl.
| | | |
|---|---|---|
| *C08F 110/06* | (2006.01) | |
| *C07F 7/28* | (2006.01) | |
| *C07F 7/00* | (2006.01) | |
| *C08F 4/64* | (2006.01) | |
| *C08F 4/60* | (2006.01) | |

(52) U.S. Cl.
CPC .................. *C08F 110/06* (2013.01); *C07F 7/00* (2013.01); *C07F 7/28* (2013.01); *C08F 4/60189* (2013.01); *C08F 4/64189* (2013.01)

(58) Field of Classification Search
CPC ..... C08F 4/60189; C08F 4/64189; C07F 7/00
See application file for complete search history.

(56) References Cited

U.S. PATENT DOCUMENTS

| | | | |
|---|---|---|---|
| 4,066,715 | A | 1/1978 | Isa et al. |
| 5,153,157 | A | 10/1992 | Hlatky et al. |
| 5,942,459 | A | 8/1999 | Sugano et al. |
| 5,998,645 | A | 12/1999 | Nestler |
| 6,309,997 | B1 | 10/2001 | Fujita et al. |
| 6,399,724 | B1 | 6/2002 | Matsui et al. |
| 6,462,136 | B1 | 10/2002 | Saito et al. |
| 6,531,555 | B2 | 3/2003 | Whiteker |

(Continued)

FOREIGN PATENT DOCUMENTS

| | | |
|---|---|---|
| CN | 101080399 | 11/2007 |
| CN | 101437827 | 5/2009 |

(Continued)

OTHER PUBLICATIONS

PCT/IL2011/000482 International Search Report and Written Opinion, Jan. 13, 2013.

(Continued)

*Primary Examiner* — Rip A Lee
(74) *Attorney, Agent, or Firm* — Daniel N. Lundeen; Lundeen & Lundeen PLLC

(57) ABSTRACT

A phenylene-bridged Salalen catalyst, a catalyst system comprising an activator and the phenylene-bridged Salalen catalyst, a process comprising contacting one or more olefins with the catalyst system, and polymers produced by the process are disclosed herein.

28 Claims, 2 Drawing Sheets

Molecular structure of $Lig^5Hf(OtBu)_2$

(56) References Cited

U.S. PATENT DOCUMENTS

| | | | |
|---|---|---|---|
| 6,548,723 | B2 | 4/2003 | Bagheri et al. |
| 6,632,899 | B2 | 10/2003 | Kol et al. |
| 6,686,490 | B1 | 2/2004 | Kol et al. |
| 6,699,824 | B1 | 3/2004 | Dawson et al. |
| 7,105,703 | B1 | 9/2006 | Atwood |
| 7,144,839 | B2 | 12/2006 | Gibson et al. |
| 7,241,714 | B2 | 7/2007 | Boussie et al. |
| 7,300,903 | B2 | 11/2007 | Fujita et al. |
| 7,385,015 | B2 | 6/2008 | Holtcamp |
| 7,531,602 | B2 | 5/2009 | Hoang et al. |
| 7,544,749 | B2 | 6/2009 | Jones et al. |
| 7,696,123 | B2 | 4/2010 | Schneider et al. |
| 7,812,184 | B2 | 10/2010 | Kondo et al. |
| 7,880,047 | B2 | 2/2011 | Knowles et al. |
| 7,989,565 | B2 | 8/2011 | Gibson et al. |
| 8,058,373 | B2 | 11/2011 | Stevens et al. |
| 8,101,696 | B2 | 1/2012 | Konze et al. |
| 8,202,953 | B2 | 6/2012 | Konze et al. |
| 8,222,358 | B2 | 7/2012 | Rodriguez et al. |
| 8,299,189 | B2 | 10/2012 | Boone et al. |
| 8,450,438 | B2 | 5/2013 | Aboelella et al. |
| 8,907,032 | B2 * | 12/2014 | Kol et al. ............... 526/172 |
| 2002/0173604 | A1 | 11/2002 | Kol et al. |
| 2003/0105250 | A1 | 6/2003 | Whiteker |
| 2004/0167016 | A1 | 8/2004 | Holtcamp et al. |
| 2005/0075242 | A1 | 4/2005 | Holtcamp et al. |
| 2005/0227860 | A1 | 10/2005 | Green et al. |
| 2006/0100092 | A1 | 5/2006 | Jones et al. |
| 2007/0021561 | A1 | 1/2007 | Tse et al. |
| 2007/0208148 | A1 | 9/2007 | Rodriguez et al. |
| 2008/0108499 | A1 | 5/2008 | Coates et al. |
| 2009/0043100 | A1 | 2/2009 | Kondo et al. |
| 2009/0099381 | A1 | 4/2009 | Katsuki et al. |
| 2009/0186995 | A1 | 7/2009 | Canich et al. |
| 2009/0318640 | A1 | 12/2009 | Brant et al. |
| 2009/0318644 | A1 | 12/2009 | Brant et al. |
| 2010/0081808 | A1 | 4/2010 | Kondo et al. |
| 2010/0298510 | A1 | 11/2010 | Crowther et al. |
| 2011/0124831 | A1 | 5/2011 | Luo |
| 2011/0152497 | A1 | 6/2011 | Allen et al. |
| 2011/0306740 | A1 | 12/2011 | Nagy et al. |
| 2011/0319578 | A1 | 12/2011 | Hanaoka et al. |
| 2012/0184676 | A1 | 7/2012 | Gahleitner et al. |
| 2012/0245312 | A1 | 9/2012 | Holtcamp |
| 2012/0316302 | A1 | 12/2012 | Stewart |
| 2013/0030135 | A1 | 1/2013 | Hagadorn et al. |
| 2013/0066029 | A1 | 3/2013 | Radlauer et al. |
| 2013/0096271 | A1 | 4/2013 | Kol et al. |
| 2013/0253244 | A1 | 9/2013 | Emett et al. |
| 2013/0310529 | A1 | 11/2013 | Kol et al. |
| 2014/0039137 | A1 | 2/2014 | Giesbrecht et al. |
| 2014/0039138 | A1 | 2/2014 | Giesbrecht et al. |
| 2014/0039139 | A1 | 2/2014 | Giesbrecht et al. |
| 2014/0039140 | A1 | 2/2014 | Giesbrecht et al. |
| 2014/0039141 | A1 | 2/2014 | Giesbrecht et al. |

FOREIGN PATENT DOCUMENTS

| | | | |
|---|---|---|---|
| EP | 1849775 | | 10/2007 |
| EP | 1849778 | | 10/2007 |
| EP | 2003135 | | 12/2008 |
| EP | 2532687 | | 12/2012 |
| JP | 2007284438 | | 11/2007 |
| WO | 9806727 | | 2/1998 |
| WO | 03091292 | | 11/2003 |
| WO | 2004069881 | | 8/2004 |
| WO | 2007007893 | | 1/2007 |
| WO | 2009027516 | | 3/2009 |
| WO | 2011019474 | | 2/2011 |
| WO | 2011158241 | | 12/2011 |
| WO | WO 2011/158241 | A1 * | 12/2011 ............... C07F 7/00 |
| WO | 2012004680 | | 1/2012 |
| WO | 2012098521 | | 1/2012 |
| WO | 2013043796 | | 3/2013 |

OTHER PUBLICATIONS

Berkessel, Albrecht et al., Ligands: Highly Enantioselective Titanium In Situ Catalysts for Asymmetric Epoxidation with Aqueous Hydrogen Peroxide, Adv. Synth Catal, 2007, vol. 349, pp. 2385-2391.

Whitelaw, Emma L. et al., Group 4 Salalen Complexes and Their Application for the Ring-Opening Polymerization of rac-Lactide, Inorg. Chem., 2010, vol. 49, pp. 7176-7181.

PCT/US2013/69419 International Search Report and Written Opinion, Mar. 7, 2014.

PCT/US2013/46569 International Search Report and Written Opinion, Jun. 13, 2014.

PCT/US2014/041362—ISR and WO, Oct. 1, 2014.

PCT/US2014/039786—ISR and WO, Sep. 29, 2014.

PCT/US2014/39766—ISR and WO, Oct. 31, 2014.

Immel et al., Cytotoxic dinuclear titanium-salan complexes: Structural and biological characterization, Journal of Inorganic Biochemistry, 2012, vol. 106, pp. 68-75.

Busico et al. "Living Ziegler-Natta Polymerization: True or False?", Macromolecules Symposium, 226: 1-16, 2005.

Busico et al. "Reactivity of Secondary Metal-Alkyls in Catalytic Propene Polymerization: How Dormant Are 'Dormant Chains'?", Journal of the American Chemical Society, 127(6): 1608-1609, 2005.

Ciancaleone et al. "Activation of a Bis(Phenoxy-Amine) Precatalyst for Olefin Polymerization: First Evidence for an Outer Sphere Ion Pair With the Methylborate Counterion", Dalton Transactions, p. 8824-8827, 2009.

Ciancaleone et al. "Stucture-Activity Relationship in Olefin Polymerization Catalysis: Is Entropy the Key?", Journal of the American Chemical Society, JACS, 132: 13651-13653, 2010.

Tshuva et al. "Single-Step Synthesis of Salans and Substituted Salans by Mannich Condensation", Tetrahedron Letters, 42: 6405-6407, 2001.

Official Action Dated Sep. 6, 2013 From the US Patent and Trademark Office Re. U.S. Appl. No. 13/805,011.

Restriction Official Action Dated May 13, 2013 From the US Patent and Trademark Office Re. U.S. Appl. No. 13/805,011.

Notice of Allowance Dated Jul. 1, 2014 From the US Patent and Trademark Office Re. U.S. Appl. No. 13/805,011.

Communication Pursuant to Article 94(3) EPC Dated Mar. 14, 2014 From the European Patent Office Re. Application No. 11736169.1.

Communication Relating to the Results of the Partial International Search Dated Apr. 19, 2012 From the International Searching Authority Re. Application No. PCT/IB2012/050267.

Corrected International Search Report and the Written Opinion Dated Sep. 25, 2012 From the International Searching Authority Re. Application No. PCT/IB2012/050267.

International Search Report and the Written Opinion Dated Jun. 19, 2012 From the International Searching Authority Re. Application No. PCT/IB2012/050267.

Office Action Dated Jul. 28, 2014 From The State Intellectual Property Office of the People's Republic of China Re. Application No. 201180039237.5.

Search Report Dated Jul. 28, 2014 From The State Intellectual Property Office of the People's Republic of China Re. Application No. 201180039237.5.

International Preliminary Report and the Written Opinion on Patentability Dated Jan. 3, 2013 From the International Bureau of WIPO Re. Application No. PCT/IL2011/000482.

International Search Report Dated Dec. 5, 2011 From the International Searching Authority Re. Application No. PCT/IL2011/000482.

International Preliminary Report and Written Opinion on Patentability Dated Jul. 23, 2013 From the International Bureau of WIPO Re. Application No. PCT/IB2012/050267.

Office Action Dated Jul. 28, 2014 From The State Intellectual Property Office of the People's Republic of China Re. Application No. 201180039237.5 Translation Into English.

PCT/US2013/046615 International Search Report and Written Opinion, Nov. 13, 2013.

(56) References Cited

OTHER PUBLICATIONS

PCT/US2013/053363 International Search Report and Written Opinion, Dec. 20, 2013.
Sanz et al. "Monocyclopentadienyl Bis(phenoxo-imino) Zirconium Complexes as Precatalyst Species for Olefin Polymerization. Stereospecific Methylation of an Imino Group with Formation of a Zirconium-amido Bond", Organometallics, 23: 5324-5331, 2004.
Allard et al., "Sequential Phenolate Oxidations in Octahedral Cobalt (III) Complexes with [N1O3] Ligands", European Journal of Inorganic Chemistry 2012, 29: 4622-4631.
Rajendiran et al., "Cleavage of Proteins by a Mixed-Ligand Copper (II) Phenolate Complex: Hydrophobicity of the Diimine Coligand Promotes Cleavage", Inorg. Chem., 2007, 46: 10446-10448.
Plass "Synthese, Struktur und Oxotransferreaktionen von Dioxomolybdan (VI)—Komplexen mit mehrzahnigen Aminoalkoholen als Liganden", Z. anorg. allg. Chem., 623 (1997) 997-1005.
PCT/US14/69210, Protest Proceedings, Jan. 16, 2015.
PCT/US14/69210, ISR and WO, Mar. 30, 2015.
Arredondo, Yolanda et al., Non-Catalyzed C-Alkylation of Phenols with Cyclic Secondary Alkyl Bromies, Synthetic Communications, 1996, vol. 26, No. 21, pp. 3885-3895.
Bryliakov, K. et al, Titanium-Salan-Catalyzed Asymmetric Oxidation of Sulfides and Kinetic Resolution of Sulfoxides with H2O2 as the Oxidant, Eur. J. Org. Chem., 2008, pp. 3369-3376.
Busico, Vincenzo et al, New Evidence on the Nature of the Active Sites in Heterogeneous Ziegler-Natta Catalysts for Propene Polymerization, 1997, Macromolecules, vol. 30, pp. 4786-4790.
Busico, Vincenzo et al., Mimicking Ziegler-Natta Catalysts in Homogeneous Phase, 1 C2-Symmetric Octahedral Zr (IV) Complexes with Tetradentate [ONNO]-Type Ligands, Macromol. Rapid Commun. 2001, vol. 22, No. 17, pp. 1405-1409.
Busico, Vincenzo et al., The first Molecularly Characterized Isotactic Polypropylene-block-polyethylene Obtained via "Quasi-Living" Insertion Polymerization, Macromolecules, 2003, vol. 36, No. 11, pp. 3806-3808.
Busico, Vincenzo et al., Block Copolymers of Highly Isotactic Polypropylene via Controlled Ziegler-Natta Polymerization, Macromolecules, 2004, vol. 37, No. 22, pp. 8201-8203.
Busico, Vincenzo et al., Design of stereoselective Ziegler-Natta propene polymerization catalysts, PNAS, 2006, vol. 103, No. 42, pp. 15321-15326.
Ciancaleoni, Gianluca et al., Structure/Properties Relationship for Bis{phenoxyamine}Zr(IV)-Based Olefin Polymerization Catalysts: A Simple OFT Model to Predict Catalytic Activity, Macromolecules, 2012, vol. 45, pp. 4046-4053.
Cipullo, Roberta et al., Improving the Behavior of Bis(phenoxyamine) Group 4 Metal Catalysts for Controlled Alkene Polymerization, 2009, Macromolecules, vol. 42, pp. 3869-3872.
Clarkson, Guy et al., Group 4 catalysts for ethene polymerization containing tetradentate salicylaldiminato ligands, 2006, Dalton Trans., pp. 5484-5491.
Cohen, AD et al., Construction of C1-symmetric zirconium complexes by the design of new Salan ligands. Coordination chemistry and preliminary polymerisation catalysis studies, Chem. Commun, 2008, pp. 2149-2151.
Cohen, AD et al., C1-Symmetric Zirconium Complexes of [ONNO#]-Type Salan Ligands: Accurate Control of Catalyst Activity, Isospecificity, and Molecular Weight in 1-Hexene Polymerization, Organometallics, 2009, vol. 28, No. 5, pp. 1391-1405.
Cohen, AD et al., Same Ligand, Different Metals: Diiodo-Salan Complexes of the Group 4 Triad in Isospecific Polymerization of 1-Hexene and Propylene, Macromolecules, 2010, vol. 43, No. 4, pp. 1689-1691.
Corradini, Paolo et al., Do New Century Catalysts Unravel the Mechanism of Stereocontrol of Old Ziegler-Natta Catalysts?, Accounts of Chemical Research, 2004, vol. 37, No. 4, pp. 231-241.
Demetgul, Cahit et al., Synthesis and characterization of a Schiff base derived from 2-aminobenzylamine and its Cu(II) complex: electropolymerization of the complex on a platinum electrode, Journal of Coordination Chemistry, 2010, vol. 63, No. 12, pp. 2181-2191.
Egami, Hiromichi et al., Fe(salan)-Catalyzed Asymmetric Oxidation of Sulfides with Hydrogen Peroxide in Water, 2007, J. Am. Chem. Soc., vol. 129, pp. 8940-8941.
Egami, Hiromichi et al., Nb(salan)-Catalyzed Asymmetric Epoxidation of Allylic Alcohols with Hydrogen Peroxide, 2008, J. Am. Chem. Soc., vol. 47, pp. 5171-5174.
Egami, Hiromichi et al., Oxidation Catalysis of Nb(Salan) Complexes: Asymmetric Epoxidation of Allylic Alcohols Using Aqueous Hydrogen Peroxide As an Oxidant, 2010, J. Am. Chem. Soc., vol. 132, pp. 5886-5895.
Egami, Hiromichi et al., Enantioenriched Synthesis of C1-Symmetric BINOLs: Iron-Catalyzed Cross-Coupling of 2-Naphthols and Some Mechanistic Insight, 2010, J. Am. Chem. Soc., vol. 132, pp. 13633-13635.
Gendler, Shimrit, et al., Titanium and Zirconium Complexes of Robust Salophan Ligands. Coordination Chemistry and Olefin Polymerization Catalysis, J. Am. Chem. Soc., 2008, vol. 130, pp. 2144-2145.
Groysman, Stanislav et al., Salophan Complexes of Group IV Metals, Eur. J. Inorg. Chem. 2005, pp. 2480-2485.
Kondo, Shoichi et al., A μ-Oxo-μ-η2:η2-Peroxo Titanium Complex as a Reservoir of Active Species in Asymmetric Epoxidation Using Hydrogen Peroxide, 2008, Agnew. Chem. Int. Ed., vol. 47, pp. 10195-10198.
Lamberti, Marina et al., Mechanism of stereospecific polymerization of α-olefins by late-transition metal and octahedral group 4 metal catalysts, Coord. Chem. Rev. vol. 253, 2009, pp. 2082-2097.
Leflon, P. et al., Determination of aluminum in bone in haemodialyzed patients, using inductively coupled argon plasma emission spectrometry, Clinica Chimica Acta, 1990, vol. 191, issues 1-2, pp. 31-38.
Manna, Cesar M. et al., Markedly different cytotoxicity of the two enantiomers of C2-symmetrical Ti(IV) phenolato complexes; mechanistic implications, 2010, Dalton Trans., vol. 39, pp. 1182-1184.
Matsumoto, Kazuhiro et al., Asymmetric catalysis of metal complexes with non-planar ONNO ligands: salen, salalen and salan, Chem. Commun., 2007, pp. 3619-3627.
Matsumoto, Kazuhiro et al., Asymmetric epoxidation of olefins catalyzed by Ti(salan) complexes using aqueous hydrogen peroxide as the oxidant, 2008, Pure and Applied Chemistry, vol. 80, pp. 1071-1077.
Matsumoto, Kazuhiro et al., Highly Enantioselective Epoxidation of Styrenes Catalyzed by Proline-Derived C1-Symmetric Titanium(Salan) Complexes, Angew. Chem. Int. Ed. 2009, vol. 48, pp. 7432-7435.
Meker, Sigalit. et al., Major impact of N-methylation on cytotoxicity and hydrolysis of salan Ti(IV) complexes: sterics and electronics are intertwined, 2011, Dalton Trans., vol. 40, pp. 9802-9809.
Nakano, Koji et al., Alternating Copolymerization of Cyclohexene Oxide with Carbon Dioxide Catalyzed by (salalen) CrCl Complexes, Macromelecules, 2009, vol. 42, pp. 6972-6980.
Press, Konstantin et al., Salalen Titanium Complexes in the Highly Isospecific Polymerization of 1-Hexene and Propylene, Angew. Chem., Int. Ed., 2011, vol. 50, pp. 3529-3532.
Press, Konstantin et al., Zirconium and hafnium Salalen complexes in isospecific polymerisation of propylene, Dalton Trans., 2013, vol. 42, pp. 9096-9103.
Sawada, Yuji, et al., Titanium-Salan-Catalyzed Asymmetric Epoxidation with Aqueous Hydrogen Peroxide as the Oxidant, Agnew. Chem. Int. Ed., 2006, vol. 45, pp. 3478-3480.
Segal, Sharon et al., Isospecific Polymerization of Vinylcyclohexane by Zirconium Complexes of Salan Ligands, Macromolecules, 2008, vol. 41, No. 5, pp. 1612-1617.
Segal, Sharon et al., Zirconium and Titanium Diamine Bis(phenolate) Catalysts for α-Olefin Polymerization: From Atactic Oligo(1-hexene) to Ultrahigh-Molecular-Weight Isotactic Poly(1-hexene), Organomellics, 2005, vol. 24, No. 2, pp. 200-202.
Sergeeva, Ekaterina et al., Salan ligands assembled around chiral bipyrrolidine: predetermination of chirality around octahedral Ti and Zr centres, Chem. Commun, 2009, pp. 3053-3055.

(56) References Cited

OTHER PUBLICATIONS

Sergeeva, Ekaterina et al., 2,2'-Bipyrrolidine versus 1,2-Diaminocyclohexane as Chiral Cores for Helically Wrapping Diamine-Diolate Ligands, Inorganic Chemistry, 2009, vol. 48, No. 17, pp. 8075-8077.

Seyforth, Dietmar, Alkyl and Aryl Derivatives of the Alkali Metals: Strong Bases and Reactive Nucleophiles. 2. Wilhelm Schlenk's Organoalkali-Metal Chemistry. The Metal Displacement and the Transmetalation Reactions. Metalation of Weakly Acidic Hydrocarbons. Superbases, Organometallics, 2009, vol. 28, pp. 2-33.

Stopper, Ayellet et al., Ring-Opening Polymerization of Lactide with Zr Complexes of {Onso} Ligands: From Heterotactically Inclined to Isotactically Inclined Poly(lactic acid), Macromolecules, 2012, vol. 45, pp. 698-704.

Strianese M., et al., A Comparative Study on the Polymerization of α-Olefins Catalyzed by Salen and Salan Zirconium ComplexesMacromol. Chem. Phys. 2008, vol. 209, pp. 585-592.

Talarico, Giovanni et al., Origin of the Regiochemistry of Propene Insertion at Octahedral Column 4 Polymerization Catalysts: Design or Serendipity?, J. Am. Chem. Soc., 2003, vol. 125, pp. 7172-7173.

Tshuva, Edit Y. et al., Isospecific Living Polymerization of 1-Hexene by a Readily Available Nonmetallocene C2-Symmetrical Zirconium Catalyst, J. Am. Chem. Soc., 2000, vol. 122, pp. 10706-10707.

Yeori et al., Salalen: a hybrid Salan/Salen tetradentate [ONNO]-type ligand and its coordination behavior with group IV metals, Inorg. Chem. Commun., vol. 7, 2004, pp. 280-282.

Yeori, Adi et al., Diastereoisomerically Selective Enantiomerically Pure Titanium Complexes of Salan Ligands: Synthesis, Structure, and Preliminary Activity Studies, Inorganic Chemistry, 2005, vol. 44, No. 13, pp. 4466-4468.

Yeori, Adi et al., Diastereomerically-Specific Zirconium Complexes of Chiral Salan Ligands: Isospecific Polymerization of 1-Hexene and 4-Methyl-1-pentene and Cyclopolymerization of 1,5-Hexadiene, J. Am. Chem. Soc, 2006, vol. 128, pp. 13062-13063.

Yeori, Adi et al., Cyclopolymerization of 1,5-Hexadiene by Enantiomerically-Pure Zirconium Salan Complexes. Polymer Optical Activity Reveals α-Olefin Face Preference, Macromolecules, 2007, vol. 40, No. 24, pp. 8521-8523.

Zucchini, U. et al., Synthesis and Properties of Some Titanium and Zirconium Benzyl Derivatives, J. Organomet. Chem., 1971, vol. 26, pp. 357-372.

PCT/US2013/046538 International Search Report and Written Opinion, Nov. 8, 2013.

PCT/US2013/046582 International Search Report and Written Opinion, Nov. 5, 2013.

PCT/US2013/046601 International Search Report and Written Opinion, Nov. 13, 2013.

* cited by examiner

Molecular structure of Lig$^5$Zr(OtBu)$_2$

Molecular structure of Lig$^5$Hf(OtBu)$_2$

Molecular structure of Lig$^9$Zr(OtBu)$_2$

Molecular structure of Lig$^{12}$Zr(OtBu)$_2$

PHENYLENE-BRIDGED SALALEN CATALYSTS

CROSS REFERENCE TO RELATED APPLICATION(S)

This claims priority to and the benefit of provisional application U.S. 61/972,860, filed Mar. 31, 2014.

FIELD OF THE INVENTION

This invention relates to phenylene-bridged Salalen catalyst compounds and catalyst systems, processes utilizing such catalysts, and polymers produced thereby.

BACKGROUND OF THE INVENTION

Olefin polymerization catalysts are of great use in industry. Hence there is interest in finding new catalyst systems that increase the commercial usefulness of the catalyst and allow the production of polymers having improved properties.

WO2011/158241 is generally directed to the use of homogeneous catalytic systems which include a pre-catalyst complex of a Group IV metal and a salalen ligand in the polymerization of alpha-olefins. The alpha-olefin polymers obtained are characterized by controlled levels of tacticity. Also disclosed are salalen ligands and complexes thereof with Group IV metals.

EP1849778, EP2003135, JP2007284438, Berkessel et al. "A Practical and Versatile Access to Dihydrosalen (Salalen) Ligands: Highly Enantioselective Titanium In Situ Catalysts for Asymmetric Epoxidation with Aqueous Hydrogen Peroxide, Adv. Syn-Cat. 2007, 349, 2385-2391, and Nakano et al. "Alternating Copolymerization of Cyclohexene Oxide with Carbon Dioxide Catalyzed by (salalen)CrCl Complexes", Macromolecules 2009, 42, 6972-6980 are generally directed to methods and uses of various Group 4-6 salalen transition metal compounds as catalysts for various materials and processes.

Whitelaw et al. "Group 4 Salalen Complexes and Their Application for the Ring-Opening Polymerization of rac-Lactide" Inorg. Chem., 2010, 49 (15), pp 7176-7181 is generally directed to group 4 salalen complexes suitable to polymerize lactic acid to produce rac-lactide and isotactic polylactic acid both in the melt and in solution.

A. Yeori, et al. "Salalen: a hybrid Salan/Salen tetradentate AONNOU type ligand and its coordination behavior with group IV metals" Inorg. Chem. Commun. 2004, 7, 280-282; and Tshuva et al. "Isospecific living polymerization of 1-hexene by a readily available nonmetallocene 02-symmetrical zirconium catalyst, J. Am. Chem. Soc. 2000, 122, 10706-10707 are generally directed to catalysts for polymerization of alpha olefins.

Press et al. "Salalen Titanium Complexes in the Highly Isospecific Polymerization of 1-Hexene and Propylene" Angew. Chem. Int. Ed. 2011, 50, 3529-3532 is generally directed to salalen catalysts capable of forming isotactic polypropylene; and Press et al. "Zirconium and hafnium Salalen complexes in isospecific polymerisation of propylene", Dalton Trans., 2013, 42, 9096 is generally directed to dibenzylzirconium and dibenzylhafnium Salalen complexes in polymerization of propylene with MAO as a cocatalyst.

Other references of interest include U. Zucchini et al. J. Organomet. Chem. 1971, 26, 357-372; Bryliakov et al., Eur. J. Org. Chem. 2008, 3369-3376; Gendler et al., J. Am. Chem. Soc. 2008, 130, 2144-2145; Cohen et al. Macromolecules 2010, 43, 1689-1691, and Altomare et al., J. Appl. Cryst., 1993, 26, 343-350. All the above listed references are incorporated by reference herein.

Accordingly, there is a need in the art for new and improved catalysts and catalyst systems to obtain new and improved polyolefins, polymerization processes, and the like. Accordingly, there is a need in the art for new and improved catalyst systems for the polymerization of olefins, to achieve specific polymer properties such as high tacticity, high molecular weight or a combination thereof.

SUMMARY OF THE INVENTION

The instant disclosure is directed to catalyst compounds and catalyst systems comprising such compounds, processes for the preparation of the catalyst compounds and systems, and processes for the polymerization of olefins using such catalyst compounds and systems.

In an embodiment according to the invention, a catalyst compound is represented by the formula:

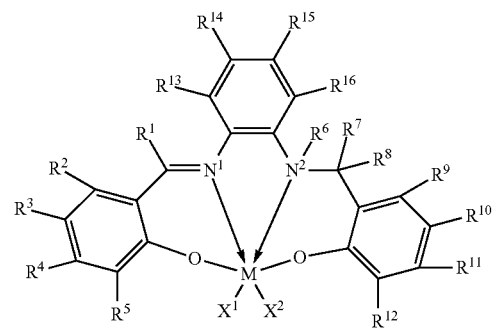

wherein each solid line represents a covalent bond and each arrow represents a bond having a varying degree of covalency and a varying degree of coordination;

wherein M is a Group 4 metal;

$N^1$ and $N^2$ are nitrogen;

O is oxygen;

each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

In an embodiment according to the invention, a catalyst system comprises an activator and a catalyst compound represented by the formula:

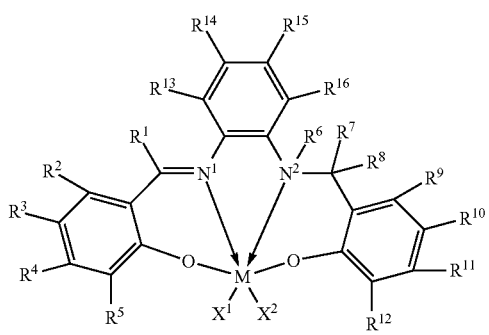

wherein each solid line represents a covalent bond and each arrow represents a bond having a varying degree of covalency and a varying degree of coordination;
wherein M is a Group 4 metal;
$N^1$ and $N^2$ are nitrogen;
O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

In an embodiment according to the invention, a process comprises contacting one or more olefins with a catalyst system at a temperature, a pressure, and for a period of time sufficient to produce a polyolefin, the catalyst system comprising an activator and a catalyst compound represented by the formula:

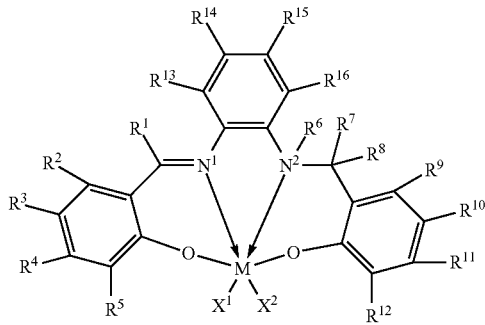

wherein each solid line represents a covalent bond and each arrow represents a bond having a varying degree of covalency and a varying degree of coordination;
wherein M is a Group 4 metal;
$N^1$ and $N^2$ are nitrogen;
O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

DETAILED DESCRIPTION

Figure 1:
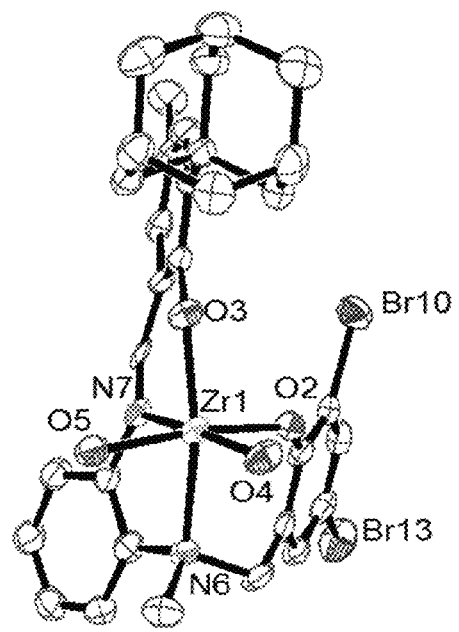
FIG. 1 shows the molecular structure of a catalyst as determined by X-ray diffraction according to an embodiment of the invention.

For the purposes of this invention and the claims thereto, the numbering scheme for the Periodic Table Groups is used as in Chem. Eng. News, 1985, 63, 27. Therefore, a "Group 4 metal" is an element from Group 4 of the Periodic Table.

In the structures depicted throughout this specification and the claims, a solid line indicates a bond, an arrow indicates that the bond may be dative, and each dashed line represents a bond having a varying degree of covalency and a varying degree of coordination.

The terms "hydrocarbyl radical," "hydrocarbyl" and "hydrocarbyl group" are used interchangeably throughout this document unless otherwise specified. For purposes of this disclosure, a hydrocarbyl radical is defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic (aromatic or non-aromatic); and includes hydrocarbyl radicals substituted with other hydrocarbyl radicals and/or one or more functional groups comprising elements from Groups 13 to 17 of the periodic table of the elements.

The term "substituted" means that a hydrogen atom and/or a carbon atom in the base structure has been replaced with a hydrocarbyl radical, and/or a functional group, and/or a heteroatom or a heteroatom containing group. Accordingly, the term hydrocarbyl radical includes heteroatom containing groups. For purposes herein, a heteroatom is defined as any atom other than carbon and hydrogen. For example, methyl cyclopentadiene (Cp) is a Cp group, which is the base structure, substituted with a methyl radical, which may also be referred to as a methyl functional group, ethyl alcohol is an ethyl group, which is the base structure, substituted with an —OH functional group, and pyridine is a phenyl group having a carbon in the base structure of the benzene ring substituted with a nitrogen atom.

For purposes herein, a hydrocarbyl radical may be independently selected from substituted or unsubstituted methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butyryl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl.

For purposes herein, hydrocarbyl radicals may also include isomers of saturated, partially unsaturated and aromatic cyclic structures wherein the radical may additionally be subjected to the types of substitutions described above. The terms "aryl", "aryl radical", and/or "aryl group" refer to aromatic cyclic structures, which may be substituted with hydrocarbyl radicals and/or functional groups as defined herein. Examples of aryl radicals include: acenaphthenyl, acenaphthylenyl, acridinyl, anthracenyl, benzanthracenyls, benzimidazolyl, benzisoxazolyl, benzofluoranthenyls, benzofuranyl, benzoperylenyls, benzopyrenyls, benzothiazolyl, benzothiophenyls, benzoxazolyl, benzyl, carbazolyl, carbolinyl, chrysenyl, cinnolinyl, coronenyl, cyclohexyl, cyclohexenyl, methylcyclohexyl, dibenzoanthracenyls, fluoranthenyl, fluorenyl, furanyl, imidazolyl, indazolyl, indenopyrenyls, indolyl, indolinyl, isobenzofuranyl, isoindolyl, isoquinolinyl, isoxazolyl, methyl benzyl, methylphenyl, naphthyl, oxazolyl, phenanthrenyl, phenyl, purinyl, pyrazinyl, pyrazolyl, pyrenyl, pyridazinyl, pyridinyl, pyrimidinyl, pyrrolyl, quinazolinyl, quinolonyl, quinoxalinyl, thiazolyl, thiophenyl, and the like.

It is to be understood that for purposes herein, when a radical is listed, it indicates that the base structure of the radical (the radical type) and all other radicals formed when that radical is subjected to the substitutions defined above. Alkyl, alkenyl, and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (and cyclobutenyls and cyclopropenyls). Cyclic compounds having substitutions include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

Likewise the terms "functional group", "group" and "substituent" are also used interchangeably throughout this document unless otherwise specified. For purposes herein, a functional group includes both organic and inorganic radicals, as well as moieties comprising elements from Groups 13, 14, 15, 16, and 17 of the periodic table of elements. Suitable functional groups may include hydrocarbyl radicals, e.g., alkyl radicals, alkene radicals, aryl radicals, and/or halogen (Cl, Br, I, F), O, S, Se, Te, $NR^{\ddagger}_x$, $OR^{\ddagger}$, $SeR^{\ddagger}$, $TeR^{\ddagger}$, $PR^{\ddagger}_x$, $AsR^{\ddagger}_x$, $SbR^{\ddagger}_x$, $SR^{\ddagger}$, $BR^{\ddagger}_x$, $SiR^{\ddagger}_x$, $GeR^{\ddagger}_x$, $SnR^{\ddagger}_x$, $PbR^{\ddagger}_x$, and/or the like, wherein each R is independently hydrogen or a $C_1$ to $C_{20}$ hydrocarbyl as defined above and wherein x is the appropriate integer to provide an electron neutral moiety. Other examples of functional groups include those typically referred to as amines, imides, amides, ethers, alcohols (hydroxides), sulfides, sulfates, phosphides, halides, phosphonates, alkoxides, esters, carboxylates, aldehydes, and the like.

For purposes herein, a supported catalyst and/or activator refers to a catalyst compound, an activator, or a combination thereof located on, in or in communication with a support wherein the activator, the catalyst compound, or a combination thereof are deposited on, vaporized with, bonded to, incorporated within, adsorbed or absorbed in, adsorbed or absorbed on, the support.

For purposes herein, an electron withdrawing functional group is an atom or functional group that removes electron density from a conjugated π system via resonance or inductive electron withdrawal, for example, thus making the π system more electrophilic. Examples of electron withdrawing groups include nitro groups ($-NO_2$), quaternary amine groups ($-NR^{\alpha}_3{}^+$), trihalide groups ($-CF_3$, $-CCl_3$, $-CBr_3$, $-CI_3$), cyano groups ($-CN$), isocyano groups ($R'CN-$); sulfonates ($-SO_3H$), carboxylic acids ($-COOH$), esters ($-COOR^{\alpha}$), aldehydes ($-CHO$), and/or ketones ($-COR^{\alpha}$), or a combination thereof, or the like, wherein each $R^{\alpha}$ is independently hydrogen or a $C_1$-$C_{20}$ hydrocarbyl radical or a $C_1$-$C_{20}$ alkyl radical.

Where reference is made herein to two substituents joining together to form a cyclic or polycyclic ring structure, one substituent is directly bridged to another substituent when the two substituents together form only a covalent bond containing no atoms, i.e., the substituents are not directly bridged if they together comprise a bridge of at least one atom.

For purposes herein a bulky functional group is defined as a functional group having a molecular size greater than or equal to an isopropyl moiety. Accordingly, for purposes herein a bulky functional group includes substituted or unsubstituted bulky aliphatic radicals having three carbons or more, bulky alicyclic radicals having three carbons or more, and/or bulky aromatic radicals having 5 carbons or more, each having a molecular size greater than or equal to an isopropyl moiety.

For purposes herein an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer.

For purposes herein a "polymer" has two or more of the same or different "mer" units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, the definition of copolymer, as used herein, includes terpolymers and the like. An oligomer is typically a polymer having a low molecular weight, such as having an Mn of less than 25,000 g/mol, or in an embodiment according to the invention, less than 2,500 g/mol, or a low number of mer units, such as 75 mer units or less. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

As used herein, "isotactic" is defined as having at least 10% isotactic pentads (meso-pentad [mmmm]), preferably having at least 40% meso-pentad [mmmm] of methyl groups derived from propylene according to analysis by $^{13}$C-NMR as described herein. For purposes herein, a highly isotactic polyolefin comprises a meso-pentad [mmmm] content or concentration of greater than or equal to about 60% meso-pentad [mmmm], or greater than or equal to about 85% meso-pentad [mmmm], or greater than or equal to about 90% meso-pentad [mmmm], or greater than or equal to about 95% meso-pentad [mmmm], or greater than or equal to about 98% meso-pentad [mmmm] as determined by $^{13}$C NMR, based on the total amount of pentads present in the material. As used herein, "syndiotactic" is defined as having at least 10% syndiotactic pentads, preferably at least 40%, according to analysis by $^{13}$C-NMR.

For purposes herein, polypropylene microstructure is determined by $^{13}$C-NMR spectroscopy, including the concentration of isotactic and syndiotactic diads ([m] and [r]), triads ([mm] and [rr]), and pentads ([mmmm] and [rrrr]). The designation "m" or "r" describes the stereochemistry of pairs of contiguous propylene groups, "m" referring to meso and "r" to racemic. Samples are dissolved in d$_2$-1,1,2,2-tetrachloroethane, and spectra recorded at a temperature between 100° C. and 150° C., typically 120° C.-125° C. using a commercially available 100 MHz (or higher) NMR spectrometer. Polymer resonance peaks are referenced to mmmm=21.8 ppm. Calculations involved in the characterization of polymers by NMR are described by F. A. Bovey in Polymer Conformation and Configuration (Academic Press, New York 1969) and J. Randall in Polymer Sequence Determination, $^{13}$C-NMR Method (Academic Press, New York, 1977).

$^{13}$C NMR data is collected at between 100° C. and 150° C. in a 5 mm dual $^{13}$C/$^1$H probe or 10 mm probe using a commercially available NMR (e.g., a Varian or Bruker NMR spectrometer) with a $^1$Hydrogen frequency of at least 100 MHz. A pulse angle between 20° and 90° is used with an acquisition time adjusted to give a digital resolution between 0.1 and 0.12 Hz, at least a 1 second pulse acquisition delay time with continuous broadband proton decoupling using swept square wave modulation without gating is employed during the entire acquisition period. The spectra are acquired using time averaging to provide a signal to noise level adequate to measure the signals of interest. Samples are dissolved in tetrachloroethane-d$_2$ at concentrations between 10 to 15 wt % and/or using 1,2-dichlorobenzene-d$_4$ as a solvent prior to being inserted into the spectrometer magnet. Prior to data analysis spectra were referenced by setting the chemical shift of the (—CH$_2$—)$_n$ signal where n>6 to 29.9 ppm.

Determination of chain ends for quantization are identified using the signals shown in the table below.

| Chain End | $^{13}$CNMR Chemical Shift |
|---|---|
| P~i-Bu | 23-5 to 25.5 and 25.8 to 26.3 ppm |
| E~i-Bu | 39.5 to 40.2 ppm |
| P~Vinyl | 41.5 to 43 ppm |
| E~Vinyl | 33.9 to 34.4 ppm |

The "allyl chain end to vinylidene chain end ratio" is defined to be the ratio of the percentage of allyl chain ends to the percentage of vinylidene chain ends.

The "allyl chain end to vinylene chain end ratio" is defined to be the ratio of the percentage of allyl chain ends to the percentage of vinylene chain ends.

The term "allyl chain end" (also referred to as "allylic vinyl group" or "allylic vinyl end group") is defined to be a polymer having at least one terminus represented by (CH$_2$CH—CH$_2$-polymer) according to the following formula:

where M represents the polymer chain.

The amount of allyl chain ends is determined using $^1$H NMR using deuterated tetrachloroethane as the solvent and/or via $^{13}$C NMR, consistent with literature values reported for proton and carbon assignments wherein neat perdeuterated tetrachloroethane is used for proton spectra and a 50:50 mixture of normal and perdeuterated tetrachloroethane is used for carbon spectra; all spectra are recorded at a temperature of at least 100° C. on a BRUKER AM 300 spectrometer operating at 300 MHz for proton and 75.43 MHz for carbon, for vinyl terminated propylene oligomers, as in *J. American Chemical Soc.*, 114, 1992, pp. 1025-1032.

Vinyl terminated polymers typically also have a saturated chain end, also referred to as a methyl end. In polymerizations comprising C$_4$ or greater monomers (or "higher olefin" monomers), the saturated chain end may be a C$_4$ or greater (or "higher olefin") chain end, as shown in the formula below:

higher olefin chain end where M represents the polymer chain and n is an integer selected from 4 to 40. This is especially true when there is substantially no ethylene or propylene in the polymerization. In an ethylene/(C$_4$ or greater monomer) copolymerization, the polymer chain may initiate growth in an ethylene monomer, thereby generating a saturated chain end which is an ethyl chain end. In polymerizations where propylene is present, the polymer chain may initiate growth in a propylene monomer, thereby generating an isobutyl chain end. An "isobutyl chain end" is defined to be an end or terminus of a polymer, represented as shown in the formula below:

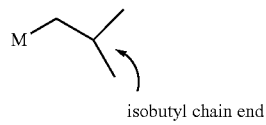

isobutyl chain end where M represents the polymer chain. Isobutyl chain ends are determined according to the procedure set out in WO 2009/155471.

For the purposes of this disclosure, the term "α-olefin" includes C$_2$-C$_{30}$ olefins. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

The terms "catalyst", "catalyst compound", and "transition metal compound" are defined to mean a compound capable of initiating polymerization of monomers to polymers under the appropriate conditions. In the description herein, the catalyst may be described as a catalyst precursor, a pre-catalyst compound, or a transition metal compound, and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is a combination of at least one catalyst compound, at least one activator, an optional co-activator, and an optional support material, where the system can polymerize monomers to polymer. For the purposes of this invention and the claims thereto, when catalyst systems are described as comprising neutral stable forms of the components, it is well understood by one of ordinary skill in the art that the ionic form of the component is the form that reacts with the monomers to produce polymers.

For purposes herein the term "catalyst productivity" is a measure of how many grams of polymer (P) are produced using a polymerization catalyst comprising W grams of catalyst (cat), over a period of time of T hours; and may be expressed by the following formula: P/(T×W) and expressed in units of gPgcat$^{-1}$hr$^{-1}$. Conversion is the amount of monomer that is converted to polymer product, and is reported as mol % and is calculated based on the polymer yield and the amount of monomer fed into the reactor. Catalyst activity is a measure of how active the catalyst is and is reported as the mass of product polymer (P) produced per mole of catalyst (cat) used (kg P/mol cat).

An "anionic ligand" is a negatively charged ligand which donates one or more pairs of electrons to a metal ion. A "neutral donor ligand" is a neutrally charged ligand which donates one or more pairs of electrons to a metal ion.

A scavenger is a compound that is typically added to facilitate oligomerization or polymerization by scavenging impurities. Some scavengers may also act as activators and may be referred to as co-activators. A co-activator, that is not a scavenger, may also be used in conjunction with an activator to form an active catalyst. In an embodiment according to the invention, a co-activator can be pre-mixed with the catalyst compound to form an alkylated catalyst compound.

The term "ethylene polymer" includes homopolymers and/or copolymers of ethylene and one or more additional olefins and/or alpha olefins, including, for example, propylene, and/or butene and/or hexene, and/or octene. For purposes herein low density polyethylene has a density of 0.915 to less than 0.935 g/cm$^3$, linear low density polyethylene has a density of 0.915 to less than 0.925 g/cm$^3$, ultra-low density polyethylene has a density of 0.86 to less than 0.90 g/cm$^3$, very low density polyethylene has a density of 0.90 to less than 0.915 g/cm$^3$, medium density polyethylene has a density of 0.935 to less than 0.945 g/cm$^3$, high density polyethylene has a density of 0.945 to 0.98 g/cm$^3$. Ultrahigh molecular weight polyethylene has a molecular weight greater than 1 million g/mol, typically from about 3 to about 6 million g/mol and a density from about 0.93 to about 0.94 g/cm$^3$.

As used herein, Mn is number average molecular weight as determined by gel permeation chromatography (GPC). Mw is weight average molecular weight determined by GPC, and Mz is z average molecular weight determined by GPC, wt % is weight percent, and mol % is mole percent. Unless otherwise noted, all molecular weight units, e.g., Mw, Mn, Mz, are g/mol.

For purposes herein, Mn, Mw, Mz, number of carbon atoms, g value and g'$_{vis}$ are determined by using a commercially available High Temperature Size Exclusion Chromatograph (e.g., from Waters Corporation or Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, 6812-6820, (2001) and references therein. Three Polymer Laboratories PLgel 10 mm Mixed-B LS columns are used. The nominal flow rate is 0.5 cm$^3$/min, and the nominal injection volume is 300 µL. The various transfer lines, columns and differential refractometer (the DRI detector) are contained in an oven maintained at 145° C. Solvent for the experiment is prepared by dissolving 6 grams of butylated hydroxy toluene as an antioxidant in 4 liters of Aldrich reagent grade 1, 2, 4 trichlorobenzene (TCB). The TCB mixture is then filtered through a 0.7 µm glass pre-filter and subsequently through a 0.1 µm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/ml at room temperature and 1.324 g/ml at 14 5° C. The injection concentration is from 0.75 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on 1 to 1.5 hours before running the samples. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 145° C. and 2=690 nm. For purposes of this invention and the claims thereto (dn/dc)=0.104 for propylene polymers, 0.098 for butene polymers and 0.1 otherwise. Units on parameters throughout this description of the SEC method are such that concentration is expressed in g/cm$^3$, molecular weight is expressed in g/mole, and intrinsic viscosity is expressed in dL/g.

The LS detector is a Wyatt Technology High Temperature mini-DAWN. The molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle $\theta$, c is the polymer concentration determined from the DRI analysis, $A_2$ is the second virial coefficient [for purposes of this invention, $A_2$=0.0006 for propylene polymers, 0.0015 for butene polymers and 0.001 otherwise], (dn/dc)=0.104 for propylene polymers, 0.098 for butene polymers and 0.1 otherwise, $P(\theta)$ is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and $\lambda$=690 nm.

A high temperature Viscotek Corporation viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [$\eta$], at each point in the chromatogram is calculated from the following equation:

$$\eta s = c[\eta] + 0.3(c[\eta])^2$$

where c is concentration and was determined from the DRI output.

The branching index ($g'_{vis}$) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'vis = \frac{[\eta]_{avg}}{kM_v^\alpha}$$

where, for purpose of this invention and claims thereto, $\alpha$=0.695 and k=0.000579 for linear ethylene polymers, $\alpha$=0.705 k=0.000262 for linear propylene polymers, and $\alpha$=0.695 and k=0.000181 for linear butene polymers. $M_v$ is the viscosity-average molecular weight based on molecular weights determined by LS analysis.

"g" also called a "g value" is defined to be $Rg^2_{pm}/Rg^2_{ls}$, where $Rg_{pm}$ is the radius of gyration for the polymacromer, $Rg^2_{ls}$ is the radius of gyration for the linear standard, and $Rg_{ls}=K_s M^{0.58}$ where $K_s$ is the power law coefficient (0.023 for linear polyethylene, 0.0171 for linear polypropylene, and 0.0145 for linear polybutene), and M is the molecular weight as described above, $Rg_{pm}=K_T M^{\alpha_s}$. $\alpha_s$ is the size coefficient for the polymacromer; $K_T$ is the power law coefficient for the polymacromer. See Macromolecules, 2001, 34, 6812-6820, for guidance on selecting linear standards having the molecular weight and comonomer content, and determining K coefficients and $\alpha$ exponents.

Ethylene content in ethylene copolymers is determined by ASTM D 5017-96, or an equivalent thereof, except that the minimum signal-to-noise should be 10,000:1. Propylene content in propylene copolymers is determined by following the approach of Method 1 in Di Martino and Kelchermans, *J. Appl. Polym. Sci.* 56, 1781 (1995), and using peak assignments from Zhang, *Polymer* 45, 2651 (2004) for higher olefin comonomers.

Melting temperature (or melting point, $T_m$) and heat of fusion ($\Delta H$ or $H_f$) are measured using Differential Scanning calorimetry (DSC) on a commercially available instrument (e.g., TA Instruments 2920 DSC) using the following procedure. Typically, 6 to 10 mg of molded polymer or plasticized polymer are sealed in an aluminum pan and loaded into the instrument at room temperature. Data are acquired by heating the sample to at least 30° C. above its melting temperature, typically 220° C. for polypropylene, at a heating rate of 10° C./min. The sample is held for at least 5 minutes at this temperature to destroy its thermal history. Then the sample is cooled from the melt to at least 50° C. below the crystallization temperature, typically –100° C. for polypropylene, at a cooling rate of 20° C./min. The sample is held at this temperature for at least 5 minutes, and finally heated at 10° C./min to acquire additional melting data (second heat). The endothermic melting transition (first and second heat) and exothermic crystallization transition are analyzed according to standard procedures. The melting temperatures (Tm) reported are the peak melting temperatures from the second heat unless otherwise specified. For polymers displaying multiple peaks, the melting temperature is defined to be the peak melting temperature from the melting trace associated with the largest endothermic calorimetric response (as opposed to the peak occurring at the highest temperature). Likewise, the crystallization temperature is defined to be the peak crystallization temperature from the crystallization trace associated with the largest exothermic calorimetric response (as opposed to the peak occurring at the highest temperature).

Areas under the DSC curve are used to determine the heat of transition (heat of fusion, $H_f$, upon melting or heat of crystallization, $H_c$, upon crystallization), which can be used to calculate the degree of crystallinity (also called the percent crystallinity). The percent crystallinity (X %) is calculated using the formula: [area under the curve (in J/g)/H° (in J/g)]*100, where H° is the ideal heat of fusion for a perfect crystal of the homopolymer of the major monomer component. These values for H° are to be obtained from the *Polymer Handbook, Fourth Edition*, published by John Wiley and Sons, New York 1999, except that a value of 290 J/g is used for H° (polyethylene), a value of 140 J/g is used for H° (polybutene), and a value of 207 J/g is used for H° (polypropylene).

The following abbreviations may be used through this specification: Me is methyl, Ph is phenyl, Et is ethyl, Pr is propyl, iPr is isopropyl, n-Pr is normal propyl, Bu is butyl, iso-butyl is isobutyl, sec-butyl refers to secondary butyl, tert-butyl, refers to tertiary butyl, n-butyl is normal butyl, pMe is para-methyl, Bn is benzyl, THF or thf is tetrahydrofuran, Mes is mesityl, also known as 1,3,5-trimethylbenzene, Tol is toluene, Flu is fluorenyl, TMS is trimethylsilyl, TIBAL is tri-isobutylaluminum, TNOAL is triisobutyl n-octylaluminum, MAO is methylalumoxane, MOMO is methoxymethoxy (also referred to as methoxymethyl ether), N is nitrogen (including that $N^1$, $N^2$, $N^3$ and $N^4$ are each representative of a single nitrogen atom) and O is oxygen.

For purposes herein, RT is room temperature, which is defined as 25° C. unless otherwise specified. All percentages are weight percent (wt %) unless otherwise specified.

In the description herein, the Salalen catalyst may be described as a catalyst precursor, a pre-catalyst compound, Salalen catalyst compound or a transition metal compound, and these terms are used interchangeably.

Catalyst Compounds

In an embodiment according to the invention, the catalyst comprises Group 3, 4, 5 and/or 6 monosubstituted (for a trivalent metal) or disubstituted (for a tetravalent metal) compounds supported by a tetradentate di-anionic phenylene bridged Salalen ligand, useful to polymerize olefins and/or α-olefins to produce polyolefins and/or poly(α-olefins). In an embodiment according to the invention, the catalyst compound is represented by the formula:

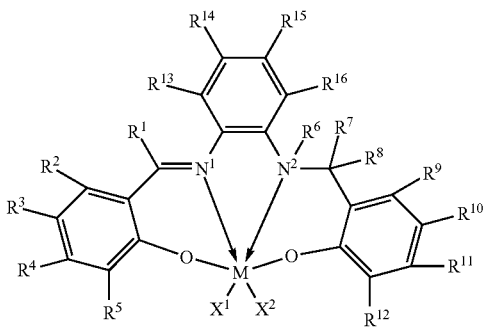

wherein each solid line represents a covalent bond and each arrow represents a bond having a varying degree of covalency and a varying degree of coordination;
wherein M is a Group 3, 4, 5, or 6 metal, or a Group 4 metal, or Ti, Zr, or Hf;
$N^1$ and $N^2$ are nitrogen;
O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure, provided however when M is trivalent $X^2$ is not present;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

In an embodiment according to the invention, M is Hf. In another embodiment according to the invention M is Ti. In another embodiment according to the invention M is Zr. In an embodiment according to the invention, each of $X^1$ and $X^2$ is, independently, a halogen or a benzyl radical.

In an embodiment according to the invention, each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a halogen, a $C_1$ to $C_{30}$ hydrocarbyl radical, or a $C_1$ to $C_{20}$ hydrocarbyl radical, or a $C_1$ to $C_{10}$ hydrocarbyl radical.

For purposes of this disclosure, the terms "$C_1$ to $C_{30}$ hydrocarbyl radical" and "$C_1$ to $C_{40}$ hydrocarbyl radical" include, but are not limited to ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, vinylnorbornane, cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

For purposes of this disclosure, the term "$C_1$ to $C_{20}$ hydrocarbyl radical" includes, but is not limited to ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 4-methyl-1-pentene, 3-methyl-1-pentene, 5-methyl-1-nonene, 3,5,5-trimethyl-1-hexene, vinylcyclohexane, vinylnorbornane, cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

In an embodiment according to the invention, at least one of $R^3$, $R^5$, $R^{10}$, and $R^{12}$ is, independently, an electron withdrawing functional group radical comprising —$NO_2$, —$CF_3$, —$CCl_3$, —$CBr_3$, —$Cl_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

For purposes of this disclosure, "$C_1$ to $C_{20}$ alkyl radical" includes, but is not limited to, ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 4-methyl-1-pentene, 3-methyl-1-pentene, 5-methyl-1-nonene, and 3,5,5-trimethyl-1-hexene.

In an embodiment according to the invention, at least one of $R^3$, $R^5$, $R^{10}$, and $R^{12}$ is, independently, a $C_1$ to $C_{30}$ aliphatic radical, a $C_1$ to $C_{20}$ aliphatic radical, a $C_1$-$C_{10}$ aliphatic radical, a $C_1$ to $C_{30}$ alicyclic radical, a $C_1$ to $C_{20}$ alicyclic radical, or a $C_1$-$C_{10}$ alicyclic radical.

For purposes of this disclosure, the term "aliphatic radicals" includes ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 4-methyl-1-pentene, 3-methyl-1-pentene, 5-methyl-1-nonene, and 3,5,5-trimethyl-1-hexene.

For purposes of this disclosure, the term "alicyclic radicals" includes vinylcyclohexane, and vinylnorbornane, cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

In an embodiment according to the invention, at least one (alternately two, three or four) of $R^3$, $R^5$, $R^{10}$, and $R^{12}$ is, independently, a bulky functional group radical having a molecular size greater than or equal to a molecular size of an isopropyl functional group radical.

In an embodiment according to the invention, at least one (alternately two, three or four) of $R^3$, $R^5$, $R^{10}$, and $R^{12}$ is, independently, a substituted or unsubstituted aliphatic radical having four carbons or more, a substituted or unsubstituted alicyclic radical having six carbons or more (preferably 6 to 20 carbon atoms), or a combination thereof.

In an embodiment according to the invention, at least one (alternately two, three or four) of $R^3$, $R^5$, $R^{10}$, and $R^{12}$ is, independently, a methyl radical, an adamantyl radical or a tert-butyl radical.

In an embodiment according to the invention, at least one (or both) of $R^5$ and $R^{12}$ is, independently, a substituted or unsubstituted carbazolyl radical.

For purposes of this disclosure, the term "substituted or unsubstituted carbazolyl" shall include compounds represented by the formula:

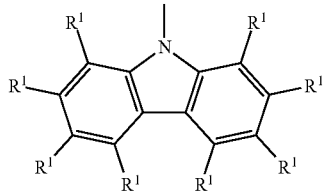

where each $R^1$ is, independently, H or a substituted or unsubstituted $C_1$ to $C_{30}$ hydrocarbyl radical, alternately a substituted or unsubstituted $C_1$ to $C_{20}$ hydrocarbyl radical such as methyl, ethyl, propyl, butyl, or the like.

In an embodiment according to the invention:
i) each of $R^3$ and $R^5$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and each of $R^{10}$ and $R^{12}$ is, independently, a $C_1$-$C_{10}$ aliphatic radical or a $C_1$-$C_{10}$ alicyclic radical; or
ii) each of $R^3$ and $R^5$ is, independently, a $C_1$-$C_{10}$ aliphatic radical or a $C_1$-$C_{10}$ alicyclic radical, and
each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F,
—Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

In an embodiment according to the invention:
i) each of $R^3$ and $R^5$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and each of $R^{10}$ and $R^{12}$ is, independently, a bulky functional group radical having a molecular size greater than or equal to a molecular size of an isopropyl functional group radical; or
ii) each of $R^3$ and $R^5$ is, independently, a bulky functional group radical having a molecular size greater than or equal to a molecular size of an isopropyl functional group radical, and each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

In an embodiment according to the invention, $R^2$ is identical in composition to $R^9$, $R^3$ is identical in composition to $R^{10}$, $R^4$ is identical in composition to $R^{11}$, $R^5$ is identical in composition to $R^{12}$, or a combination thereof.

In an embodiment according to the invention, $R^2$ is different in composition than $R^9$, $R^3$ is different in composition than $R^{10}$, $R^4$ is different in composition than $R^{11}$, $R^5$ is different in composition than $R^{12}$, or a combination thereof.

In an embodiment according to the invention M is Ti, Zr, or Hf, and each of $X^1$ and $X^2$ is $R^{15}$, $R^{14}$, $R^{13}$, independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, and wherein:
i) each of $R^3$ and $R^5$ is tert-butyl, $R^6$ is methyl, and each of $R^{10}$ and $R^{12}$ is independently F, Cl, Br, or I; or
ii) each of $R^3$ and $R^6$ is methyl, $R^5$ is adamantyl, and each of $R^{10}$ and $R^{12}$ is independently F, Cl, Br, or I; or
iii) each of $R^3$, $R^6$, and $R^{10}$ is methyl, and each of $R^5$ and $R^{10}$ is adamantyl;
iv) each of $R^3$, $R^5$, $R^{10}$ and $R^{12}$ is tert-butyl, and $R^6$ is methyl; or
v) each of $R^3$ and $R^5$ is independently F, Cl, Br, or I, each of $R^6$ and $R^{10}$ is methyl, and $R^{12}$ is adamantyl; or
vi) each of $R^3$, $R^5$, $R^{10}$, and $R^{12}$ is independently F, Cl, Br, or I, and $R^6$ is methyl; or
vii) each of $R^3$ and $R^6$ is methyl, $R^5$ is adamantyl, $R^{10}$ is tert-butyl, and $R^{12}$ is 4,4'-di-tert-butyl carbazolyl.

In an embodiment according to the invention, a catalyst system comprises an activator and a catalyst compound according to any embodiment of the invention disclosed herein.

In an embodiment according to the invention, a process comprises contacting one or more olefins with a catalyst system according to any one or combination of embodiments disclosed herein at a temperature, a pressure, and for a period of time sufficient to produce a polyolefin. In an embodiment according to the invention, the catalyst compound is disposed on a support.

In an embodiment according to the invention, the one or more olefins utilized according to one or more processes disclosed herein includes propylene, and the polyolefin produced according to one or more processes disclosed herein is a propylene polymer having a melting point of greater than 145° C. determined by differential scanning calorimetry, and the propylene polymer further comprises a meso-pentad [mmmm] content of greater than or equal to about 89%, as determined by $^{13}C$ NMR.

In an embodiment according to the invention one or more processes disclosed herein utilizes a catalyst compound according to one or more embodiments disclosed herein wherein M is Hf; $R^3$ is a methyl radical; $R^5$ is an adamantyl radical; and each of $R^{10}$ and $R^{12}$ is independently a bromine radical or an iodine radical.

In an embodiment according to the invention, the one or more olefins utilized according to one or more processes disclosed herein includes propylene, and the polyolefin produced according to one or more processes disclosed herein is a propylene polymer having a melting point of greater than 150° C. determined by differential scanning calorimetry, and the propylene polymer further comprises a meso-pentad [mmmm] content of greater than or equal to about 95%, as determined by $^{13}C$ NMR.

In an embodiment according to the invention one or more processes disclosed herein utilizes a catalyst compound according to one or more embodiments disclosed herein wherein M is Zr; $R^3$ is a methyl radical; $R^5$ is an adamantyl radical; and each of $R^{10}$ and $R^{12}$ is independently a bromine radical.

In an embodiment according to the invention, the one or more olefins utilized according to one or more processes disclosed herein includes propylene, and the polyolefin produced according to one or more processes disclosed herein is an atactic propylene polymer, and the propylene polymer further comprises a weight average molecular weight (Mw) of greater than 100,000 g/mol and a molecular weight distribution (Mw/Mn) of less than 5, wherein Mw and Mn are each determined by gel permeation chromatography.

In an embodiment according to the invention one or more processes disclosed herein utilizes a catalyst compound according to one or more embodiments disclosed herein wherein M is Ti; $R^3$ is a $C_1$-$C_{10}$ aliphatic radical; $R^5$ is an aliphatic or alicyclic bulky functional group radical having a molecular size greater than or equal to a molecular size of an isopropyl functional group radical; and each of $R^{10}$ and $R^{12}$ is independently a halogen radical.

In an embodiment according to the invention the polyolefin obtained by a process according to one or more embodiments disclosed herein is an isotactic propylene polymer having a melting point of greater than 145° C. determined by differential scanning calorimetry, which further comprises a meso-pentad [mmmm] content of greater than or equal to about 89%, as determined by $^{13}C$ NMR.

In an embodiment according to the invention the polyolefin obtained by a process according to one or more embodiments disclosed herein is an isotactic propylene polymer having a melting point of greater than 150° C. determined by differential scanning calorimetry, which further comprises a meso-pentad [mmmm] content of greater than or equal to about 95%, as determined by $^{13}C$ NMR.

In an embodiment of the invention the polyolefin obtained by a process according to one or more embodiments disclosed herein is an atactic propylene polymer, which further comprises a weight average molecular weight (Mw) of greater than 100,000 g/mol and a molecular weight distribution (Mw/Mn) of less than 5, wherein Mw and Mn are each determined by gel permeation chromatography.

In an embodiment of the invention, at least one of $R^1$ through $R^{16}$, or at least one of $R^3$, $R^5$, $R^{10}$, and $R^{12}$ is, independently, an electron withdrawing functional group comprising one or more of a nitro group (—$NO_2$), a trihalide group (—$CF_3$, —$CCl_3$, —$CBr_3$, —$CI_3$), a cyano group (—CN), an isocyano group ($R^{\alpha}$CN—), a sulfate group (—$SO_3H$), a carboxylic acid group (—COOH), an aldehyde group (—CHO), a halogen (—F, —Cl, —Br, —I), an ester (—COO$R^{\alpha}$), a ketone (—CO$R^{\alpha}$), and/or an ammonium group (—$NR^{\alpha}_3{}^+$), wherein each $R^{\alpha}$ is independently hydrogen or a $C_1$-$C_{20}$ alkyl radical.

In an embodiment of the invention, at least one of $R^1$ through $R^{16}$ is, independently, a halogen. In an embodiment of the invention, at least one of $R^1$ through $R^{16}$ is independently Cl, Br, or I. In an embodiment of the invention, at least one of $R^3$, $R^5$, $R^{10}$, and $R^{12}$ is independently Br or I. In an embodiment of the invention, each of $R^3$, $R^5$, $R^{10}$, and $R^{12}$ is, independently, Br or I.

In an embodiment of the invention, at least one of $R^1$ through $R^{16}$, or at least one of $R^3$, $R^5$, $R^{10}$, and $R^{12}$ is, independently, a $C_1$-$C_{30}$ aliphatic radical, or a $C_1$-$C_{20}$ aliphatic radical, or a $C_1$-$C_{10}$ aliphatic radical. Suitable examples include methyl, ethyl, propyl, n-butyl, iso-butyl, sec-butyl, tert-butyl, and the like. In an embodiment of the invention, at least one of $R^1$ through $R^{16}$ is, independently, a substituted or unsubstituted $C_1$-$C_{30}$ alicyclic radical, or a substituted or unsubstituted $C_1$-$C_{20}$ alicyclic radical, or a substituted or unsubstituted $C_1$-$C_{10}$ alicyclic radical. Suitable examples include cyclohexane radicals, hexose radicals, and the like.

In an embodiment according to the invention, at least one of $R^1$ through $R^{16}$, or at least one of $R^3$, $R^5$, $R^{10}$, and $R^{12}$ is, independently, a bulky functional group radical having a molecular size greater than or equal to a molecular size of an isopropyl functional group radical. Examples of suitable bulky functional group radicals include substituted and unsubstituted adamantyl radicals, substituted and unsubstituted carbazolyl radicals, and the like. In an embodiment according to the invention, the bulky functional group may be substituted with at least one electron withdrawing functional group.

In an embodiment according to the invention, the Salalen catalyst compound is represented by the formula:

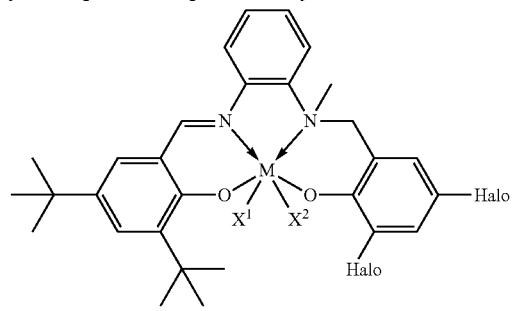

wherein M is Ti, Zr, or Hf; each Halo is independently a halogen, such as Br, Cl, F or I, and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^5$ is tert-butyl, $R^6$ is methyl, and each of $R^{10}$ and $R^{12}$ is independently a halogen, F, Cl, Br, or I.

In an embodiment according to the invention, the Salalen catalyst compound is represented by the formula:

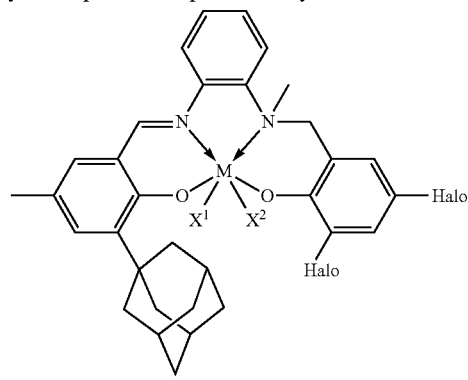

wherein M is Ti, Zr, or Hf; each Halo is independently a halogen, such as Br, Cl, F or I; and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^6$ is methyl, $R^5$ is adamantyl, and each of $R^{10}$ and $R^{12}$ is independently a halogen, F, Cl, Br, or I.

In an embodiment according to the invention, the Salalen catalyst compound is represented by the formula:

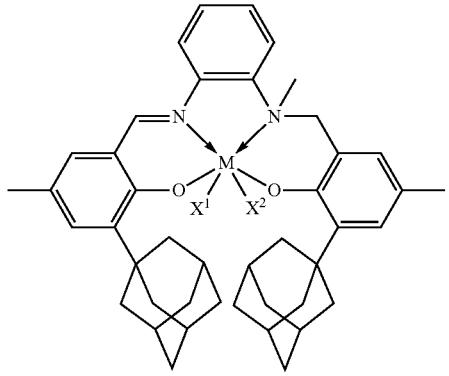

wherein M is Ti, Zr, or Hf; and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^6$, and $R^{10}$ is methyl, and each of $R^5$ and $R^{10}$ is adamantyl.

In an embodiment according to the invention, the Salalen catalyst compound is represented by the formula:

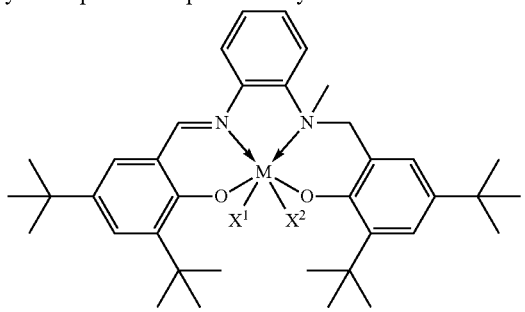

wherein M is Ti, Zr, or Hf; and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^5$, $R^{10}$ and $R^{12}$ is tert-butyl, and $R^6$ is methyl.

In an embodiment according to the invention, the Salalen catalyst compound is represented by the formula:

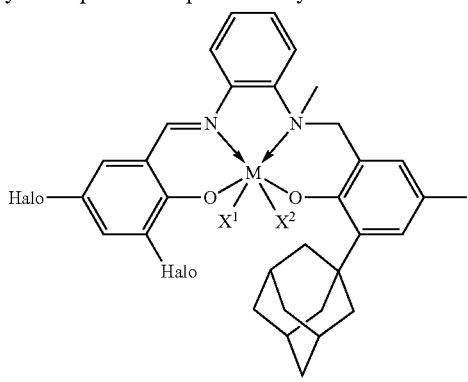

wherein M is Ti, Zr, or Hf; each Halo is independently a halogen, such as Br, Cl, F or I, and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^5$ is independently F, Cl, Br, or I, each of $R^6$ and $R^{10}$ is methyl, and $R^{12}$ is adamantyl.

In an embodiment according to the invention, the Salalen catalyst compound is represented by the formula:

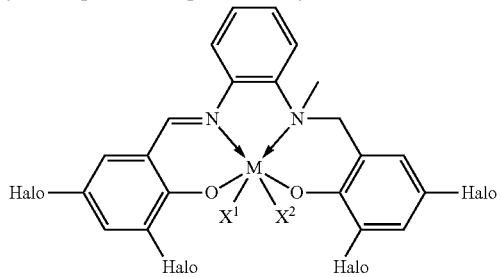

wherein M is Ti, Zr, or Hf; each Halo is independently a halogen, such as Br, Cl, F or I, and each of $X^1$ and $X^2$ is independently halogen or benzyl; i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^5$, $R^{10}$, and $R^{12}$ is independently F, Cl, Br, or I, and $R^6$ is methyl.

In an embodiment according to the invention, the Salalen catalyst compound is represented by the formula:

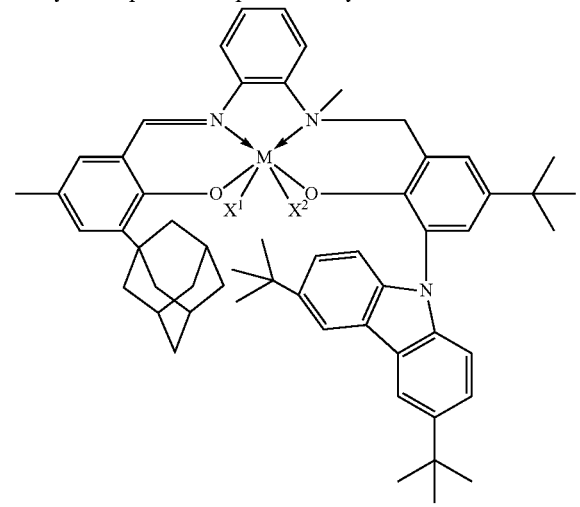

wherein M is Ti, Zr, or Hf and each of $X^1$ and $X^2$ is independently halogen or benzyl, i.e., wherein each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^6$ is methyl, $R^5$ is adamantyl, $R^{10}$ is tert-butyl, and $R^{12}$ is 4,4'-di-tert-butyl carbazolyl.

Methods to Prepare the Catalyst Compounds

In an embodiment according to the invention the phenylene-bridged Salalen ligand precursors may be synthesized by a two-step reaction sequence comprising condensation of the primary amine of N-methyl-1,2-phenylenediamine with a suitably substituted salicylaldehyde, followed by subsequent nucleophilic attack of the secondary amine on a bromomethyl derivative of the corresponding phenol. For example, in an embodiment according to the invention, a 2-((((methylamino)phenyl)imino)methyl)phenol may be prepared via reaction of N-methyl-1,2-phenylenediamine with the appropriately substituted 2-hydroxy-benzaldehyde (a salicylaldehyde) by reflux in an non-polar solvent (Reaction A). The parent Salalen precursor compound may then be prepared via reaction of a 2-halomethyl phenol with a 2-(((methylamino)phenyl)imino)methyl)phenol in the presence of a base (Reaction B). The inventive Salalen catalyst may then be prepared via reaction of the Salalen ligand system (the Salalen precursor) with a tetrasubstituted Group 4 metal (Reaction C).

Reaction A

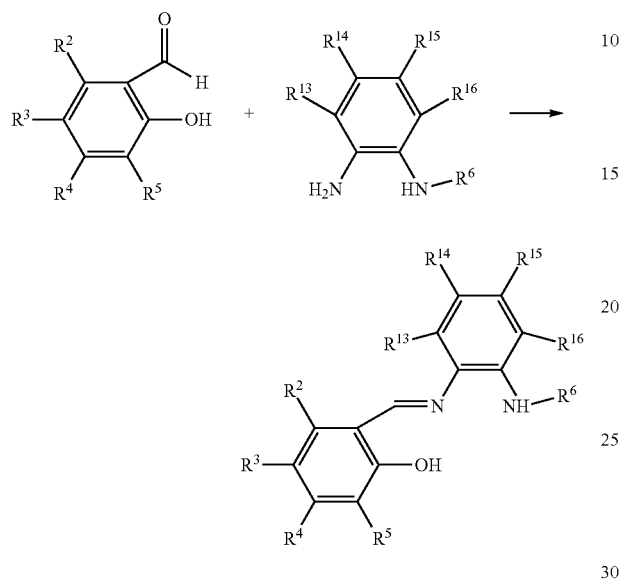

Reaction B

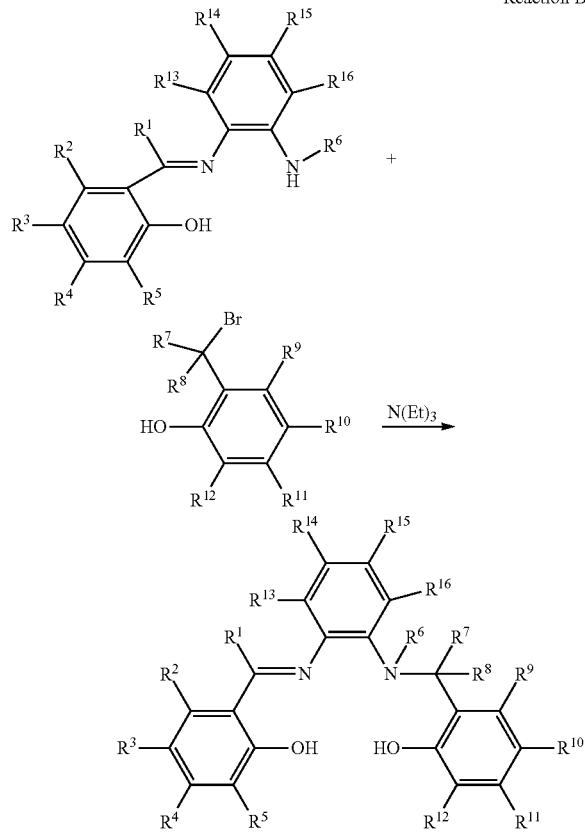

Reaction C

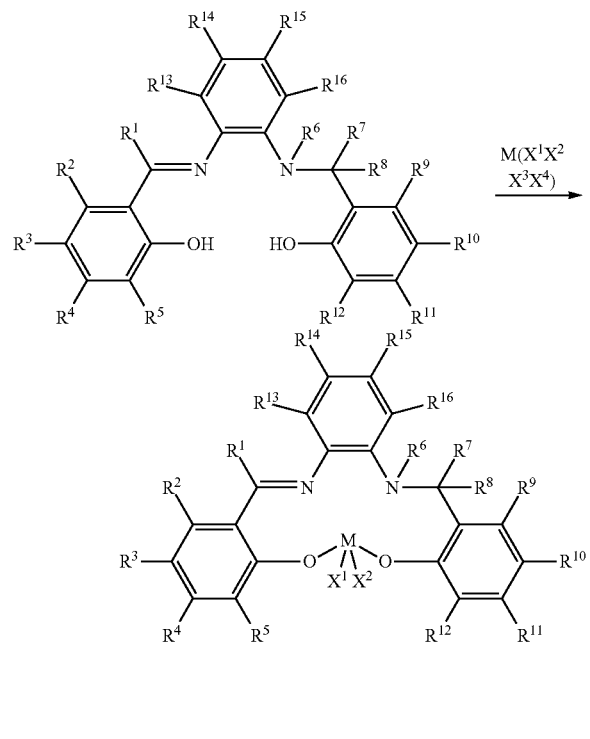

where Et, M, $X^1$, $X^2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ are as defined above, and $X^3$ and $X^4$ are as defined for $X^1$ above.

Activators

The terms "cocatalyst" and "activator" are used interchangeably to describe activators and are defined to be any compound which can activate any one of the catalyst compounds described above by converting the neutral catalyst compound to a catalytically active catalyst compound cation. After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprise a complex as described above and an activator such as alumoxane or a non-coordinating anion. Non-limiting activators, for example, include alumoxanes, aluminum alkyls, ionizing activators, which may be neutral or ionic, and conventional-type cocatalysts. In an embodiment according to the invention, activators may include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Alumoxanes are generally oligomeric compounds containing —Al($R^\alpha$)—O— subunits, where $R^1$ is an alkyl radical. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the catalyst precursor compound comprises an abstractable ligand which is an alkyl, halide, alkoxide or amide. Mixtures of different alumoxanes and modified alumoxanes may also be used. In an embodiment according to the invention, visually clear methylalumoxane may be used. A cloudy or gelled alumoxane can be filtered to produce a clear solution or clear alumoxane can be decanted from the cloudy solution. A useful alumoxane is a modified methyl alumoxane (MMAO) described in U.S. Pat. No. 5,041,584 or commercially available from Akzo Chemicals, Inc. under the trade designation Modified Methylalumoxane type 3A. Solid alumoxanes may also be used.

In an embodiment according to the invention, the activator is a TMA-depleted activator (where TMA is the abbreviation for trimethylaluminum). The inventors have advantageously found that using a TMA-depleted alkyl alumoxane contributes to producing a polymer with higher allyl chain ends. Commercial alumoxanes, such as methylalumoxane (MAO) and isobutylalumoxane, often tend to comprise some residual starting material as an impurity. For example, one common method of making MAO is the hydrolysis of trimethylaluminum (TMA). Such hydrolysis, however, tends to leave residual TMA in the MAO which may have negative effects on polymerization. Any methods known in the art to remove TMA may be used. In an embodiment according to the invention, for example, to produce a TMA-depleted activator, a solution of alumoxane (such as methylalumoxane), for example, 30 wt % in toluene may be diluted in toluene and the aluminum alkyl (such as TMA in the case of MAO) is removed from the solution, for example, by combination with trimethylphenol and filtration of the solid. In an embodiment according to the invention, the TMA-depleted activator comprises from about 1 wt % to about 14 wt % trimethylaluminum, or less than 13 wt % trimethylaluminum, or less than 12 wt % trimethylaluminum, or less than 10 wt % trimethylaluminum, or less than 5 wt % trimethylaluminum, or 0 wt % trimethylaluminum, and/or, greater than 0 wt % trimethylaluminum, or greater than 1 wt % trimethylaluminum.

When the activator is an alumoxane (modified or unmodified), in an embodiment according to the invention, the maximum amount of activator is typically about 5000-fold molar excess Al/M over the catalyst compound (per metal catalytic site). In an embodiment according to the invention, the minimum activator-to-catalyst-compound determined according to molar concentration of the transition metal M is typically about 1 mole aluminum or less to mole of transition metal M. In an embodiment according to the invention, the activator comprises alumoxane and the alumoxane is present at a ratio of 1 mole aluminum or more to mole of catalyst compound. In an embodiment according to the invention, the minimum activator-to-catalyst-compound molar ratio is typically a 1:1 molar ratio. Other examples of Al:M ranges include from 1:1 to 500:1, or from 1:1 to 200:1, or from 1:1 to 100:1, or from 1:1 to 50:1.

Activation may also be performed using non-coordinating anions, referred to as NCA's, of the type described in EP 277 003 A1 and EP 277 004 A1. NCA may be added in the form of an ion pair using, for example, [DMAH]$^+$ [NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as B($C_6F_5$)$_3$, which abstracts an anionic group from the complex to form an activated species. Useful activators include N,N-dimethylanilinium tetrakis(pentafluorophenyl)borate (i.e., [PhNMe$_2$H]B($C_6F_5$)$_4$) and N,N-dimethylanilinium tetrakis(heptafluoronaphthyl)borate, where Ph is phenyl, and Me is methyl.

Additionally, preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately, a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

The term "non-coordinating anion" (NCA) means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis(pentafluorophenyl)borate, a tris perfluorophenyl boron metalloid precursor or a tris perfluoronaphthyl boron metalloid precursor, polyhalogenated heteroborane anions (WO 98/43983), boric acid (U.S. Pat. No. 5,942, 459), or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium, and indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; 5,502,124; and U.S. patent application Ser. No. 08/285,380, filed Aug. 3, 1994; all of which are herein fully incorporated by reference.

Preferred compounds useful as an activator in the process of this invention comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic, diolefinic and acetylenically unsaturated substrates or other neutral Lewis bases, such as ethers, amines, and the like. Two classes of useful compatible non-coordinating anions have been disclosed in EP 0 277 003 A1, and EP 0 277 004 A1: 1) anionic coordination complexes comprising a plurality of lipophilic radicals covalently coordinated to and shielding a central charge-bearing metal or metalloid core; and 2) anions comprising a plurality of boron atoms such as carboranes, metallacarboranes, and boranes.

In a preferred embodiment, the stoichiometric activators include a cation and an anion component, and are preferably represented by the following Formula (I):

$$(Z)_d^+(A^{d-}) \quad (I)$$

wherein Z is (L-H) or a reducible Lewis Acid, L is an neutral Lewis base; H is hydrogen; (L-H)$^+$ is a Bronsted acid; A$^{d-}$ is a non-coordinating anion having the charge d−; and d is an integer from 1 to 3.

When Z is (L-H) such that the cation component is (L-H)$_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation (L-H)$_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid it is preferably represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl. In a preferred embodiment, the reducible Lewis acid is triphenyl carbenium.

The anion component A$^{d-}$ include those having the formula [M$^{k+}$Q$_n$]$^{d-}$ wherein k is 1, 2, or 3; n is 1, 2, 3, 4, 5, or 6, preferably 3, 4, 5 or 6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable A$^{d-}$ components also include diboron compounds as disclosed in U.S. Pat. No. 5,447,895, which is fully incorporated herein by reference.

In a preferred embodiment, this invention relates to a method to polymerize olefins comprising contacting olefins (preferably ethylene and or propylene) with the catalyst compound and a boron containing NCA activator represented by Formula (I) where: Z is (L-H) or a reducible Lewis acid; L is an neutral Lewis base (as further described above); H is hydrogen; (L-H) is a Bronsted acid (as further described above); A$^{d-}$ is a boron containing non-coordinating anion having the charge d− (as further described above); d is 1, 2, or 3.

In a preferred embodiment in any NCA's represented by Formula (I) described above, the reducible Lewis acid is represented by the formula: (Ar$_3$C$^+$), where Ar is aryl or aryl substituted with a heteroatom, a C$_1$ to C$_{40}$ hydrocarbyl, or a substituted C$_1$ to C$_{40}$ hydrocarbyl, preferably the reducible Lewis acid is represented by the formula: (Ph$_3$C$^+$), where Ph is phenyl or phenyl substituted with a heteroatom, a C$_1$ to C$_{40}$ hydrocarbyl, or a substituted C$_1$ to C$_{40}$ hydrocarbyl.

In a preferred embodiment in any of the NCA's represented by Formula (I) described above, Z$_d^+$is represented by the formula: (L-H)$_d^+$, wherein L is an neutral Lewis base; H is hydrogen; (L-H) is a Bronsted acid; and d is 1, 2, or 3, preferably (L-H)$_d^+$is a Bronsted acid selected from ammoniums, oxoniums, phosphoniums, silyliums, and mixtures thereof.

In a preferred embodiment in any of the NCA's represented by Formula (I) described above, the anion component A$^{d-}$ is represented by the formula [M*$^{k*+}$Q*$_{n*}$]$^{d*-}$ wherein k* is 1, 2, or 3; n* is 1, 2, 3, 4, 5, or 6 (preferably 1, 2, 3, or 4); n*−k*=d*; M* is boron; and Q* is independently selected from hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q* having up to 20 carbon atoms with the proviso that in not more than 1 occurrence is Q* a halide.

This invention also relates to a method to polymerize olefins comprising contacting olefins (such as ethylene and or propylene) with the catalyst compound and an NCA activator represented by the following Formula (II):

$$R_nM^{**}(ArNHal)_{4-n} \quad (II)$$

where R is a monoanionic ligand; M** is a Group 13 metal or metalloid; ArNHal is a halogenated, nitrogen-containing aromatic ring, polycyclic aromatic ring, or aromatic ring assembly in which two or more rings (or fused ring systems) are joined directly to one another or together; and n is 0, 1, 2, or 3. Typically the NCA comprising an anion of Formula (II) also comprises a suitable cation that is essentially non-interfering with the ionic catalyst complexes formed with the transition metal compounds, preferably the cation is $Z_d^+$ as described above.

In a preferred embodiment in any of the NCA's comprising an anion represented by Formula (II) described above, R is selected from the group consisting of substituted or unsubstituted $C_1$ to $C_{30}$ hydrocarbyl aliphatic or aromatic groups, where substituted means that at least one hydrogen on a carbon atom is replaced with a hydrocarbyl, halide, halocarbyl, hydrocarbyl or halocarbyl substituted organometalloid, dialkylamido, alkoxy, aryloxy, alkysulfido, arylsulfido, alkylphosphido, arylphosphide, or other anionic substituent; fluoride; bulky alkoxides, where bulky means $C_4$ to $C_{20}$ hydrocarbyl groups; $-SR^1$, $-NR_2^2$, and $-PR_2^3$, where each $R^1$, $R^2$, or $R^3$ is independently a substituted or unsubstituted hydrocarbyl as defined above; or a $C_1$ to $C_{30}$ hydrocarbyl substituted organometalloid.

In a preferred embodiment in any of the NCA's comprising an anion represented by Formula (II) described above, the NCA also comprises cation comprising a reducible Lewis acid represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl, preferably the reducible Lewis acid represented by the formula: $(Ph_3C^+)$, where Ph is phenyl or phenyl substituted with a heteroatom, a $C_1$ to $C_{40}$ hydrocarbyl, or a substituted $C_1$ to $C_{40}$ hydrocarbyl.

In a preferred embodiment in any of the NCA's comprising an anion represented by Formula (II) described above, the NCA also comprises a cation represented by the formula, $(L-H)_d^+$, wherein L is an neutral Lewis base; H is hydrogen; (L-H) is a Bronsted acid; and d is 1, 2, or 3, preferably $(L-H)_d^+$ is a Bronsted acid selected from ammoniums, oxoniums, phosphoniums, silyliums, and mixtures thereof.

Further examples of useful activators include those disclosed in U.S. Pat. Nos. 7,297,653 and 7,799,879.

Another activator useful herein comprises a salt of a cationic oxidizing agent and a noncoordinating, compatible anion represented by the following Formula (III):

$$(OX^{e+})_d(A^{d-})_e \quad \text{(III)}$$

wherein $OX^{e+}$ is a cationic oxidizing agent having a charge of e+; e is 1, 2, or 3; d is 1, 2 or 3; and $A^{d-}$ is a non-coordinating anion having the charge of d– (as further described above). Examples of cationic oxidizing agents include: ferrocenium, hydrocarbyl-substituted ferrocenium, $Ag^+$, or $Pb^{+2}$. Preferred embodiments of $A^{d-}$ include tetrakis(pentafluorophenyl)borate.

In another embodiment, the catalyst compounds can be used with "Bulky activators". A "Bulky activator" as used herein refers to anionic activators represented by the formula:

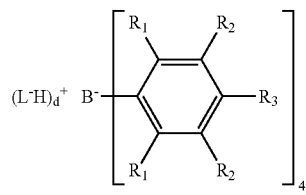

where:

each $R_1$ is, independently, a halide, preferably a fluoride;

each $R_2$ is, independently, a halide, a $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_2$ is a fluoride or a perfluorinated phenyl group);

each $R_3$ is a halide, $C_6$ to $C_{20}$ substituted aromatic hydrocarbyl group or a siloxy group of the formula $-O-Si-R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring);

L is an neutral Lewis base; $(L-H)^+$ is a Bronsted acid; d is 1, 2, or 3;

wherein the anion has a molecular weight of greater than 1020 g/mol; and wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

For purposes of determining the steric bulk of a Bulky activator, the molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula directed to Bulky activators above.

| Activator | Structure of boron substituents | Molecular Formula of each substituent | $V_s$ | MV Per subst. (Å³) | Total MV (Å³) |
|---|---|---|---|---|---|
| Dimethylanilinium tetrakis(perfluoronaphthyl)borate | | $C_{10}F_7$ | 34 | 261 | 1044 |
| Dimethylanilinium tetrakis(perfluorobiphenyl)borate | | $C_{12}F_9$ | 42 | 349 | 1396 |
| [4-tButyl-PhNMe$_2$H] [(C$_6$F$_3$(C$_6$F$_5$)$_2$)$_4$B] | | $C_{18}F_{13}$ | 62 | 515 | 2060 |

Exemplary bulky activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, [4-t-butyl-PhNMe$_2$H][(C$_6$F$_3$(C$_6$F$_5$)$_2$)$_4$B], and the types disclosed in U.S. Pat. No. 7,297,653.

Illustrative, but not limiting, examples of boron compounds which may be used as an activator in the processes of this invention are: N,N-dimethylanilinium tetrakis(perfluorophenyl)borate; methyldioctadecylammonium tetrakis(perfluorophenyl)borate; methyldi(C$_{14-20}$ alkyl)ammonium tetrakis(perfluorophenyl)borate; trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene (diazonium) tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluorophenyl)borate, dimethyl (t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri (n-butyl)ammonium tetrakis(3,5-bis(trifluoromethyl)phenyl)borate, tri(t-butyl)ammonium tetrakis(3,5-bis (trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate,
triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts, such as: di-(i-propyl)ammonium tetrakis(pentafluorophenyl)borate, and dicyclohexylammonium tetrakis(pentafluorophenyl)borate; and additional tri-substituted phosphonium salts, such as tri(o-tolyl)phosphonium tetrakis(pentafluorophenyl) borate, and tri(2,6-dimethylphenyl)phosphonium tetrakis (pentafluorophenyl)borate.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, $[Ph_3C^+][B(C_6F_5)_4^-]$, $[Me_3NH^+][B(C_6F_5)_4^-]$; 1-(4-(tris(pentafluorophenyl)borate)-2,3,5,6-tetrafluorophenyl)pyrrolidinium; tetrakis(pentafluorophenyl)borate, and 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium) tetrakis(pentafluorophenyl)borate, trialkylammonium tetrakis-(2,3,4,6-tetrafluorophenyl)borate, N,N-dialkylanilinium tetrakis-(2,3,4,6-tetrafluorophenyl)borate, trialkylammonium tetrakis (perfluoronaphthyl)borate, N,N-dialkylanilinium tetrakis (perfluoronaphthyl)borate, trialkylammonium tetrakis (perfluorobiphenyl)borate, N,N-dialkylanilinium tetrakis (perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl) phenyl)borate, di-(i-propyl)ammonium tetrakis(pentafluorophenyl)borate, (where alkyl is methyl, ethyl, propyl, n-butyl, sec-butyl, or t-butyl).

Scavengers or Co-Activators

In an embodiment according to the invention, the catalyst system may further include scavengers and/or co-activators. Suitable aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, other oxophilic species such as diethylzinc, and the like may be used. In an embodiment according to the invention, the scavengers and/or co-activators are present at less than 14 wt %, or from 0.1 to 10 wt %, or from 0.5 to 7 wt %, by weight of the catalyst system.

Supports

In an embodiment according to the invention, the catalyst system may comprise an inert support material. In an embodiment according to the invention, the support material comprises a porous support material, for example, talc, and/or inorganic oxides. Other suitable support materials include zeolites, clays, organoclays, or any other organic or inorganic support material and the like, or mixtures thereof.

In an embodiment according to the invention, the support material is an inorganic oxide in a finely divided form. Suitable inorganic oxide materials for use in catalyst systems herein include Groups 2, 4, 13, and 14 metal oxides, such as silica, alumina, and mixtures thereof. Other inorganic oxides that may be employed either alone or in combination with the silica, and/or alumina include magnesia, titania, zirconia, montmorillonite, phyllosilicate, and/or the like, as well as combinations of these support materials including silica-chromium, silica-alumina, silica-titania, and the like. In an embodiment according to the invention, the support materials include $Al_2O_3$, $ZrO_2$, $SiO_2$, $SiO_2/Al_2O_3$, and combinations thereof. Other suitable support materials include finely divided functionalized polyolefins, such as finely divided polyethylene.

In an embodiment according to the invention, the support material may have a surface area in the range of from about 10 to about 700 $m^2/g$, pore volume in the range of from about 0.1 to about 4.0 cc/g and average particle size in the range of from about 5 to about 500 μm, or the surface area of the support material is in the range of from about 50 to about 500 $m^2/g$, pore volume of from about 0.5 to about 3.5 cc/g and average particle size of from about 10 to about 200 μm. In an embodiment according to the invention, a majority portion of the surface area of the support material is in the range is from about 100 to about 400 $m^2/g$, pore volume from about 0.8 to about 3.0 cc/g and average particle size is from about 5 to about 100 μm. In an embodiment according to the invention, the average pore size of the support material is in the range of from 10 to 1000 Å, or 50 to about 500 Å, or 75 to about 350 Å. In an embodiment according to the invention, the support material is a high surface area, amorphous silica having a surface area greater than or equal to about 300 $m^2/g$, and/or a pore volume greater than or equal to about 1.65 $cm^3/gm$. Suitable silicas are marketed under the trade names of Davison 952 or Davison 955 by the Davison Chemical Division of W.R. Grace and Company. In an embodiment according to the invention, the support may comprise Davison 948.

In an embodiment according to the invention, the support material should be essentially dry, that is, essentially free of absorbed water. Drying of the support material can be effected by heating or calcining at about 100° C. to about 1000° C., or at a temperature of at least about 400° C., or 500° C., or 600° C. When the support material is silica, it is heated to at least 200° C., or about 200° C. to about 850° C., or at least 600° C. for a time of about 1 minute to about 100 hours, or from about 12 hours to about 72 hours, or from about 24 hours to about 60 hours. In an embodiment according to the invention, the calcined support material must have at least some reactive hydroxyl (OH) groups to produce supported catalyst systems according to the instant disclosure.

In an embodiment according to the invention, the calcined support material is contacted with at least one polymerization catalyst comprising at least one catalyst compound and an activator. In an embodiment according to the invention, the support material, having reactive surface groups, typically hydroxyl groups, is slurried in a non-polar solvent and the resulting slurry is contacted with a solution of a catalyst compound and an activator. In an embodiment according to the invention, the slurry of the support material is first contacted with the activator for a period of time in the range of from about 0.5 hours to about 24 hours, or from about 2 hours to about 16 hours, or from about 4 hours to about 8 hours. The solution of the catalyst compound is then contacted with the isolated support/activator. In an embodiment according to the invention, the supported catalyst system is generated in situ. In alternate embodiment, the slurry of the support material is first contacted with the catalyst compound for a period of time in the range of from about 0.5 hours to about 24 hours, or from about 2 hours to about 16 hours, or from about 4 hours to about 8 hours. The slurry of the supported catalyst compound is then contacted with the activator solution.

In an embodiment according to the invention, the mixture of the catalyst, activator and support is heated to about 0° C. to about 70° C., or to about 23° C. to about 60° C., or to room temperature. Contact times typically range from about 0.5 hours to about 24 hours, or from about 2 hours to about 16 hours, or from about 4 hours to about 8 hours.

Suitable non-polar solvents are materials in which all of the reactants used herein, i.e., the activator and the catalyst compound are at least partially soluble and which are liquid at reaction temperatures. Suitable non-polar solvents include alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

In an embodiment according to the invention, the activator, the catalyst compound, or a combination thereof is supported by contacting the activator, the catalyst compound, or both with a support to form a supported activator, supported catalyst, or a combination thereof, wherein the activator, the catalyst compound, or a combination thereof are deposited on, vaporized with, bonded to, incorporated within, adsorbed or absorbed in, or on the support.

In an embodiment according to the invention, the catalyst compounds, activators and/or catalyst systems disclosed herein may be combined with one or more support materials or carriers. For example, in an embodiment according to the invention, the activator is contacted with a support to form a supported activator wherein the activator is deposited on, contacted with, vaporized with, bonded to, or incorporated within, adsorbed or absorbed in, or on, a support or carrier.

In an embodiment according to the invention, the catalyst, the activator, or a combination thereof may be supported using "incipient wetness", wherein a solution comprising the activator, the catalyst compound, or a combination thereof is contacted with the support wherein the amount of the solution is about 95 to about 100 percent of the absorptive capacity of the support material.

In an embodiment according to the invention, the support material is chemically treated and/or dehydrated prior to combining with the catalyst compound, activator and/or catalyst system. In an embodiment according to the invention, the support material may have various levels of dehydration, such as may be achieved by drying the support material at temperatures in the range from about 200° C. to about 1000° C. These supports may also be chemically dehydrated using water reactive compounds such as silane and organoaluminum compounds.

In an embodiment according to the invention, dehydrated silica may be contacted with an organoaluminum or alumoxane compound. In an embodiment according to the invention, wherein an organoaluminum compound is used, the activator is formed in situ in the support material as a result of the reaction of, for example, trimethylaluminum and water.

In an embodiment according to the invention, Lewis base-containing support substrates will react with a Lewis acidic activator to form a support bonded Lewis acid compound. The Lewis base hydroxyl groups of silica are exemplary of metal/metalloid oxides where this method of bonding to a support occurs. These embodiments are described in, for example, U.S. Pat. No. 6,147,173.

Other embodiments of supporting an activator are described in U.S. Pat. No. 5,427,991, where supported non-coordinating anions derived from trisperfluorophenyl boron are described; U.S. Pat. No. 5,643,847, discusses the reaction of Group 13 Lewis acid compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions.

In an embodiment according to the invention, the supported activator is formed by preparing, in an agitated, temperature and pressure controlled vessel, a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40 to 120° C. and pressures from 34.5 kPa to 138 kPa (5 psia to 20 psia). An inert gas sweep can also be used in assist in removing solvent. Alternate orders of addition, such as slurrying the support material in an appropriate solvent then adding the activator, can be used.

In an embodiment according to the invention, the weight percent of the activator to the support material is in the range from about 10 weight percent to about 70 weight percent, in the range from about 20 weight percent to about 60 weight percent in other embodiments, in the range from about 30 weight percent to about 50 weight percent in other embodiments, and in the range from about 30 weight percent to about 40 weight percent in yet other embodiments.

Supported catalysts system useful in embodiments disclosed herein include those supported catalyst systems that are formed by contacting a support material, an activator and a catalyst compound in various ways under a variety of conditions outside of a catalyst feeder apparatus.

In an embodiment according to the invention, a catalyst compound, activator and support, may be fed into the polymerization reactor as a mineral oil slurry or as a slurry in liquid diluent. Solids concentrations in the mineral oil or liquid diluent may range from about 3 to about 30 weight percent in some embodiments; and from about 10 to about 25 weight percent in other embodiments.

In an embodiment according to the invention, the catalyst compound(s), activator(s) and/or support(s) used herein may also be spray dried separately or together prior to being injected into the reactor. The spray dried catalyst may be used as a powder or solid or may be placed in a diluent and slurried into the reactor. In an embodiment according to the invention, a support is combined with one or more activators and is spray dried to form a supported activator. In an embodiment according to the invention, fumed silica is combined with methyl alumoxane and then spray dried to from supported methyl alumoxane, a support may be combined with alumoxane, spray dried and then placed in mineral oil to form a slurry useful according to the instant disclosure. In an embodiment according to the invention, the catalyst compounds described above may be combined with one or more support material(s) and/or one or more activator(s) and spray dried prior to being combined with a slurry diluent.

In an embodiment according to the invention, the catalyst compounds and/or the activators are combined with a support material such as a particulate filler material and then spray dried, which may form a free flowing powder. Spray drying may be by any means known in the art. In an embodiment according to the invention, the catalyst may be spray dried by placing the catalyst compound and the activator in solution, allowing the catalyst compound and activator to react, if desired, adding a filler material such as silica and/or fumed silica, then forcing the solution at high pressures through a nozzle. The solution may be sprayed onto a surface or sprayed such that the droplets dry in midair. The method generally employed is to disperse the silica in toluene, stir in the activator solution, and then stir in the catalyst compound solution. Slurry concentrations may be about 5 to 8 wt %. This formulation may sit as a slurry for as long as 30 minutes with mild stirring or manual shaking to keep it as a suspension before spray-drying. In an embodiment according to the invention, the makeup of the dried material is about 40-50 wt % activator (e.g., alumoxane), 50-60 $SiO_2$ and about 2 wt % catalyst compound.

In an embodiment according to the invention, two or more catalyst compounds can be added together in the desired ratio in the last step. In another embodiment, more complex procedures are possible, such as addition of a first catalyst compound to the activator/filler mixture for a specified reaction time t, followed by the addition of the second catalyst compound solution, mixed for another specified time x, after which the mixture is cosprayed. Lastly, another additive, such as 1-hexene in about 10 vol % can be present in the activator/filler mixture prior to the addition of the first catalyst compound.

In an embodiment according to the invention, binders are added to the mix. These can be added as a means of improving the particle morphology, i.e. narrowing the particle size distribution, lower porosity of the particles and allowing for a reduced quantity of alumoxane, which is acting as the "binder".

In an embodiment according to the invention, spray dried particles are fed into the polymerization reactor as a mineral oil slurry. Solids concentrations in oil are about 10 to 30 wt %, or 15 to 25 wt %. In an embodiment according to the invention, the spray dried particles can be from less than about 10 micrometers in size up to about 100 micrometers, compared to conventional supported catalysts which are about 50 micrometers. In an embodiment according to the invention, the support has an average particle size of 1 to 50 microns, or 10 to 40 microns.

In an embodiment according to the invention, a catalyst composition according to the instant disclosure is utilized in a catalyst component slurry and/or in a catalyst component solution. For the purposes of the instant disclosure, a slurry is defined to be a suspension of a solid, where the solid may or may not be porous, in a liquid. The catalyst component slurry and the catalyst component solution are combined to form the catalyst composition which is then introduced into a polymerization reactor. In an embodiment according to the invention, the catalyst component slurry includes an activator and a support, or a supported activator. In an embodiment according to the invention, the slurry also includes a catalyst compound in addition to the activator and the support and/or the supported activator. In an embodiment according to the invention, the catalyst compound in the slurry is supported. In an embodiment according to the invention, the slurry includes one or more activator(s) and support(s) and/or supported activator(s) and/or one more catalyst compound(s). For example, the slurry may include two or more activators (such as a supported alumoxane and a modified alumoxane) and a catalyst compound, or the slurry may include a supported activator and more than one catalyst compounds. In an embodiment according to the invention, the slurry comprises a supported activator and two catalyst compounds.

In an embodiment according to the invention, the slurry comprises supported activator and two different catalyst compounds, which may be added to the slurry separately or in combination. In an embodiment according to the invention, the slurry, containing a supported alumoxane, is contacted with a catalyst compound, allowed to react, and thereafter the slurry is contacted with another catalyst compound. In another embodiment the slurry containing a supported alumoxane is contacted with two catalyst compounds at the same time, and allowed to react. In an embodiment according to the invention, the molar ratio of metal in the activator to metal in the catalyst compound in the slurry is 1000:1 to 0.5:1, or 300:1 to 1:1, or 150:1 to 1:1.

Polymerization Processes

In an embodiment according to the invention, a polymerization process includes contacting monomers (such as ethylene and propylene), and optionally comonomers, with a catalyst system comprising an activator and at least one catalyst compound, as described above at a temperature, a pressure, and for a period of time sufficient to produce a polyolefin. In an embodiment according to the invention, the catalyst compound and activator may be combined in any order, and may be combined prior to contacting with the monomer. In an embodiment according to the invention, the catalyst compound and/or the activator are combined after contacting with the monomer.

In an embodiment according to the invention, two or more different catalyst compounds are present in the catalyst system used herein. In an embodiment according to the invention, two or more different catalyst compounds are present in the reaction zone where the process or processes described herein occur. When two transition metal compound based catalysts are used in one reactor as a mixed catalyst system, the two transition metal compounds are chosen such that the two are compatible. Compatible catalysts are those catalysts having similar kinetics of termination and insertion of monomer and comonomer(s) and/or do not detrimentally interact with each other. For purposes herein, the term "incompatible catalysts" refers to and means catalysts that satisfy one or more of the following: 1) those catalysts that when present together reduce the activity of at least one of the catalysts by greater than 50%; 2) those catalysts that under the same reactive conditions produce polymers such that one of the polymers has a molecular weight that is more than twice the molecular weight of the other polymer; and 3) those catalysts that differ in comonomer incorporation or reactivity ratio under the same conditions by more than about 30%. A simple screening method such as by $^1$H or $^{13}$C NMR, known to those of ordinary skill in the art, can be used to determine which transition metal compounds are compatible. In an embodiment according to the invention, the catalyst systems use the same activator for the catalyst compounds. In an embodiment according to the invention, two or more different activators, such as a non-coordinating anion activator and an alumoxane, can be used in combination. If one or more catalyst compounds contain an $X^1$ or $X^2$ ligand which is not a hydride, or a hydrocarbyl, then in an embodiment according to the invention, the alumoxane is contacted with the catalyst compounds prior to addition of the non-coordinating anion activator.

In an embodiment according to the invention, when two transition metal compounds (pre-catalysts) are utilized, they may be used in any ratio. In an embodiment according to the invention, a molar ratio of a first transition metal compound (A) to a second transition metal compound (B) will fall within the range of (A:B) 1:1000 to 1000:1, or 1:100 to 500:1, or 1:10 to 200:1, or 1:1 to 100:1, or 1:1 to 75:1, or 5:1 to 50:1. The particular ratio chosen will depend on the exact pre-catalysts chosen, the method of activation, and the end product desired. In an embodiment according to the invention, when using two pre-catalysts, where both are activated with the same activator, a useful mole percent, based upon the total moles of the pre-catalysts, are 10:90 to 0.1:99, or 25:75 to 99:1, or 50:50 to 99.5:0.5, or 50:50 to 99:1, or 75:25 to 99:1, or 90:10 to 99:1.

Monomers useful herein include substituted or unsubstituted $C_2$ to $C_{40}$ alpha olefins, or $C_2$ to $C_{20}$ alpha olefins, or $C_2$ to $C_{12}$ alpha olefins, or ethylene, propylene, butene, pentene, hexene, heptene, octene, nonene, decene, undecene, dodecene and isomers thereof. In an embodiment according to the invention, the monomer comprises propylene and an optional comonomer(s) comprising one or more ethylene or $C_4$ to $C_{40}$ olefins, or $C_4$ to $C_{20}$ olefins, or $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In an embodiment according to the invention, the monomer comprises ethylene or ethylene and a comonomer comprising one or more $C_3$ to $C_{40}$ olefins, or $C_4$ to $C_{20}$ olefins, or $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, or hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, or norbornene, norbornadiene, and dicyclopentadiene.

In an embodiment according to the invention, one or more dienes are present in the polymer produced herein at up to 10 weight %, or at 0.00001 to 1.0 weight %, or 0.002 to 0.5 weight %, or 0.003 to 0.2 weight %, based upon the total weight of the composition. In an embodiment according to the invention, 500 ppm or less of diene is added to the polymerization, or 400 ppm or less, or 300 ppm or less. In an embodiment according to the invention, at least 50 ppm of diene is added to the polymerization, or 100 ppm or more, or 150 ppm or more.

Diolefin monomers useful in this invention include any hydrocarbon structure, or $C_4$ to $C_{30}$, having at least two unsaturated bonds, wherein at least two of the unsaturated bonds are readily incorporated into a polymer by either a stereospecific or a non-stereospecific catalyst(s). In an embodiment according to the invention, the diolefin monomers may be selected from alpha, omega-diene monomers (i.e. di-vinyl monomers). Preferably, the diolefin monomers are linear divinyl monomers, most or those containing from 4 to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

In an embodiment according to the invention, where butene is the comonomer, the butene source may be a mixed butene stream comprising various isomers of butene. The 1-butene monomers are expected to be preferentially consumed by the polymerization process. Use of such mixed butene streams will provide an economic benefit, as these mixed streams are often waste streams from refining processes, for example, $C_4$ raffinate streams, and can therefore be substantially less expensive than pure 1-butene.

Polymerization processes according to the instant disclosure may be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are suitable for use herein; wherein a homogeneous polymerization process is defined to be a process where at least 90 wt % of the product is soluble in the reaction media. A bulk homogeneous process is suitable for use herein, wherein a bulk process is defined to be a process where monomer concentration in all feeds to the reactor is 70 volume % or more. In an embodiment according to the invention, no solvent or diluent is present or added in the reaction medium, (except for the small amounts used as the carrier for the catalyst system or other additives, or amounts typically found with the monomer; e.g., propane in propylene). In an embodiment according to the invention, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkyl substituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In an embodiment according to the invention, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In an embodiment according to the invention, the solvent is not aromatic, or aromatics are present in the solvent at less than 1 wt %, or less than 0.5 wt %, or less than 0.0 wt % based upon the weight of the solvents.

In an embodiment according to the invention, the feed concentration of the monomers and comonomers for the polymerization is 60 vol % solvent or less, or 40 vol % or less, or 20 vol % or less, based on the total volume of the feedstream. The polymerization may also be run in a bulk process.

Polymerizations can be run at any temperature and/or pressure suitable to obtain the desired ethylene polymers. Suitable temperatures and/or pressures include a temperature in the range of from about 0° C. to about 300° C., or from about 20° C. to about 200° C., or from about 35° C. to about 150° C., or from about 50° C. to about 150° C., or from about 40° C. to about 120° C., or from about 45° C. to about 80° C.; and a pressure in the range of from about 0.35 MPa to about 10 MPa, or from about 0.45 MPa to about 6 MPa, or from about 0.5 MPa to about 4 MPa.

In an embodiment according to the invention, the run time of the reaction is from about 0.1 minutes to about 24 hours, or up to 16 hours, or in the range of from about 5 to 250 minutes, or from about 10 to 120 minutes.

In an embodiment according to the invention, hydrogen is present in the polymerization reactor at a partial pressure of 0.007 kPa to 345 kPa (0.001 to 50 psig), or from 0.07 kPa to 172 kPa (0.01 to 25 psig), or 0.7 kPa to 70 kPa (0.1 to 10 psig).

In an embodiment according to the invention, the activity of the catalyst is at least 50 g/mmol/hour, or 500 or more g/mmol/hour, or 5000 or more g/mmol/hr, or 50,000 or more g/mmol/hr. In an alternate embodiment, the conversion of olefin monomer is at least 10%, based upon polymer yield and the weight of the monomer entering the reaction zone, or 20% or more, or 30% or more, or 50% or more, or 80% or more.

In an embodiment according to the invention, the polymerization conditions include one or more of the following:

1) temperatures of 0 to 300° C. (or 25 to 150° C., or 40 to 120° C., or 45 to 80° C.);

2) a pressure of atmospheric pressure to 10 MPa (or 0.35 to 10 MPa, or from 0.45 to 6 MPa, or from 0.5 to 4 MPa);

3) the presence of an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; or where aromatics are or present in the solvent at less than 1 wt %, or less than 0.5 wt %, or at 0 wt % based upon the weight of the solvents);

4) the polymerization occurs in one reaction zone;

5) the productivity of the catalyst compound is at least 80,000 g/mmol/hr (or at least 150,000 g/mmol/hr, or at least 200,000 g/mmol/hr, or at least 250,000 g/mmol/hr, or at least 300,000 g/mmol/hr);

6) scavengers (such as trialkyl aluminum compounds) are absent (e.g., present at zero mol %) or the scavenger is present at a molar ratio of scavenger to transition metal of less than 100:1, or less than 50:1, or less than 15:1, or less than 10:1; or equal to or less than about 8:1;

8) optionally hydrogen is present in the polymerization reactor at a partial pressure of 0.007 to 345 kPa (0.001 to 50 psig) (or from 0.07 to 172 kPa (0.01 to 25 psig), or 0.7 to 70 kPa (0.1 to 10 psig)).

In an embodiment according to the invention, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In an embodiment according to the invention, the polymerization occurs in one reaction zone.

In an embodiment according to the invention, a zirconium or a hafnium based phenylene bridged Salalen catalyst according to one or more embodiments disclosed herein may be employed to produce a highly isotactic polypropylene polymer. However, in an embodiment according to the invention, this same Salalen catalyst according to one or more embodiments disclosed herein, when coordinated with titanium, may be employed to produce an atactic polypropylene polymer.

In an embodiment according to the invention, a process to produce an atactic polypropylene polymer comprises contacting one or more olefins with a catalyst system comprising a titanium based phenylene bridged Salalen catalyst according to one or more embodiments disclosed herein at a temperature, a pressure, and for a period of time sufficient to produce a polypropylene polymer, wherein the catalyst comprises a phenylene Salalen ligand system according to one or more embodiments disclosed herein selected for being a phenylene bridged Salalen ligand system according to one or more embodiments disclosed herein which is useful to produce a highly isotactic polypropylene polymer when coordinated with hafnium or zirconium.

Polyolefin Products

The instant disclosure also relates to compositions of matter produced by the methods described herein.

In an embodiment according to the invention, the process described herein produces propylene homopolymers or propylene copolymers, such as propylene-ethylene and/or propylene-α-olefin (or $C_3$ to $C_{20}$) copolymers (such as propylene-hexene copolymers or propylene-octene copolymers) having a Mw/Mn of less than 10, or less than 9, or less than 8, or less than 7, or less than 6, or less than 5, or less than 4, or less than 3, or less than 2, or less than 9 and greater than 1, or less than or equal to about 6 and greater than 1, or less than 5 and greater than 2, or less than 4 and greater than 3, determined by gel permeation chromatography.

Likewise, the process according to an embodiment of the invention produces olefin polymers, or polyethylene and polypropylene homopolymers and copolymers. In an embodiment according to the invention, the polymers produced herein are homopolymers of ethylene or propylene, are copolymers of ethylene or having from 0 to 25 mole % (or from 0.5 to 20 mole %, or from 1 to 15 mole %, or from 3 to 10 mole %) of one or more $C_3$ to $C_{20}$ olefin comonomer (or $C_3$ to $C_{12}$ alpha-olefin, or propylene, butene, hexene, octene, decene, dodecene, or propylene, butene, hexene, octene), or are copolymers of propylene or having from 0 to 25 mole % (or from 0.5 to 20 mole %, or from 1 to 15 mole %, or from 3 to 10 mole %) of one or more of $C_2$ or $C_4$ to $C_{20}$ olefin comonomer (or ethylene or $C_4$ to $C_{12}$ alpha-olefin, or ethylene, butene, hexene, octene, decene, dodecene, or ethylene, butene, hexene, octene).

In an embodiment according to the invention, the monomer is ethylene and the comonomer is hexene, or from 1 to 15 mole % hexene, or 1 to 10 mole % hexene.

In an embodiment according to the invention, the polymers produced herein have an Mw of at least 20,000 g/mol, or 25,000 g/mol, or 30,000 g/mol, or 35,000 g/mol. In an embodiment according to the invention, the polymers produced herein have an Mw of at least 100,000 g/mol, or 130,000 g/mol, or 200,000 g/mol, or 300,000 g/mol, or 400,000 g/mol and/or an Mw/Mn of greater than 1 to 20, or 2 to 10, or 2 to 9, or 2 to 6, or 3 to 5, or 3 to 4.

In an embodiment according to the invention, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

In an embodiment according to the invention, the polyolefins produced using the instant catalyst may be isotactic, highly isotactic, syndiotactic, or highly syndiotactic propylene polymer. In a desirable embodiment, the polyolefin (preferably polypropylene) has at least 85% isotacticity, or at least 90% isotacticity, or at least 95% isotacticity.

In an embodiment according to the invention, the polymer produced herein has a composition distribution breadth index (CDBI) of 50% or more, or 60% or more, or 70% or more. CDBI is a measure of the composition distribution of monomer within the polymer chains and is measured by the procedure described in PCT publication WO 93/03093, published Feb. 18, 1993, specifically columns 7 and 8 as well as in Wild et al, J. Poly. Sci., Poly. Phys. Ed., Vol. 20, p. 441 (1982) and U.S. Pat. No. 5,008,204, including that fractions having a weight average molecular weight (Mw) below 15,000 are ignored when determining CDBI.

Polymers with an Mw/Mn of 4.5 or less may include a significant level of long chain branching. The long chain branching is understood to be the result of the incorporation of terminally unsaturated polymer chains (formed by the specific termination reaction mechanism encountered with single site catalysts) into other polymer chains in a manner analogous to monomer incorporation. The branches are hence believed to be linear in structure and may be present at a level where no peaks can be specifically attributed to such long chain branches in the $^{13}C$ NMR spectrum. In an embodiment according to the invention, the polymers produced according to the instant disclosure comprise a significant amount of long chain branching, defined as having a ratio of long chain branching of at least 7 carbons per 1000 carbon atoms as determined according to the $^{13}C$ NMR spectrum of greater than 0.5. In an embodiment according to the invention, the ratio of long chain branching with branches having at least 7 carbons, per 1000 carbon atoms as determined according to the $^{13}C$ NMR spectrum is greater than 1, or greater than 1.5, or greater than 2.

In an embodiment according to the invention, the polymers produced according to the instant disclosure include a significant amount of vinyl termination, defined as a ratio of vinyl groups per molecule of greater than or equal to 0.2. In an embodiment according to the invention, the polymers according to the instant disclosure comprise a ratio of vinyl groups per molecule of greater than or equal to 0.5, or 0.7, or 0.8, or 0.9, or 0.95, when determined according to the description provided herein.

In an embodiment according to the invention, propylene polymer produced using the instant catalyst comprise at least 50% vinyl or unsaturated chain ends. In an embodiment of the invention, at least 90%, or at least 95%, or at least 99% vinylidene chain ends.

This invention relates to polymers having both vinyl termination and long chain branching, which in an embodiment according to the invention, are produced by the processes and using the catalyst disclosed herein. In an embodiment according to the invention, the process described herein produces polymers having:

a) at least 50% allyl chain ends, or least 60%, 70%, 80%, 90%, 95%, 98%, or 99%; and/or b) an Mn of at least 200 g/mol, or 250 g/mol to 100,000 g/mol, e.g., or 200 g/mol to 75,000 g/mol, e.g., or 200 g/mol to 60,000 g/mol, or 300 g/mol to 60,000 g/mol, or 750 g/mol to 30,000 g/mol) as determined by GPC; and/or c) at least 0.5 branches having 7 or more carbon atoms per 1000 carbon atoms, or 1.0 or more, or 1.25 or more, or 1.5 or more, or 1.75 or more, or 2.0 or more, or from 0.5 to 5.0, or from 1.0 to 4.0, or from 1.5 to 3.0; and/or d) a Tm of 100° C. or more, or 110° C. or more, or 120° C. or more; and/or e) a ratio of methyl chain ends, also referred to herein as saturated chain ends, to allyl chain ends of 1:1 to 5:1, or 1:1 to 4:1, or 1:1 to 3:1; and/or f) at least 50 wt % of the polymer, which may be an ethylene homopolymer or copolymer, has one vinyl per molecule or per chain as determined by $^1$H NMR or $^{13}$C NMR, or at least 60 wt %, or at least 70 wt %, or at least 80 wt %, or at least 90 wt %, or at least 95 wt %; and/or essentially no diene is present, or the polymer comprises less than or equal to about 0.01 wt % diene; and/or g) the polymer comprises at least 50 mol % ethylene, or at least 60 mol %, or at least 70 mol %, or at least 75 mol %, or at least 80 mol %, or at least 85 mol %, or at least 90 mol %, or at least 95 mol %, or essentially 100 mol % ethylene; and/or h) an Mw/Mn as determined by GPC of greater than 1 to 4, or greater than 1 to 3.

In an embodiment according to the invention, polymer produced herein has less than 1400 ppm aluminum, or less than 1200 ppm, or less than 1000 ppm, or less than 500 ppm, or less than 100 ppm as determined by ICPES (Inductively Coupled Plasma Emission Spectrometry), which is described in J. W. Olesik, "Inductively Coupled Plasma-Optical Emission Spectroscopy," in the Encyclopedia of Materials Characterization, C. R. Brundle, C. A. Evans, Jr. and S. Wilson, eds., Butterworth-Heinemann, Boston, Mass., 1992, pp. 633-644, which is used herein for purposes of determining the amount of an element in a material; and/or in an embodiment according to the invention, the polymer has less than 1400 ppm of the Group 3, 4, 5, or 6 transition metal, or of the Group 4 transition metal, or of Ti, Zr, and/or Hf, or less than 1200 ppm, or less than 1000 ppm, or less than 500 ppm, or less than 100 ppm, as determined by ICPES as discussed above.

In an embodiment according to the invention, an ethylene polymer according to the instant disclosure has less than 1400 ppm hafnium, or less than 1200 ppm, or less than 1000 ppm, or less than 500 ppm, or less than 100 ppm as determined by ICPES.

In an embodiment according to the invention, an ethylene polymer according to the instant disclosure has less than 1400 ppm zirconium, or less than 1200 ppm, or less than 1000 ppm, or less than 500 ppm, or less than 100 ppm as determined by ICPES.

In an embodiment according to the invention, the polymer produced herein, which may be an ethylene polymer, has a density of greater than 0.95 g/cc, or greater than 0.955 g/cc, or greater than 0.96 g/cc.

In an embodiment according to the invention, the polymer produced herein has a branching index (g'vis) of 0.9 or less, or 0.85 or less, or 0.80 or less, where g'vis is determined as described below.

Blends:

In an embodiment according to the invention, the polymer (or the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene and/or butene and/or hexene, polybutene, ethylene vinyl acetate copolymer, LDPE, LLDPE, HDPE, ethylene methyl acrylate copolymer, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, ethylene-vinyl alcohol copolymers (EVOH), polymers of aromatic monomers such as polystyrene, poly-1 esters, polyacetal, polyvinylidine fluoride, polyethylene glycols, and/or polyisobutylene.

In an embodiment according to the invention, the polymer (or the polyethylene or polypropylene) is present in the above blends, at from 10 to 99 wt %, based upon the weight of the polymers in the blend, or 20 to 95 wt %, or at least 30 to 90 wt %, or at least 40 to 90 wt %, or at least 50 to 90 wt %, or at least 60 to 90 wt %, or at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX 1010 or IRGANOX 1076 available from Ciba-Geigy); phosphites (e.g., IRGAFOS 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films:

In an embodiment according to the invention, any of the foregoing polymers, such as the foregoing polypropylenes or blends thereof, may be used in a variety of end-use applications. Applications include, for example, mono- or multilayer blown, extruded, and/or shrink films. These films may be formed by any number of well-known extrusion or coextrusion techniques, such as a blown bubble film processing technique, wherein the composition can be extruded in a molten state through an annular die and then expanded to form a uniaxial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxial orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the machine direction (MD) at a ratio of up to 15, or between 5 and 7, and in the transverse direction (TD) at a ratio of up to 15, or 7 to 9. However, in an embodiment according to the invention, the film is oriented to the same extent in both the MD and TD directions.

The films may vary in thickness depending on the intended application; however, films of a thickness from 1 to 50 µm are usually suitable. Films intended for packaging are usually from 10 to 50 µm thick. The thickness of the sealing layer is typically 0.2 to 50 µm. There may be a sealing layer on both the inner and outer surfaces of the film or the sealing layer may be present on only the inner or the outer surface.

In an embodiment according to the invention, one or more layers may be modified by corona treatment, electron beam irradiation, gamma irradiation, flame treatment, or microwave. In an embodiment according to the invention, one or both of the surface layers is modified by corona treatment.

Molded Products:

The compositions described herein may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

Further, the compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. Typically, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The tool stays closed to cool the film and the tool is then opened. The shaped laminate is then removed from the tool. The thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution.

Blow molding is another suitable forming means for use with the compositions of this invention, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley $^2$ Sons 1990).

Likewise, molded articles may be fabricated by injecting molten polymer into a mold that shapes and solidifies the molten polymer into desirable geometry and thickness of molded articles. Sheets may be made either by extruding a substantially flat profile from a die, onto a chill roll, or by calendaring. Sheets are generally considered to have a thickness of from 254 µm to 2540 µm (10 mils to 100 mils), although any given sheet may be substantially thicker.

Non-Wovens and Fibers:

The polyolefin compositions described above may also be used to prepare nonwoven fabrics and fibers of this invention in any nonwoven fabric and fiber making process, including but not limited to, melt blowing, spinbonding, film aperturing, and staple fiber carding. A continuous filament process may also be used, or a spunbonding process may be used. The spunbonding process is well known in the art. Generally it involves the extrusion of fibers through a spinneret. These fibers are then drawn using high velocity air and laid on an endless belt. A calender roll is generally then used to heat the web and bond the fibers to one another although other techniques may be used such as sonic bonding and adhesive bonding.

Embodiments

Accordingly, the instant disclosure relates to the following embodiments:

E1. A catalyst compound represented by the formula:

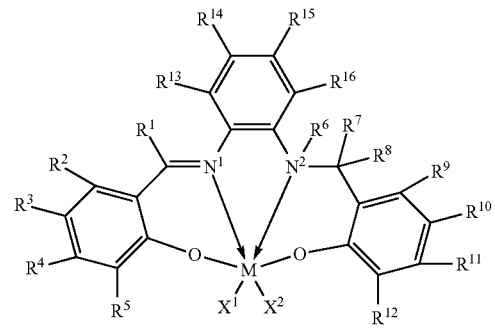

wherein each solid line represents a covalent bond and each arrow represents a bond having a varying degree of covalency and a varying degree of coordination;

wherein M is a Group 4 metal;

$N^1$ and $N^2$ are nitrogen;

O is oxygen;

each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

E2. The embodiment according to E1 wherein M is Hf.

E3. The embodiment according to E1 wherein M is Ti.

E4. The embodiment according to E1 wherein M is Zr.

E5. The embodiment according to any one of E1 through E4, wherein each of $X^1$ and $X^2$ is, independently, a halogen or a benzyl radical.

E6. The embodiment according to any one of E1 through E5, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a halogen, or a $C_1$ to $C_{30}$ hydrocarbyl radical, or a $C_1$ to $C_{20}$ hydrocarbyl radical, or a $C_1$ to $C_{10}$ hydrocarbyl radical.

E7. The embodiment according to any one of E1 through E6, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, or wherein at least one of $R^3$, $R^5$, $R^{10}$, and $R^{12}$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ hydrocarbyl radical or alkyl radical.

E8. The embodiment according to any one of E1 through E7, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, or wherein at least one of $R^3$, $R^5$, $R^{10}$, and $R^{12}$ is, independently, a $C_1$-$C_{10}$ aliphatic radical or a $C_1$-$C_{10}$ alicyclic radical.

E9. The embodiment according to any one of E1 through E8, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, or wherein at least one of $R^3$, $R^5$, $R^{10}$, and $R^{12}$ is, independently, a bulky functional group radical having a molecular size greater than or equal to a molecular size of an isopropyl functional group radical.

E10. The embodiment according to any one of E1 through E9, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, or wherein at least one of $R^3$, $R^5$, $R^{10}$, and $R^{12}$ is, independently, a substituted or unsubstituted aliphatic radical having four carbons or more, a substituted or unsubstituted alicyclic radical having six carbons or more, or a combination thereof.

E11. The embodiment according to any one of E1 through E10, wherein at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, or wherein at least one of $R^3$, $R^5$, $R^{10}$, and $R^{12}$ is, independently, a methyl radical, an adamantyl radical or a tert-butyl radical.

E12. The embodiment according to any one of E1 through E11, wherein at least one of $R^5$ and $R^{12}$ is, independently, a substituted or unsubstituted carbazolyl radical.

E13. The embodiment according to any one of E1 through E12, wherein each of $R^3$ and $R^5$ is, independently, an electron withdrawing functional group radical comprising —$NO_2$, —$CF_3$, —$CCl_3$, —$CBr_3$, —$C_{13}$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and wherein each of $R^{10}$ and $R^{12}$ is, independently, a $C_1$-$C_{10}$ aliphatic radical or a $C_1$-$C_{10}$ alicyclic radical.

E14. The embodiment according to any one of E1 through E12, wherein each of $R^3$ and $R^5$ is, independently, a $C_1$-$C_{10}$ aliphatic radical or a $C_1$-$C_{10}$ alicyclic radical, and wherein each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

E15. The embodiment according to any one of E1 through E12, wherein each of $R^3$ and $R^5$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and wherein each of $R^{10}$ and $R^{12}$ is, independently, a bulky functional group radical having a molecular size greater than or equal to a molecular size of an isopropyl functional group radical.

E16. The embodiment according to any one of E1 through E12, wherein each of $R^3$ and $R^5$ is, independently, a bulky functional group radical having a molecular size greater than or equal to a molecular size of an isopropyl functional group radical, and wherein each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

E17. The embodiment according to any one of E1 through E16, wherein $R^2$ is identical in composition to $R^9$, $R^3$ is identical in composition to $R^{10}$, $R^4$ is identical in composition to $R^{11}$, $R^5$ is identical in composition to $R^{12}$, or a combination thereof.

E18. The embodiment according to any one of E1 through E17, wherein $R^2$ is different in composition than $R^9$, $R^3$ is different in composition than $R^{10}$, $R^4$ is different in composition than $R^{11}$, $R^5$ is different in composition than $R^{12}$, or a combination thereof.

E19. The embodiment according to anyone of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^5$ is tert-butyl, $R^6$ is methyl, and each of $R^{10}$ and $R^{12}$ is independently F, Cl, Br, or I.

E20. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^6$ is methyl, $R^5$ is adamantyl, and each of $R^{10}$ and $R^{12}$ is independently F, Cl, Br, or I.

E21. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^6$, and $R^{10}$ is methyl, and each of $R^5$ and $R^{10}$ is adamantyl.

E22. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^5$, $R^{10}$ and $R^{12}$ is tert-butyl, and $R^6$ is methyl.

E23. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^5$ is independently F, Cl, Br, or I, each of $R^6$ and $R^{10}$ is methyl, and $R^{12}$ is adamantyl.

E24. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$, $R^5$, $R^{10}$, and $R^{12}$ is independently F, Cl, Br, or I, and $R^6$ is methyl.

E25. The embodiment according to any one of E1 through E18, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, each of $R^3$ and $R^6$ is methyl, $R^5$ is adamantyl, $R^{10}$ is tert-butyl, and $R^{12}$ is 4,4'-di-tert-butyl carbazolyl.

E26. The embodiment according to any one of E1 through E18, wherein the catalyst compound is represented by any one of the formulae i through xvii:

i
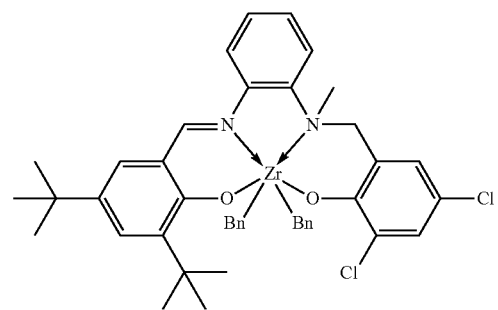
ii
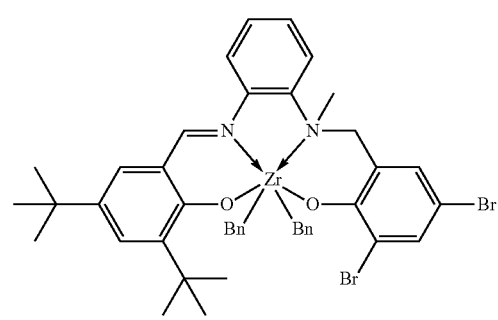
iii
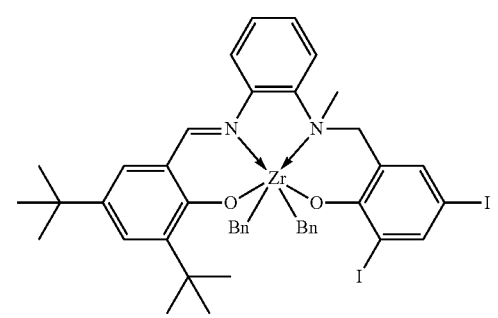
iv
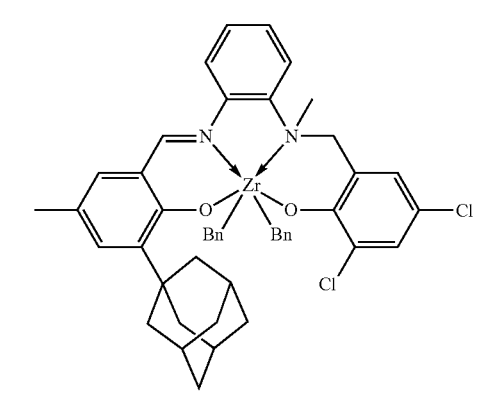
-continued
v
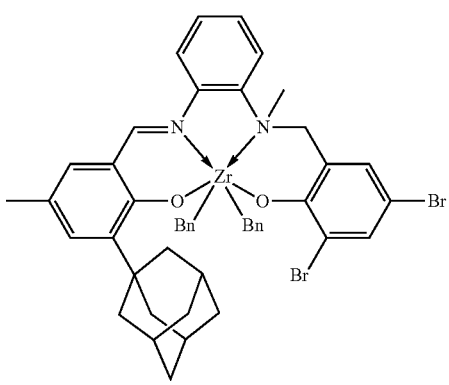
vi
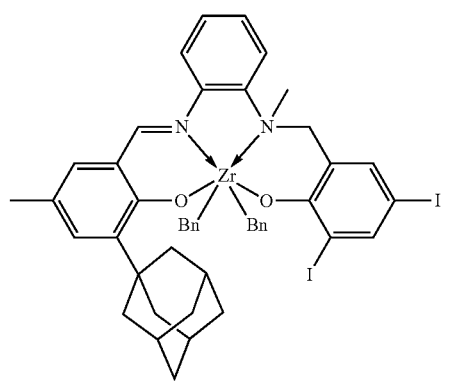
vii
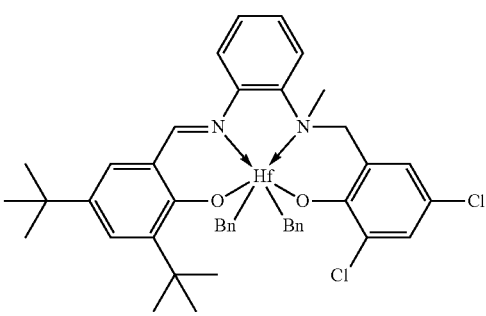
viii
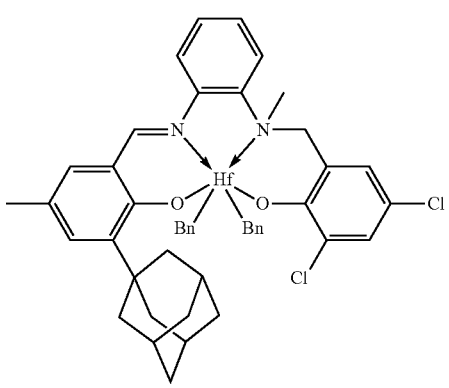

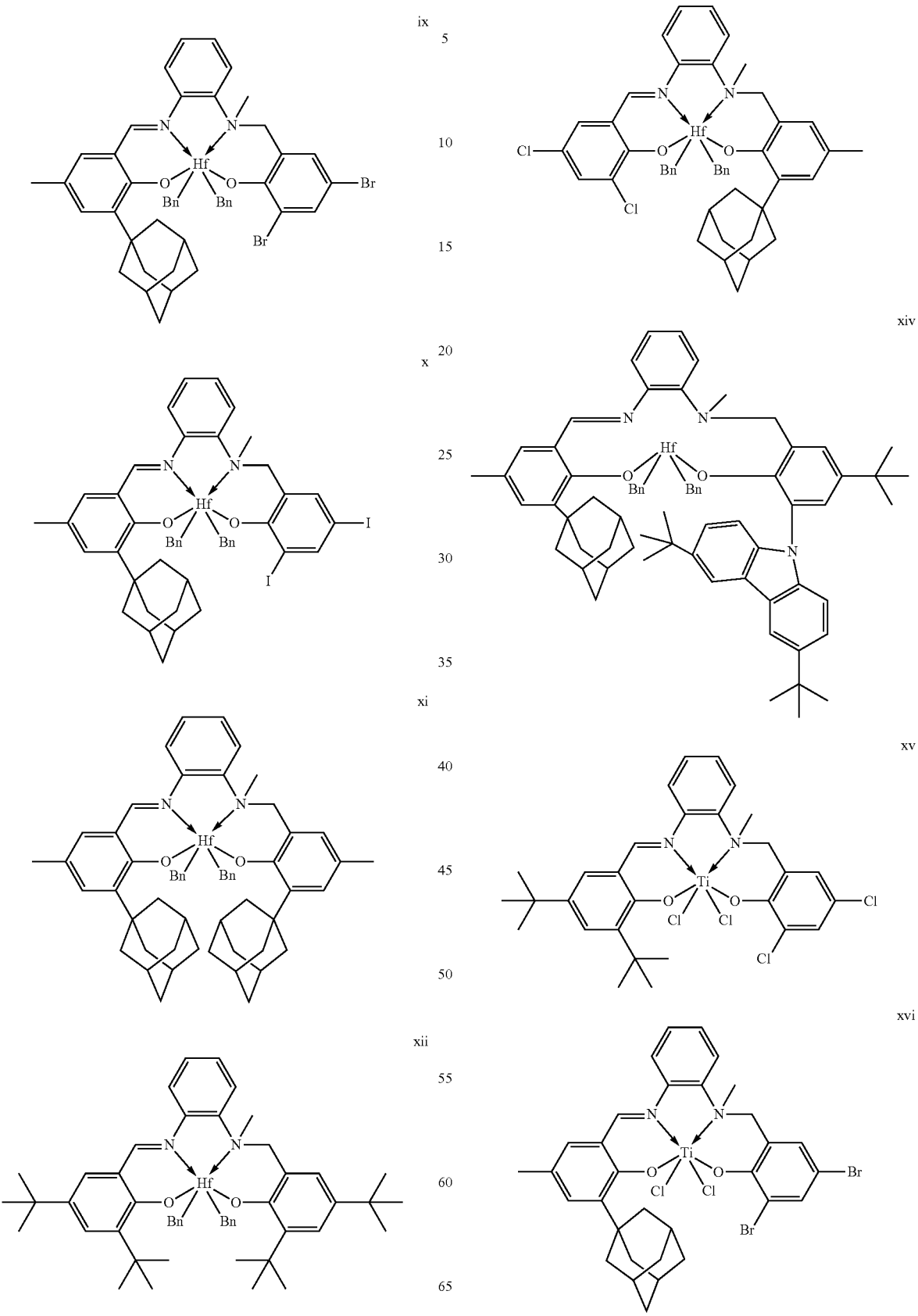

-continued

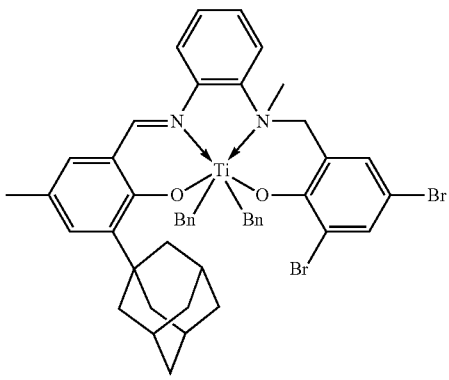

xvii wherein Bn is benzyl.

E27. A catalyst system comprising an activator and/or co-catalyst and a catalyst compound according to any one of embodiments E1-E26.

E28. A catalyst system comprising:
an activator and a catalyst compound represented by the formula:

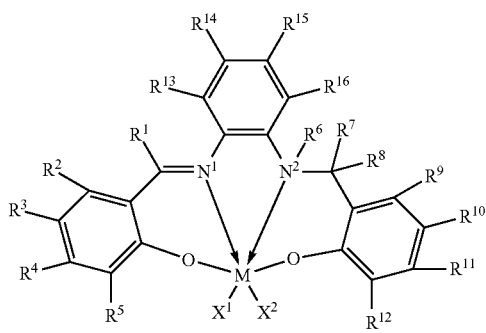

wherein each solid line represents a covalent bond and each arrow represents a bond having a varying degree of covalency and a varying degree of coordination;
wherein M is a Group 4 metal;
$N^1$ and $N^2$ are nitrogen and O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

E29. The catalyst system according to embodiments E27 or E28, wherein the activator comprises an alumoxane, a modified alumoxane, a noncoordinating or weakly coordinating anion, or a combination thereof.

E30. The catalyst system according to any one of embodiments E27 through E29, wherein the activator is a trimethylaluminum-depleted activator.

E31. The catalyst system according to any one of embodiments E27 through E30, wherein a minimum activator-to-catalyst-compound molar ratio is from about 1:1 to about 500:1.

E32. The catalyst system according to any one of embodiments E27 through E31, comprising less than 0.001 wt % alumoxane.

E33. A process comprising:
contacting one or more olefins with a catalyst system according to any one of embodiments E26 through E31 or E61 through E69, at a temperature, a pressure, and for a period of time sufficient to produce a polyolefin.

E34. A process comprising:
contacting one or more olefins with a catalyst system at a temperature, a pressure, and for a period of time sufficient to produce a polyolefin;
the catalyst system comprising an activator and a catalyst compound represented by the formula:

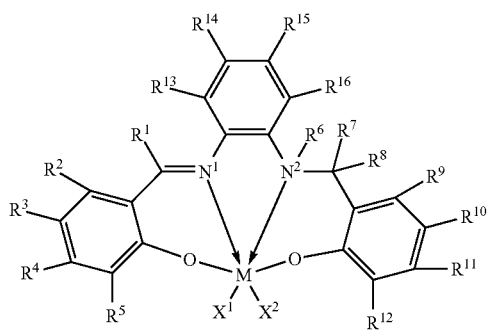

wherein each solid line represents a covalent bond and each arrow represents a bond having a varying degree of covalency and a varying degree of coordination;
wherein M is a Group 4 metal;
$N^1$ and $N^2$ are nitrogen and O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

E35. The process according to embodiments E33 or E34 wherein the catalyst compound is disposed on a support.

E36. The process according to any one of embodiments E33 through E35, wherein the one or more olefins includes propylene,
wherein the polyolefin is a propylene polymer having a melting point of greater than 145° C. determined by differential scanning calorimetry, and
wherein the polyolefin comprises a meso-pentad [mmmm] content of greater than or equal to about 89%, as determined by $^{13}$C NMR.

E37. The process according to any one of embodiments E33 through E36, wherein: M is Hf; $R^3$ is a methyl radical; $R^5$ is an adamantyl radical; and $R^{10}$ and $R^{12}$ are each independently a bromine radical or an iodine radical;

E38 The process according to any one of embodiments E33 through E35, wherein the one or more olefins includes propylene, wherein the polyolefin is a propylene polymer having a melting point of greater than 150° C. determined by differential scanning calorimetry, and wherein the polyolefin comprises a meso-pentad [mmmm] content of greater than or equal to about 95%, as determined by $^{13}$C NMR.

E39. The process according to any one of embodiments E33 through E35, wherein: M is Zr; $R^3$ is a methyl radical; $R^5$ is an adamantyl radical; and $R^{10}$ and $R^{12}$ are each independently a bromine radical.

E40. The process according to any one of embodiments E33 through E35, wherein the one or more olefins includes propylene; wherein the polyolefin is an atactic propylene polymer, and wherein the polyolefin comprises a weight average molecular weight (Mw) greater than 100,000 g/mol and a molecular weight distribution (Mw/Mn) of less than 5, wherein Mw and Mn are each determined by gel permeation chromatography.

E41. The process according to any one of embodiments E33 through E35, wherein: M is Ti; $R^3$ is a $C_1$-$C_{10}$ aliphatic radical; $R^5$ is an aliphatic or alicyclic bulky functional group radical having a molecular size greater than or equal to a molecular size of an isopropyl functional group radical; and $R^{10}$ and $R^{12}$ are each independently a halogen radical.

E42. The process according to any one of embodiments E33 through E41, wherein the activator comprises an alumoxane, a modified alumoxane, a noncoordinating or weakly coordinating anion, or a combination thereof.

E43. The process according to any one of embodiments E33 through E42, wherein the activator is a trimethylaluminum-depleted activator.

E44. The process according to any one of embodiments E33 through E43, wherein a minimum activator-to-catalyst-compound molar ratio is from about 1:1 to about 500:1.

E45. The process according to any one of embodiments E33 through E44 comprising less than 0.001 wt % alumoxane.

E46. The process according to any one of embodiments E33 through E45 wherein the polymer produced is an atactic polypropylene polymer, the process comprising contacting one or more olefins with a catalyst system according to any one of embodiments E26 through E31 wherein M is titanium (i.e., a titanium based phenylene bridged Salalen catalyst) according to any one of embodiments E3 through E25 at a temperature, a pressure, and for a period of time sufficient to produce the atactic polypropylene polymer, wherein the catalyst comprises a phenylene Salalen ligand system selected for being a phenylene bridged Salalen ligand system which is useful to produce (i.e., capable of producing) an isotactic polypropylene polymer having a meso-pentad [mmmm] content of greater than or equal to about 60%, or about 80%, or about 90%, when the phenylene Salalen ligand system is coordinated with hafnium or zirconium.

E47. The polyolefin obtained by the process according to any one of embodiments E33 through E46.

E48. The polyolefin according to embodiment E47 comprising a propylene polymer having an isotacticity of at least 80%, determined by $^{13}$C NMR.

E49. The polyolefin according to embodiments E47 or E48, comprising a propylene polymer having an isotacticity of at least 95% determined by $^{13}$C NMR.

E50. The polyolefin according to any one of embodiments E47 through E49 comprising at least 1 ppm Ti.

E51. The polyolefin according to any one of embodiments E47 through E50 comprising an atactic propylene polymer having a weight average molecular weight of greater than or equal to about 100,000 g/mol, determined using gel permeation chromatography.

E52. The polyolefin according to any one of embodiments E47 through E50 comprising an isotactic propylene polymer having a weight average molecular weight of greater than or equal to about 20,000 g/mol and less than or equal to about 100,000 g/mol, determined using gel permeation chromatography.

E53. The polyolefin according to any one of embodiments E47 through E52 having an Mw/Mn of greater than or equal to about 1 to about 40, or from about 1.9 to about 20, or from about 2.9 to about 10, or from about 3 to about 8, or from about 3 to about 4.

E54. The polyolefin according to any one of embodiments E47 through E53, including monomers comprising substituted or unsubstituted $C_2$ to $C_{40}$ alpha olefins, or $C_2$ to $C_{20}$ alpha olefins, or $C_2$ to $C_{12}$ alpha olefins, or ethylene, or propylene, or butene, or pentene, or hexene, or heptene, or octene, or nonene, or decene, or undecene, or dodecane, or a combination thereof.

E55. The polyolefin according to any one of embodiments E47 through E54, wherein the monomer olefins are strained or unstrained; wherein the monomer olefins are monocyclic or polycyclic, wherein the monomer olefins include heteroatoms, wherein the monomer olefins comprise one or more functional groups, or a combination thereof.

E56. The polyolefin according to any one of embodiments E47 through E55, comprising at least about 0.01 ppm by weight of a catalyst compound or a decomposition residue of a catalyst compound represented by the formula:

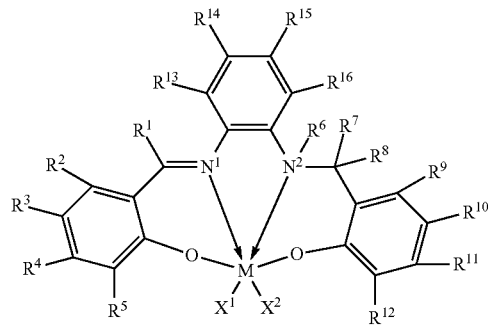

wherein each solid line represents a covalent bond and each arrow represents a bond having a varying degree of covalency and a varying degree of coordination;

wherein M is a Group 4 metal;

$N^1$ and $N^2$ are nitrogen and O is oxygen;

each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;

wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

E57. The polyolefin according to any one of embodiments E47 through E56, comprising less than or equal to about 0.1 ppm by weight of aluminum.

E58. A molded article comprising the polyolefin according to any one of embodiments E47 through E57.

E59. A film comprising the polyolefin according to any one of embodiments E47 through E57.

E60. A nonwoven fabric and/or fiber comprising the polyolefin according to any one of embodiments E47 through E57.

E61. The catalyst system according to any one of embodiments E28 through E32, wherein at least one of $R^3$, $R^5$, $R^{10}$, and $R^{12}$ is, independently, an electron withdrawing functional group radical comprising —$NO_2$, —$CF_3$, —$CCl_3$, —$CBr_3$, —$C_{13}$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

E62. The catalyst system according to any one of embodiments E28 through E32, wherein at least one of $R^3$, $R^5$, $R^{10}$, and $R^{12}$ is, independently, a $C_1$-$C_{10}$ aliphatic radical or a $C_1$-$C_{10}$ alicyclic radical.

E63. The catalyst system according to any one of embodiments E28 through E32, wherein at least one of $R^3$, $R^5$, $R^{10}$, and $R^{12}$ is, independently, a methyl radical, an adamantyl radical or a tert-butyl radical.

E64. The catalyst system according to any one of embodiments E28 through E32, wherein at least one of $R^5$ and $R^{12}$ is, independently, a substituted or unsubstituted carbazolyl radical.

E65. The catalyst system according to any one of embodiments E28 through E32, wherein M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, and wherein: i) each of $R^3$ and $R^5$ is tert-butyl, $R^6$ is methyl, and each of $R^{10}$ and $R^{12}$ is independently F, Cl, Br, or I; or ii) each of $R^3$ and $R^6$ is methyl, $R^5$ is adamantyl, and each of $R^{10}$ and $R^{12}$ is independently F, Cl, Br, or I; or iii) each of $R^3$, $R^6$, and $R^{10}$ is methyl, and each of $R^5$ and $R^{10}$ is adamantyl; or iv) each of $R^3$, $R^5$, $R^{10}$ and $R^{12}$ is tert-butyl, and $R^6$ is methyl; or v) each of $R^3$ and $R^5$ is independently F, Cl, Br, or I, each of $R^6$ and $R^{10}$ is methyl, and $R^{12}$ is adamantyl; or vi) each of $R^3$, $R^5$, $R^{10}$, and $R^{12}$ is independently F, Cl, Br, or I, and $R^6$ is methyl; or vii) each of $R^3$ and $R^6$ is methyl, $R^5$ is adamantyl, $R^{10}$ is tert-butyl, and $R^{12}$ is 4,4'-di-tert-butyl carbazolyl.

E66. The catalyst system according to any one of embodiments E28 through E32, or E61 through E65, wherein the activator is an alumoxane.

E67. The catalyst system according to any one of embodiments E28 through E32, or E61 through E65, wherein the activator is a non-coordinating anion activator.

E68. The catalyst system according to any one of embodiments E28 through E32, or E61 through E65, wherein the activator is a non-coordinating anion activator selected from the group consisting of:
N,N-dimethylanilinium tetrakis(perfluorophenyl)borate,
methyldioctadecylammonium tetrakis(perfluorophenyl)borate,
methyldi($C_{14-20}$ alkyl)ammonium tetrakis(perfluorophenyl)borate,
trimethylammonium tetrakis(perfluoronaphthyl)borate,
triethylammonium tetrakis(perfluoronaphthyl)borate,
tripropylammonium tetrakis(perfluoronaphthyl)borate,
tri(n-butyl)ammonium tetrakis(perfluoronaphthyl)borate,
tri(t-butyl)ammonium tetrakis(perfluoronaphthyl)borate,
N,N-dimethylanilinium tetrakis(perfluoronaphthyl)borate,
N,N-diethylanilinium tetrakis(perfluoronaphthyl)borate,
N,N-dimethyl-(2,4,6-trimethylanilinium) tetrakis(perfluoronaphthyl)borate,
tropillium tetrakis(perfluoronaphthyl)borate,
triphenylcarbenium tetrakis(perfluoronaphthyl)borate,
triphenylphosphonium tetrakis(perfluoronaphthyl)borate,
triethylsilylium tetrakis(perfluoronaphthyl)borate,
benzene(diazonium) tetrakis(perfluoronaphthyl)borate,
trimethylammonium tetrakis(perfluorobiphenyl)borate,
triethylammonium tetrakis(perfluorobiphenyl)borate,
tripropylammonium tetrakis(perfluorobiphenyl)borate,
tri(n-butyl)ammonium tetrakis(perfluorobiphenyl)borate,
tri(t-butyl)ammonium tetrakis(perfluorobiphenyl)borate,
N,N-dimethylanilinium tetrakis(perfluorobiphenyl)borate,
N,N-diethylanilinium tetrakis(perfluorobiphenyl)borate,
N,N-dimethyl-(2,4,6-trimethylanilinium) tetrakis(perfluorobiphenyl)borate,
tropillium tetrakis(perfluorobiphenyl)borate,
triphenylcarbenium tetrakis(perfluorobiphenyl)borate,
triphenylphosphonium tetrakis(perfluorobiphenyl)borate,
triethylsilylium tetrakis(perfluorobiphenyl)borate,
benzene(diazonium) tetrakis(perfluorobiphenyl)borate, and
[4-t-butyl-PhNMe$_2$H][($C_6F_3(C_6F_5)_2)_4$B], where Ph is phenyl, and Me is methyl.

E69. The catalyst system according to any one of embodiments E28 through E32, or E61 through E65, wherein the activator is a non-coordinating anion activator selected from the group consisting of: N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B($C_6F_5)_4{}^-$], where Ph is phenyl, and Me is methyl, [Me$_3$NH$^+$][B($C_6F_5)_4{}^-$], where Ph is phenyl, and Me is methyl, 1-(4-(tris(pentafluorophenyl)borate)-2,3,5,6-tetrafluorophenyl)pyrrolidinium, tetrakis(pentafluorophenyl)borate, and 4-(tris(pentafluorophenyl)borate)-2,3,5,6-tetrafluoropyridine.

E70. The process according to any one of embodiments E33 through E46, wherein the activator is an alumoxane.

E71. The process according to any one of embodiments E33 through E46, wherein the activator is a non-coordinating anion activator.

E72. The process according to any one of embodiments E33 through E46, wherein the activator is a non-coordinating anion activator selected from the group consisting of: N,N-dimethylanilinium tetrakis(perfluorophenyl)borate, methyldioctadecylammonium tetrakis(perfluorophenyl)borate, methyldi($C_{14-20}$ alkyl)ammonium tetrakis(perfluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene (diazonium) tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis(perfluorobiphenyl)borate, and [4-t-butyl-PhNMe$_2$H] [($C_6F_3(C_6F_5)_2)_4$B], where Ph is phenyl, and Me is methyl.

E73. The process according to any one of embodiments E33 through E46, wherein the activator is a non-coordinating anion activator selected from the group consisting of: N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B($C_6F_5)_4^-$], where Ph is phenyl, and Me is methyl, [Me$_3$NH$^+$][B($C_6F_5)_4^-$], where Ph is phenyl, and Me is methyl, 1-(4-(tris(pentafluorophenyl)borate)-2,3,5,6-tetrafluorophenyl)pyrrolidinium, tetrakis(pentafluorophenyl)borate, and 4-(tris(pentafluorophenyl)borate)-2,3,5,6-tetrafluoropyridine.

EXAMPLES

The foregoing discussion can be further described with reference to the following non-limiting examples. Illustrative catalyst compounds according to embodiments described herein, were synthesized and used to polymerize olefins. All reactions were carried out under a purified nitrogen atmosphere using standard glovebox, high vacuum or Schlenk techniques, unless otherwise noted. All solvents used were anhydrous, de-oxygenated and purified according to known procedures. All starting materials were either purchased and purified prior to use or prepared according to procedures known to those skilled in the art. MAO refers to methylaluminoxane. MAO was obtained from Sigma-Aldrich Chemical Co. (St. Louis, Mo.). Deuterated solvents were obtained from Cambridge Isotope Laboratories (Andover, Mass.) and dried over 3 Å molecular sieves.

As used herein, Mn refers to the number average molecular weight as determined by gel permeation chromatography (GPC). Mw refers to the weight average molecular weight determined by GPC, and Mz refers to the z average molecular weight determined by GPC, wt % is weight percent, and mol % is mole percent. Unless otherwise noted, all molecular weight units, e.g., Mw, Mn, Mz, are g/mol. The Mn, Mw, Mz, number of carbon atoms, g value and g'$_{vis}$ were determined via GPC using a commercially available High Temperature Size Exclusion Chromatograph (Waters Corporation) equipped with a differential refractive index detector (DRI), a light scattering (LS) detector, and a viscometer according to the procedures described herein.

Melting temperature (melting point, T$_m$) and heat of fusion (AH or Hf) were measured using Differential Scanning calorimetry (DSC) on a commercially available instrument (TA Instruments 2920 DSC). Typically, 6 to 10 mg of molded polymer or plasticized polymer were sealed in an aluminum pan and loaded into the instrument at room temperature. Data were acquired by heating the sample to at least 30° C. above its melting temperature, typically 220° C. for polypropylene, at a heating rate of 10° C./min. The sample was held for at least 5 minutes at this temperature to destroy its thermal history. Then the sample was cooled from the melt to at least 50° C. below the crystallization temperature, typically –100° C. for polypropylene, at a cooling rate of 20° C./min. The sample was held at this temperature for at least 5 minutes and finally heated at 10° C./min to acquire additional melting data (second heat). The endothermic melting transition (first and second heat) and exothermic crystallization transition were analyzed according to standard procedures. The melting temperatures (Tm) reported are the peak melting temperatures from the second heat unless otherwise specified. For polymers displaying multiple peaks, the melting temperature was defined to be the peak melting temperature from the melting trace associated with the largest endothermic calorimetric response (as opposed to the peak occurring at the highest temperature). Likewise, the crystallization temperature was defined to be the peak crystallization temperature from the crystallization trace associated with the largest exothermic calorimetric response (as opposed to the peak occurring at the highest temperature). Areas under the DSC curve were used to determine the heat of transition (heat of fusion, Hf, upon melting or heat of crystallization, H$_c$, upon crystallization).

The polypropylene microstructure was determined by $^{13}$C-NMR spectroscopy, including the concentration of isotactic and syndiotactic diads ([m] and [r]), triads ([mm] and [rr]), and pentads ([mmmm] and [rrrr]) as described herein. Samples were dissolved in d$_2$-1,1,2,2-tetrachloroethane, and spectra recorded at a temperature between 100° C. and 150° C., typically 120° C.-125° C. using a commercially available 100 MHz (or higher) NMR spectrometer. Polymer resonance peaks are referenced to mmmm=21.8 ppm. Calculations involved in the characterization of polymers by NMR are consistent with those described by F. A. Bovey in Polymer Conformation and Configuration (Academic Press, New York 1969) and J. Randall in Polymer Sequence Determination, $^{13}$C-NMR Method (Academic Press, New York, 1977).

$^{13}$C NMR data were collected at between 100° C. and 150° C. in a 5 mm dual $^{13}$C/$^1$H probe or 10 mm probe using a commercially available NMR (Varian NMR spectrometer) with a $^1$Hydrogen frequency of at least 100 MHz. A pulse angle between 20° and 90° was used with an acquisition time adjusted to give a digital resolution between 0.1 and 0.12 Hz, at least a 1 second pulse acquisition delay time with continuous broadband proton decoupling using swept square wave modulation without gating is employed during the entire acquisition period. The spectra are acquired using time averaging to provide a signal to noise level adequate to measure the signals of interest. Prior to data analysis, spectra were referenced by setting the chemical shift of the (—CH$_2$—)$_n$ signal where n>6 to 29.9 ppm.

The exemplary Salalen precursor compounds were prepared via reaction of a 4,6 substituted 2-halomethyl phenol with a 2,4 substituted 2-(((methylamino)phenyl)imino)methyl) phenol in the presence of triethyl amine. The exemplary Salalen precursor compounds, also referred to as phenylene-bridged Salalen ligand systems and/or as Salalen ligand systems Lig$^1$H$_2$ through Lig$^{13}$H$_2$ are shown in Table 1. The exemplary Salalen catalysts were then prepared via reaction of the Salalen precursor ligands Lig$^1$H$_2$ through Lig$^{13}$H$_2$ with a tetrasubstituted Group 4 metal compound. The exemplary Salalen catalysts are shown in Table 2.

Synthesis of 2,4-di-tert-butyl-6-((2-(methylamino)phenyl)imino)methyl)phenol

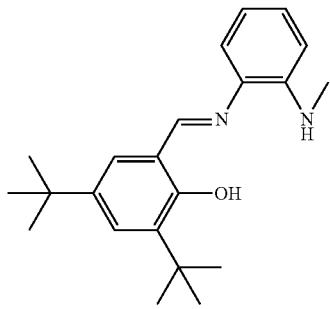 [SMILES: CNc1ccccc1/N=C/c1cc(C(C)(C)C)cc(C(C)(C)C)c1O]

N-Methyl-1,2-phenylenediamine (0.58 g, 4.8 mmol) was added to a solution of 3,5-di-tert-butyl-2-hydroxy-benzaldehyde (1.11 g, 4.8 mmol) in benzene and refluxed for 2 h. The solvent was removed under vacuum yielding an orange solid quantitatively.

$^1$H NMR (CDCl$_3$, 500 MHz): δ=8.61 (s, 1H, NCH), 7.44-7.17 (m, 4H, ArH), 7.00 (d, 1H, J=4.5 Hz, ArH), 6.73 (d, 1H, J=4.5 Hz, ArH), 4.40 (s, 1H, NH), 2.92 (s, 3H, NCH$_3$), 1.47 (s, 9H, (CH$_3$)$_3$), 1.33 (s, 9H, (CH$_3$)$_3$).

Synthesis of Lig$^1$H$_2$

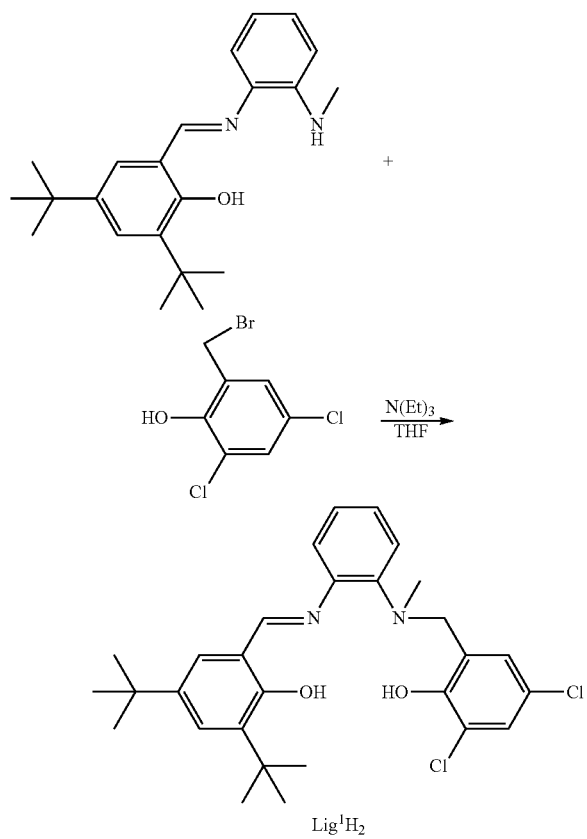

A solution of 2-(bromomethyl)-4,6-dichlorophenol (0.72 g, 2.8 mmol) in THF (20 mL) was added dropwise to a solution of 2,4-di-tert-butyl-6-(((2-(methylamino)phenyl)imino)methyl)phenol (0.73 g, 1.9 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor Lig$^1$H$_2$ as a yellow solid quantitatively.

$^1$H NMR (CDCl$_3$, 500 MHz): δ=8.59 (s, 1H, NCH), 7.47 (d, 1H, J=2.4 Hz, ArH), 7.28-7.21 (m, 4H, ArH), 7.11 (d, 1H, J=1.1 Hz, ArH), 7.09 (d, 1H, J=1.1 Hz, ArH), 6.95 (d, 1H, J=2.4 Hz, ArH), 4.28 (s, 2H, CH$_2$), 2.73 (s, 3H, NCH$_3$), 1.46 (s, 9H, (CH$_3$)$_3$), 1.33 (s, 9H, (CH$_3$)$_3$).

$^{13}$C NMR (CDCl$_3$, 100.67 MHz): δ=165.5 (CN), 158.2 (CO), 152.3 (CO), 145.1 (C), 144.0 (C), 140.6 (C), 137.3 (CH), 128.7 (CH), 128.6 (CH), 127.3 (CH), 127.2 (C), 126.9 (CH), 126.3 (C), 123.7 (C), 121.1 (C), 120.6 (C), 59.2 (CH$_2$), 42.5 (NCH$_3$), 35.1 (C), 34.2 (C), 31.5 (CH$_3$), 29.4 (CH$_3$).

Synthesis of Lig$^2$H$_2$

Lig$^2$H$_2$ was produced according to the same procedure as Lig$^1$H$_2$ utilizing 2-(bromomethyl)-4,6-dibromophenol.

Synthesis of Lig$^3$H$_2$

Lig$^3$H$_2$ was produced according to the same procedure as Lig$^1$H$_2$ utilizing 2-(bromomethyl)-4,6-diiodophenol.

Synthesis of Lig$^4$H$_2$

A solution of 2-(bromomethyl)-4,6-dichlorophenol (0.50 g, 1.9 mmol) in THF (20 mL) was added dropwise to a solution of 2-((adamantan-1-yl)-4-methyl-6-(((2-(methylamino)phenyl)imino)methyl)phenol (0.73 g, 1.9 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether: dichloromethane in increasing polarity as eluent yielding the ligand precursor Lig$^4$H$_2$ as a yellow solid quantitatively.

$^1$H NMR (CDCl$_3$, 500 MHz): δ=8.53 (s, 1H, NCH), 7.27 (d, 1H, J=1.6 Hz, ArH), 7.23-7.21 (m, 3H, ArH), 7.15 (d, 1H, J=2.1 Hz, ArH), 7.08 (m, 1H, ArH), 7.04 (d, 1H, J=1.6 Hz, ArH), 6.96 (d, 1H, J=2.1 Hz, ArH), 4.31 (s, 2H, CH$_2$), 2.31 (s, 3H, NCH$_3$), 2.17 (m, 6H, adamantyl), 2.16 (s, 3H, CH$_3$), 2.07 (m, 3H, adamantyl), 1.81-1.75 (m, 4H, adamantyl).

$^{13}$C NMR (CDCl$_3$, 100.67 MHz): δ=165.2 (CN), 158.5 (CO), 152.3 (CO), 145.0 (C), 144.1 (C), 137.9 (C), 132.1 (CH), 130.6 (CH), 128.6 (CH), 127.3 (CH), 126.7 (C), 126.2 (CH), 123.5 (C), 123.4 (C), 120.9 (C), 120.5 (C), 59.4 (CH$_2$), 59.4 (CH$_2$), 42.1 (NCH$_3$), 37.1 (CH$_2$), 37.0 (C), 29.5 (CH$_2$), 29.1 (ArCH$_3$), 20.7 (CH$_2$).

Synthesis of Lig$^5$H$_2$

A solution of 2-(bromomethyl)-4,6-dibromophenol (0.83 g, 2.4 mmol) in THF (20 mL) was added dropwise to a solution of 2-((adamantan-1-yl)-4-methyl-6-(((2-(methylamino)phenyl)imino)methyl)phenol (0.90 g, 1.9 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor Lig$^5$H$_2$ as a yellow solid quantitatively.

$^1$H NMR (CDCl$_3$, 400 MHz): δ=8.52 (s, 1H, NCH), 7.52 (d, 1H, J=2.2 Hz, ArH), 7.23-7.21 (m, 2H, ArH), 7.15 (d, 1H, J=2.0 Hz, ArH), 7.13 (d, 1H, J=2.2 Hz, ArH), 7.07-7.04 (m, 3H, ArH), 4.30 (s, 2H, CH$_2$), 2.71 (s, 3H, NCH$_3$), 2.30 (s, 3H, CH$_3$), 2.18 (m, 6H, adamantyl), 2.07 (m, 3H, adamantyl), 1.79 (m, 4H, adamantyl).

$^{13}$C NMR (CDCl$_3$, 100.67 MHz): δ=165.4 (CN), 158.5 (CO), 154.0 (CO), 138.6 (C), 138.3 (C), 135.3 (C), 134.2 (CH), 132.2 (CH), 130.6 (CH), 130.3 (CH), 127.2 (C), 126.3 (CH), 124.1 (C), 123.1 (C), 121.4 (CH), 121.0 (CH), 119.1 (C), 118.8 (C), 59.4 (CH$_2$), 42.1 (NCH$_3$), 37.2 (CH$_2$), 37.1 (C), 29.1 (ArCH$_3$), 20.6 (CH$_2$).

Synthesis of Lig$^6$H$_2$

A solution of 2-(bromomethyl)-4,6-diiodophenol (0.51 g, 1.2 mmol) in THF (20 mL) was added dropwise to a solution of 2-((adamantan-1-yl)-4-methyl-6-(((2-(methylamino)phenyl)imino)methyl)phenol (0.41 g, 1.2 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether: dichloromethane in increasing polarity as eluent yielding the ligand precursor Lig$^6$H$_2$ as a yellow solid quantitatively.

$^1$H NMR (CDCl$_3$, 400 MHz): δ=8.51 (s, 1H, NCH), 7.90 (d, 1H, J=1.9 Hz, ArH), 7.30-7.28 (m, 2H, ArH), 7.27 (d, 1H, J=2.0 Hz, ArH), 7.24 (m, 1H, ArH), 7.16 (d, 1H, J=2.0 Hz, ArH), 7.06-7.04 (m, 3H, ArH), 4.25 (s, 2H, CH$_2$), 2.69 (s, 3H, NCH$_3$), 2.31 (s, 3H, CH$_3$), 2.19 (m, 6H, adamantyl), 2.08 (m, 3H, adamantyl), 1.78 (m, 4H, adamantyl).

$^{13}$C NMR (CDCl$_3$, 100.67 MHz): δ=166.3 (CN), 159.2 (CO), 157.7 (CO), 146.1 (C), 146.0 (C), 144.6 (C), 138.6 (C), 137.8 (CH), 132.9 (CH), 131.4 (CH), 128.0 (CH), 127.9 (C), 127.1 (CH), 124.3 (C), 121.8 (C), 121.5 (CH), 119.5 (CH), 87.6 (C), 81.9 (C), 59.7 (CH$_2$), 43.0 (NCH$_3$), 41.0 (CH$_2$), 37.9 (CH$_2$), 37.8 (C), 29.8 (ArCH$_3$), 21.4 (CH$_2$).

Synthesis of Lig$^7$H$_2$

A solution of 2-(bromomethyl)-4-adamantyl-6-methylphenol (0.49 g, 1.4 mmol) in THF (20 mL) was added dropwise to a solution of 2-adamantyl-4-methyl-6-(((2-(methylamino)phenyl)imino)methyl)phenol (0.45 g, 1.4 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether: dichloromethane in increasing polarity as eluent yielding the ligand precursor Lig$^7$H$_2$ as a yellow solid quantitatively.

$^1$H NMR (CDCl$_3$, 500 MHz): δ=13.06 (s, 1H, OH), 9.91 (s, 1H, OH), 8.45 (s, 1H, NCH), 7.24-7.11 (m, 4H, ArH), 7.02 (s, 1H, ArH), 6.96 (m, 1H, ArH), 6.87 (s, 1H, ArH), 6.72 (m, 1H, ArH), 4.23 (s, 2H, CH$_2$), 2.76 (s, 3H, NCH$_3$), 2.29 (s, 3H, CH$_3$), 2.22 (s, 3H, CH$_3$), 2.19 (m, 6H, adamantyl), 2.07 (m, 3H, adamantyl), 1.98 (m, 6H, adamantyl), 1.91 (m, 3H, adamantyl), 1.77 (m, 6H, adamantyl), 1.64 (m, 6H, adamantyl).

Synthesis of Lig$^8$H$_2$

Lig$^8$H$_2$ was prepared according to the same procedure as used above wherein about 1.5 mmol of 2-(bromomethyl)-4,6-di-tert-butylphenol was added dropwise to a solution containing about 1.5 mmol of 2,4-di-tert-butyl-6-(((2-(methylamino)phenyl)imino)methyl)phenol and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether: dichloromethane in increasing polarity as eluent yielding the ligand precursor Lig$^8$H$_2$ as a yellow solid quantitatively.

$^1$H NMR (CDCl$_3$, 500 MHz): δ=8.60 (s, 1H, NCH), 7.46 (d, 1H, J=2.3 Hz, ArH), 7.29-7.19 (m, 5H, ArH), 7.08 (m, 1H, ArH), 6.94 (d, 1H, J=2.3 Hz, ArH), 4.29 (s, 2H, CH$_2$), 2.68 (s, 3H, NCH$_3$), 1.46 (s, 9H, (CH$_3$)$_3$), 1.36 (s, 9H, (CH$_3$)$_3$), 1.33 (s, 9H, (CH$_3$)$_3$), 1.29 (s, 9H, (CH$_3$)$_3$).

$^{13}$C NMR (CDCl$_3$, 100.67 MHz): δ=165.2 (CN), 158.2 (CO), 154.1 (CO), 145.3 (C), 145.0 (C), 140.5 (C), 140.4 (C), 137.1 (CH), 135.8 (CH), 128.3 (CH), 127.0 (CH), 125.4 (C), 123.1 (CH), 120.9 (C), 120.7 (C), 120.3 (CH), 118.4 (CH), 59.8 (CH$_2$), 42.8 (NCH$_3$), 35.1 (C), 34.8 (C), 34.2 (C), 34.1 (C), 31.7 (CH$_3$), 31.4 (CH$_3$), 29.7 (CH$_3$), 29.5 (CH$_3$).

Synthesis of Lig$^9$H$_2$

A solution of 2-(bromomethyl)-4-adamantyl-6-methylphenol (1.65 g, 4.9 mmol) in THF (20 mL) was added dropwise to a solution of 2,4-dichloro-6-(((2-(methylamino)phenyl)imino)methyl)phenol (1.32 g, 1.5 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor Lig$^9$H$_2$ as a yellow solid quantitatively.

$^1$H NMR (CDCl$_3$, 400 MHz): δ=8.44 (s, 1H, NCH), 7.44 (s, 1H, ArH), 7.29 (m, 3H, ArH), 7.18 (m, 1H, ArH), 7.03 (m, 1H, ArH), 6.89 (s, 1H, ArH), 6.70 (s, 1H, ArH), 4.18 (s, 2H, CH$_2$), 2.69 (s, 3H, NCH$_3$), 2.21 (s, 3H, CH$_3$), 2.01-1.90 (m, 9H, adamantyl), 1.69-1-63 (m, 6H, adamantyl).

$^{13}$C NMR (CDCl$_3$, 100.67 MHz): δ=162.9 (CN), 156.1 (CO), 154.6 (CO), 145.0 (C), 144.7 (C), 137.1 (C), 133.2 (CH), 128.3 (CH), 130.2 (CH), 128.6 (CH), 127.8 (CH), 127.1 (CH), 126.4 (CH), 121.9 (C), 120.2 (C), 59.6 (CH$_2$), 43.3 (NCH$_3$), 40.5 (CH$_2$), 37.4 (CH$_2$), 36.9 (C), 29.4 (ArCH$_3$), 21.1 (CH$_2$).

Synthesis of Lig$^{10}$H$_2$

A solution of 2-(bromomethyl)-4-adamantyl-6-methylphenol (0.52 g, 1.5 mmol) in THF (20 mL) was added dropwise to a solution of 2,4-dibromo-6-(((2-(methylamino)phenyl)imino)methyl)phenol (0.59 g, 1.5 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether: dichloromethane in increasing polarity as eluent yielding the ligand precursor Lig$^{10}$H$_2$ as a yellow solid quantitatively.

$^1$H NMR (CDCl$_3$, 400 MHz): δ=8.42 (s, 1H, NCH), 7.75 (s, 1H, ArH), 7.48 (s, 1H, ArH), 7.31-7.30 (m, 2H, ArH), 7.21-7.20 (m, 1H, ArH), 7.03-7.01 (m, 1H, ArH), 6.89 (s, 1H, ArH), 6.71 (s, 1H, ArH), 4.19 (s, 2H, CH$_2$), 2.71 (s, 3H, NCH$_3$), 2.22 (s, 3H, CH$_3$), 2.00 (m, 9H, adamantyl), 1.70-1-61 (m, 6H, adamantyl).

$^{13}$C NMR (CDCl$_3$, 100.67 MHz): δ=162.6 (CN), 157.1 (CO), 154.3 (CO), 144.7 (C), 144.5 (C), 138.4 (C), 136.9 (C), 133.6 (CH), 128.3 (CH), 127.3 (CH), 126.8 (CH), 126.1 (C), 121.6 (CH), 119.9 (C), 110.3 (C), 59.2 (CH$_2$), 43.1 (NCH$_3$), 40.3 (CH$_2$), 37.1 (CH$_2$), 36.7 (C), 29.1 (ArCH$_3$), 20.8 (CH$_2$).

Synthesis of Lig$^{11}$H$_2$

A solution of 2-(bromomethyl)-4-adamantyl-6-methylphenol (0.32 g, 1.0 mmol) in THF (20 mL) was added dropwise to a solution of 2,4-diiodo-6-(((2-(methylamino) phenyl)imino)methyl) phenol (0.42 g, 1.0 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor Lig$^{11}$H$_2$ as a yellow solid quantitatively.

$^1$H NMR (CDCl$_3$, 400 MHz): δ=8.34 (s, 1H, NCH), 8.11 (d, 1H, J=2.0 Hz, ArH), 7.67 (d, 1H, J=2.0 Hz, ArH), 7.31-7.30 (m, 2H, ArH), 7.21-7.18 (m, 1H, ArH), 7.01-6.99 (m, 1H, ArH), 6.90 (d, 1H, J=1.5 Hz, ArH), 6.71 (d, 1H, J=1.5 Hz, ArH), 4.19 (s, 2H, CH$_2$), 2.72 (s, 3H, NCH$_3$), 2.22 (s, 3H, CH$_3$), 1.99 (m, 9H, adamantyl), 1.70-1-60 (m, 6H, adamantyl).
$^{13}$C NMR (CDCl$_3$, 100.67 MHz): δ=162.4 (CN), 154.3 (CO), 153.0 (CO), 149.4 (C), 144.6 (C), 140.7 (C), 136.8 (C), 128.2 (CH), 127.3 (CH), 126.8 (CH), 126.0 (CH), 121.5 (C), 120.0 (CH), 87.1 (C), 80.0 (C), 59.3 (CH$_2$), 43.1 (NCH$_3$), 40.2 (CH$_2$), 37.1 (CH$_2$), 36.6 (C), 29.7 (ArCH$_3$), 20.8 (CH$_2$).

Synthesis of Lig$^{12}$H$_2$

A solution of 2-(bromomethyl)-4,6-dichlorophenol (0.42 g, 1.6 mmol) in THF (20 mL) was added dropwise to a solution of 2,4-dichloro-6-(((2-(methylamino)phenyl)imino) methyl)phenol (0.40 g, 1.6 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor Lig$^{12}$H$_2$ as a yellow solid quantitatively.

$^1$H NMR (CDCl$_3$, 400 MHz): δ=8.50 (s, 1H, NCH), 7.48 (d, 1H, J=2.0 Hz, ArH), 7.32 (d, 1H, J=2.0 Hz, ArH), 7.28-7.22 (m, 3H, ArH), 7.22 (d, 1H, J=2.0 Hz, ArH), 7.11 (m, 1H, ArH), 6.97 (d, 1H, J=2.0 Hz, ArH), 4.22 (s, 2H, CH$_2$), 2.79 (s, 3H, NCH$_3$).
$^{13}$C NMR (CDCl$_3$, 100.67 MHz): δ=162.2 (CN), 155.8 (CO), 151.7 (CO), 143.9 (C), 143.5 (C), 133.2 (C), 130.1 (C), 128.7 (CH), 128.4 (CH), 127.0 (CH), 126.2 (CH), 121.4 (C), 120.2 (CH), 58.0 (CH$_2$), 43.5 (NCH$_3$).

Synthesis of Lig$^{13}$H$_2$

A solution of 2-(iodomethyl)-4-tert-butyl-6-(di-tert-butylcarbazole)-phenol (0.43 g, 0.8 mmol) in THF (20 mL) was added dropwise to a solution of 2-adamantyl-4-methyl-6-(((2-(methyl amino)phenyl)imino)methyl)phenol (0.28 g, 0.8 mmol) and triethylamine (3 mL) in THF (20 mL) and stirred for 2 h. The solid that formed was filtered out and the solvent was removed under vacuum. The crude product was purified by flash-chromatography on silica gel 60 with a mixture of petroleum ether:dichloromethane in increasing polarity as eluent yielding the ligand precursor as a brown solid quantitatively.

$^1$H NMR (CDCl$_3$, 500 MHz): δ=8.28 (s, 1H, NCH), 8.08 (d, 1H, J=1.5 Hz, ArH), 7.27-7.26 (m, 2H, ArH), 7.21-7.18 (m, 5H, ArH), 7.06 (d, 1H, J=1.5 Hz, ArH), 6.98 (m, 2H, ArH), 6.87-6.85 (m, 2H, ArH), 6.69 (d, 1H, J=1.3 Hz, ArH), 4.53 (s, 2H, CH$_2$), 2.87 (s, 3H, NCH$_3$), 2.23 (s, 3H, CH$_3$), 2.20 (m, 6H, adamantyl), 1.94 (m, 3H, adamantyl), 1.68 (m, 6H, adamantyl), 1.42 (s, 18H, 2(N-tert-Bu)), 1.77 (m, 6H, adamantyl), 1.27 (m, 9H, Ar-tert-Bu).

Example 1

Synthesis of Lig$^1$ZrBn$_2$

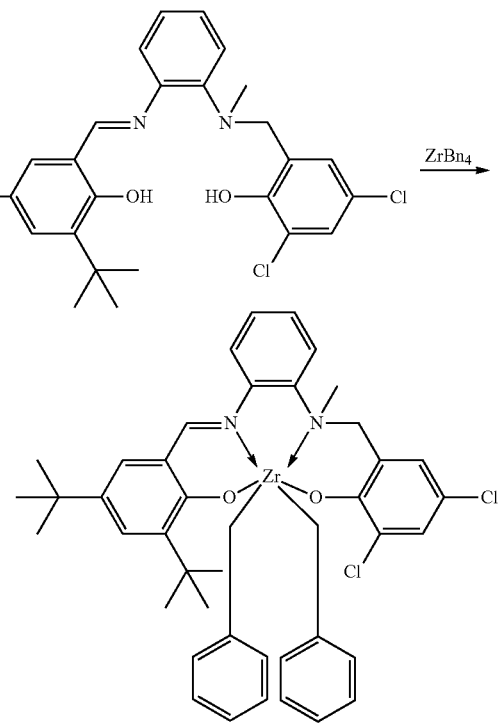

Lig$^1$H$_2$ (36 mg, 0.07 mmol) was dissolved in 1 mL of toluene chilled to −35° C. and the solution was added dropwise to a stirring solution of ZrBn$_4$ (32 mg, 0.07 mmol) in 1 mL of chilled toluene. The reaction mixture was allowed to warm to room temperature and after 1 h the solvent was removed under vacuum, yielding a yellow solid, which was washed with 1 mL of pentane and dried in vacuo.

$^1$H NMR (C$_6$D$_6$, 400 MHz): δ=7.39 (d, 1H, J=1.6 Hz, ArH), 7.22-6.93 (m, 13H, ArH), 6.64-6.63 (m, 2H, ArH), 6.58-6.55 (m, 3H, ArH), 4.74 (d, J=7.8 Hz, 1H), 3.47 (d, J=7.8 Hz, 1H), 3.17 (d, J=14.0 Hz, 1H), 2.81 (d, J=10.2 Hz, 1H), 2.65 (d, J=10.2 Hz, 1H), 2.42 (d, J=14.0 Hz, 1H), 1.76 (s, 9H, (CH$_3$)$_3$), 1.50 (s, 3H, NCH$_3$), 1.09 (s, 9H, (CH$_3$)$_3$).

Example 2

Synthesis of Lig$^2$ZrBn$_2$

Lig$^2$H$_2$ (33 mg, 0.05 mmol) was dissolved in 1 mL of toluene chilled to −35° C. and the solution was added dropwise to a stirring solution of ZrBn$_4$ (25 mg, 0.05 mmol) in 1 mL of chilled toluene. The reaction mixture was allowed to warm to room temperature and after 1 h the solvent was removed under vacuum, yielding an orange solid, which was washed with 1 mL of pentane and dried in vacuo.

$^1$H NMR (C$_6$D$_6$, 400 MHz): δ=7.53 (d, 1H, J=1.8 Hz, ArH), 7.41 (d, 1H, J=2.0 Hz, ArH), 7.25-6.81 (m, 9H, ArH), 6.54-6.43 (m, 8H, ArH), 4.76 (d, J=8.3 Hz, 1H), 3.47 (d, J=8.3 Hz, 1H), 3.08 (d, J=13.7 Hz, 1H), 2.77 (d, J=9.5 Hz, 1H), 2.67 (d, J=9.5 Hz, 1H), 2.50 (d, J=13.7 Hz, 1H), 1.78 (s, 9H, (CH$_3$)$_3$), 1.47 (s, 3H, NCH$_3$), 1.10 (s, 9H, (CH$_3$)$_3$).

Example 4

Synthesis of Lig$^4$ZrBn$_2$

Lig$^4$H$_2$ (38 mg, 0.07 mmol) was dissolved in 1 mL of toluene chilled to −35° C. and the solution was added dropwise to a stirring solution of ZrBn$_4$ (32 mg, 0.07 mmol) in 1 mL of chilled toluene. The reaction mixture was allowed to warm to room temperature and after 1 h the solvent was removed under vacuum, yielding an orange solid, which was washed with 1 mL of pentane and dried in vacuo.

Example 5

Synthesis of Lig$^5$ZrBn$_2$

Lig$^5$H$_2$ (44 mg, 0.07 mmol) was dissolved in 1 mL of toluene chilled to −35° C. and the solution was added dropwise to a stirring solution of ZrBn$_4$ (31 mg, 0.07 mmol) in 1 mL of chilled toluene. The reaction mixture was allowed to warm to room temperature and after 1 h the solvent was removed under vacuum, yielding an orange solid, which was washed with 1 mL of pentane and dried in vacuo.
$^1$H NMR (C$_6$D$_6$, 400 MHz): δ=8.06 (d, 1H, J=1.9 Hz, ArH), 7.96 (s, 1H, NCH), 7.25-6.63 (m, 15H, ArH), 6.48 (d, 1H, J=1.5 Hz, ArH), 6.25 (d, 1H, J=1.5 Hz, ArH), 4.62 (d, J=8.5 Hz, 1H), 3.51 (d, J=10.4 Hz, 1H), 3.45 (d, J=8.5 Hz, 1H), 3.38 (d, J=10.4 Hz, 1H), 3.19 (d, J=11.5 Hz, 1H), 3.03 (d, J=11.5 Hz, 1H), 2.51-2.45 (m, 6H, adamantyl), 2.25 (s, 3H, NCH$_3$), 2.13 (s, 3H, CH$_3$), 2.05-1.99 (m, 7H, adamantyl).

Example 6

Synthesis of Lig$^6$ZrBn$_2$

Lig$^6$H$_2$ (33 mg, 0.05 mmol) was dissolved in 1 mL of toluene chilled to −35° C. and the solution was added dropwise to a stirring solution of ZrBn$_4$ (21 mg, 0.05 mmol) in 1 mL of chilled toluene. The reaction mixture was allowed to warm to room temperature and after 1 h the solvent was removed under vacuum, yielding an orange solid, which was washed with 1 mL of pentane and dried in vacuo.

Example 8

Synthesis of Lig$^4$HfBn$_2$

Lig$^4$H$_2$ (48 mg, 0.09 mmol) was dissolved in 1 mL of toluene chilled to −35° C. and the solution was added dropwise to a stirring solution of HfBn$_4$ (47 mg, 0.09 mmol) in 1 mL of chilled toluene. The reaction mixture was allowed to warm to room temperature and after 1 h the solvent was removed under vacuum, yielding a red solid, which was washed with 1 mL of pentane and dried in vacuo.
$^1$H NMR (C$_6$D$_6$, 400 MHz): δ=8.01 (s, 1H, NCH), 7.32 (d, 1H, J=2.9 Hz, ArH), 7.12-6.94 (m, 14H, ArH), 6.84 (d, 1H, J=2.9 Hz, ArH), 6.67 (d, 1H, J=1.5 Hz, ArH), 6.46 (d, 1H, J=1.5 Hz, ArH), 3.14 (d, J=14.8 Hz, 1H), 3.03 (d, J=9.7 Hz, 1H), 2.96 (d, J=9.7 Hz, 1H), 2.41 (d, J=14.8 Hz, 1H), 2.35- 2.27 (m, 2H, CH), 2.24 (s, 3H, NCH$_3$), 2.17 (s, 3H, CH$_3$), 2.07-2.02 (m, 9H, adamantyl), 1.91-1.83 (m, 6H, adamantyl).

Example 9

Synthesis of Lig$^5$HfBn$_2$

Lig$^5$H$_2$ (25 mg, 0.04 mmol) was dissolved in 1 mL of toluene chilled to −35° C. and the solution was added dropwise to a stirring solution of HfBn$_4$ (21 mg, 0.04 mmol) in 1 mL of chilled toluene. The reaction mixture was allowed to warm to room temperature and after 1 h the solvent was removed under vacuum, yielding a red solid, which was washed with 1 mL of pentane and dried in vacuo.

Example 10

Synthesis of Lig$^6$HfBn$_2$

Lig$^6$H$_2$ (36 mg, 0.05 mmol) was dissolved in 1 mL of toluene chilled to −35° C. and the solution was added dropwise to a stirring solution of HfBn$_4$ (26 mg, 0.05 mmol) in 1 mL of chilled toluene. The reaction mixture was allowed to warm to room temperature and after 1 h the solvent was removed under vacuum, yielding an orange solid, which was washed with 1 mL of pentane and dried in vacuo.

Example 13

Synthesis of Lig$^{13}$HfBn$_2$

Lig$^{13}$H$_2$ (18 mg, 0.02 mmol) was dissolved in 1 mL of toluene chilled to −35° C. and the solution was added dropwise to a stirring solution of HfBn$_4$ (12 mg, 0.02 mmol) in 1 mL of chilled toluene. The reaction mixture was allowed to warm to room temperature and after 1 h the solvent was removed under vacuum, yielding a brown solid, which was washed with 1 mL of pentane and dried in vacuo.

Example 16

Synthesis of Lig$^5$TiCl$_2$

Lig$^5$H$_2$ (39 mg, 0.06 mmol) was dissolved in 1 mL of toluene, chilled to −35° C. and the solution was added dropwise to a stirring solution of TiCl$_4$ (32 mg, 0.07 mmol) in 1 mL of chilled toluene. The reaction mixture was allowed to warm to room temperature and after 1 h the solvent was removed under vacuum, yielding a red solid, which was washed with 1 mL of pentane and dried in vacuo.
$^1$H NMR (C$_6$D$_6$, 400 MHz): δ=7.65 (s, 1H, NCH), 7.25 (d, 1H, J=1.9 Hz, ArH), 7.23 (d, 1H, J=2.3 Hz, ArH), 7.01 (m, 1H, ArH), 6.73 (m, 1H, ArH), 6.64 (m, 2H, ArH), 6.59 (d, 1H, J=1.9 Hz, ArH), 6.41 (d, 1H, J=2.3 Hz, ArH), 4.58 (d, J=13.0 Hz, 1H), 3.45 (s, 3H, NCH$_3$), 2.95 (d, J=13.0 Hz, 1H), 2.46 (m, 6H, adamantyl), 2.13 (s, 3H, CH$_3$), 2.03-1.97 (m, 3H, adamantyl), 1.81-1.78 (m, 4H, adamantyl).

TABLE 1
Exemplary Salalen precursor compounds
Lig¹H₂
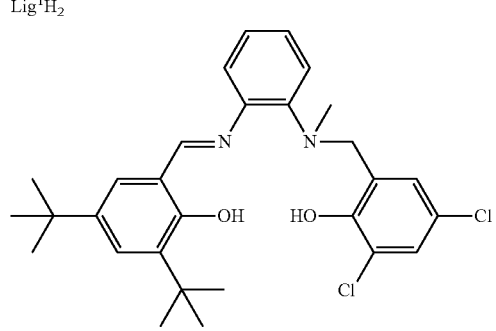
Lig²H₂
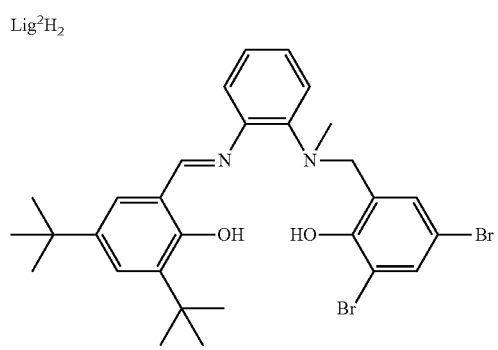
Lig³H₂
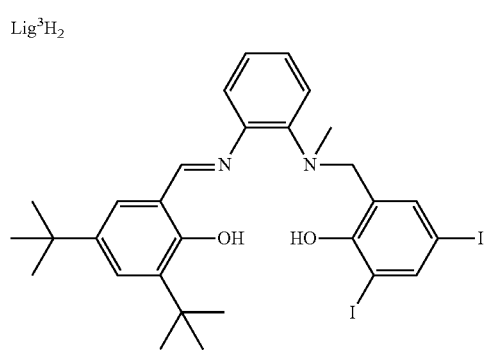
Lig⁴H₂
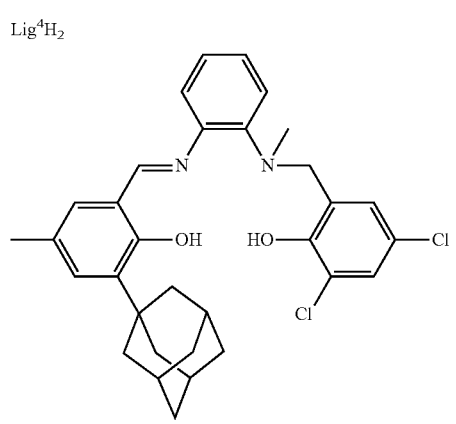
TABLE 1-continued
Exemplary Salalen precursor compounds
Lig⁵H₂
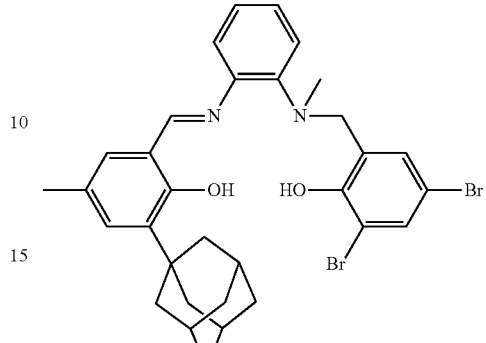
Lig⁶H₂
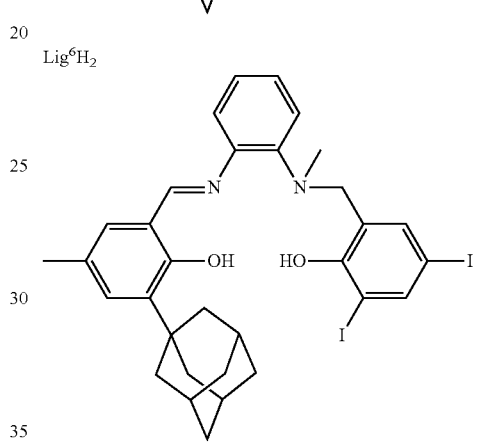
Lig⁷H₂
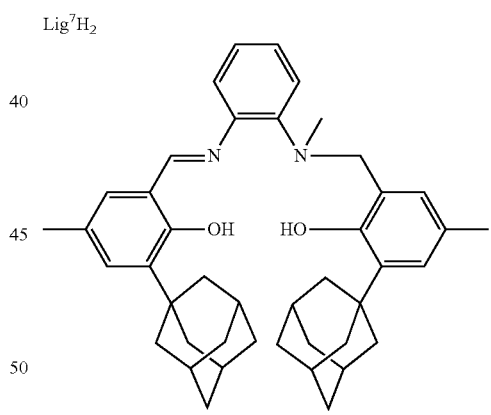
Lig⁸H₂
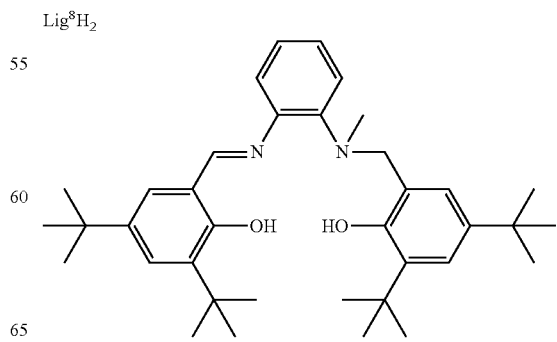

TABLE 1-continued

Exemplary Salalen precursor compounds

Lig⁹H₂

Lig¹⁰H₂

Lig¹¹H₂

Lig¹²H₂

TABLE 1-continued

Exemplary Salalen precursor compounds

Lig¹³H₂

TABLE 2

Exemplary Salalen Catalysts

Example 1 - Lig¹ZrBn₂

Example 2 - Lig²ZrBn₂

TABLE 2-continued
Exemplary Salalen Catalysts
Example 3 - Lig³ZrBn₂
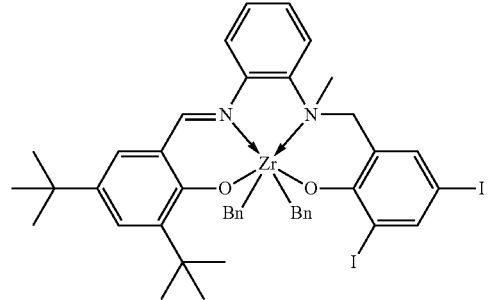
Example 4 Lig⁴ZrBn₂
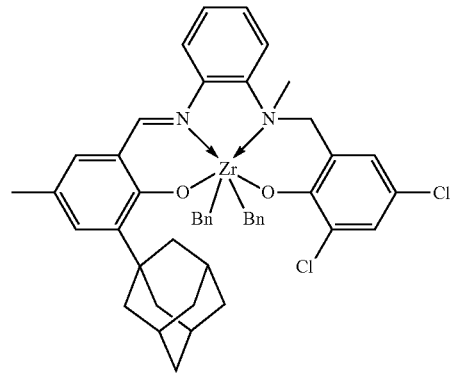
Example 5 Lig⁵ZrBn₂
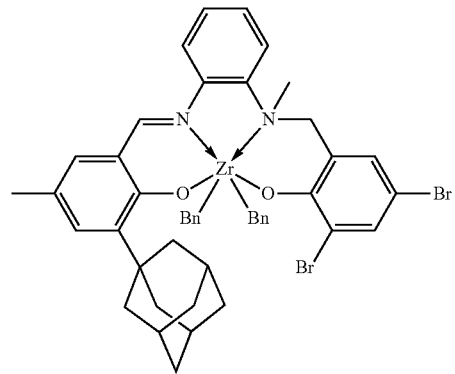
Example 6 Lig⁶ZrBn₂
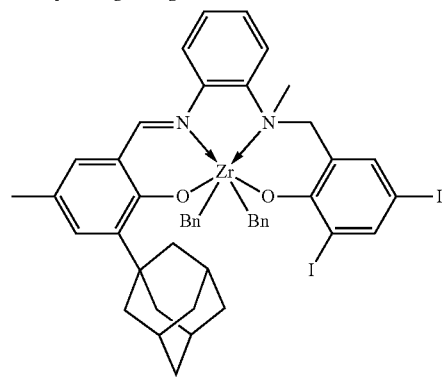
TABLE 2-continued
Exemplary Salalen Catalysts
Example 7 - Lig¹HfBn₂
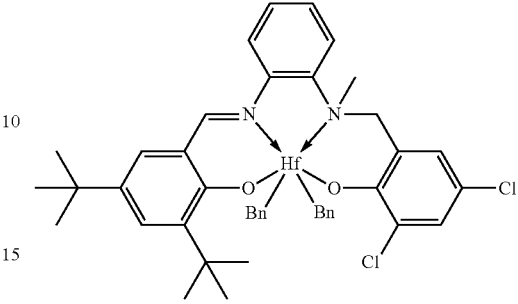
Example 8 - Lig⁴HfBn₂
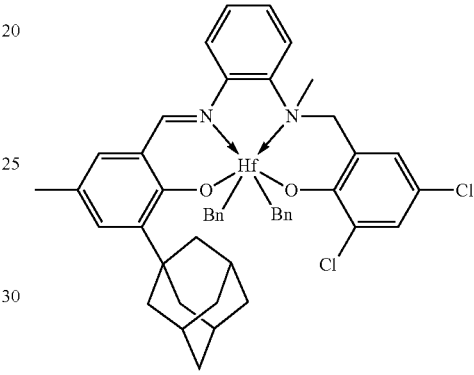
Example 9 - Lig⁵HfBn₂
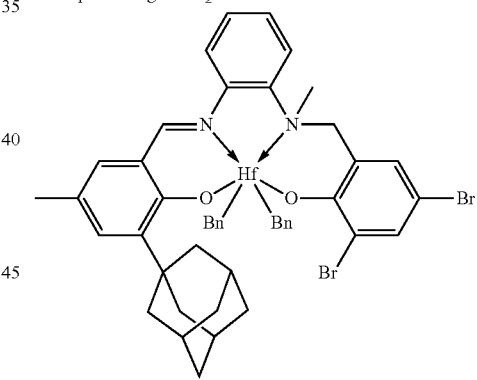
Example 10 - Lig⁶HfBn₂
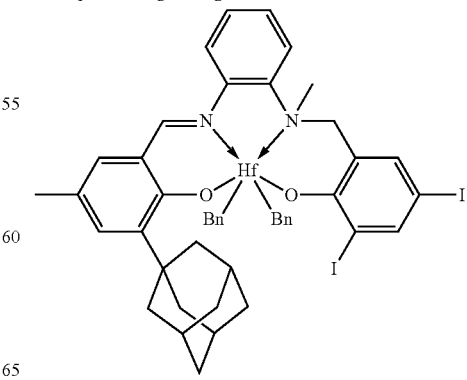

TABLE 2-continued
Exemplary Salalen Catalysts
Example 11 - Lig⁷HfBn₂
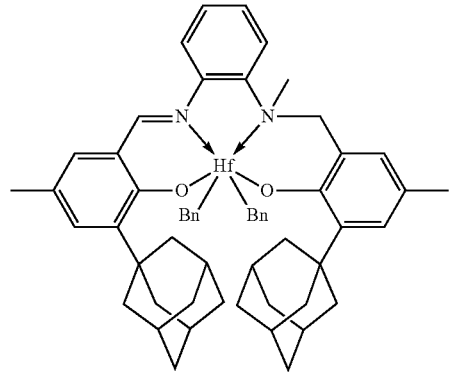
Example 12 - Lig⁸HfBn₂
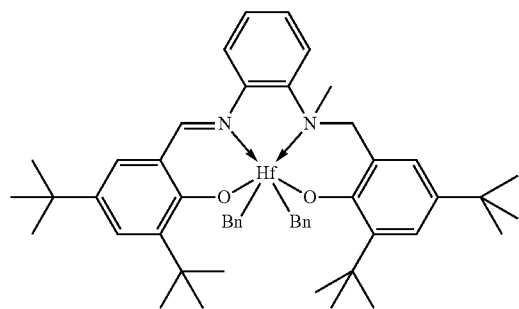
Example 13 - Lig⁹HfBn₂
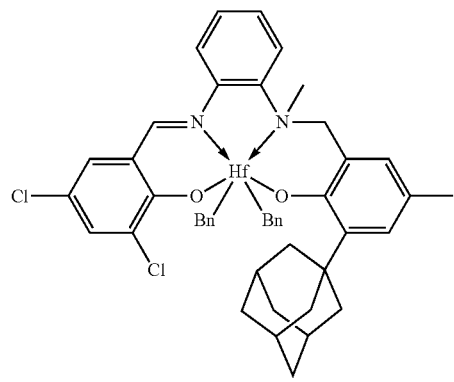
TABLE 2-continued
Exemplary Salalen Catalysts
Example 14 - Lig¹³HfBn₂
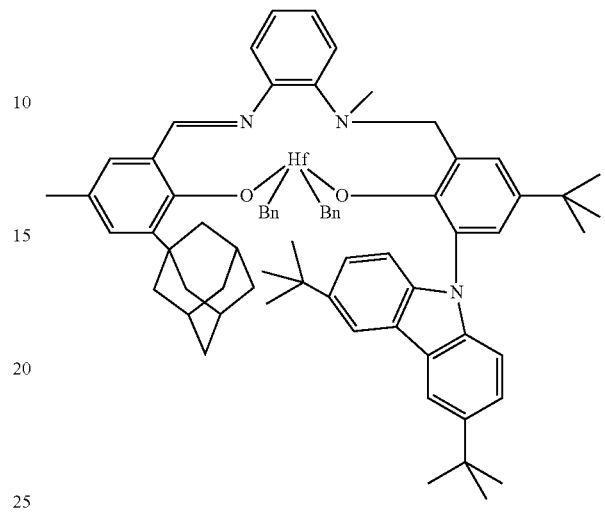
Example 15 - Lig¹TiCl₂
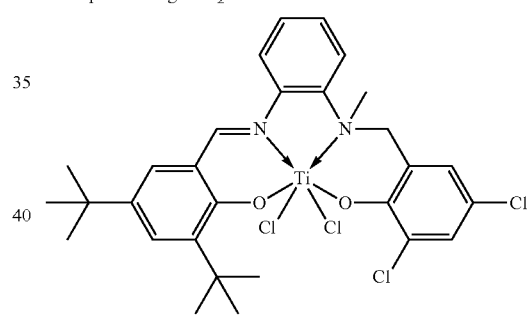
Example 16 - Lig⁵TiCl₂
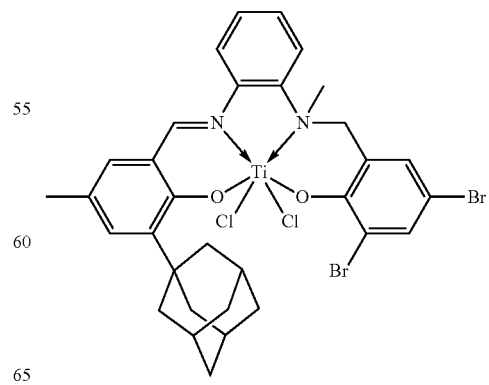

TABLE 2-continued

Exemplary Salalen Catalysts

Example 17 - Lig$^5$TiBn$_2$

Polymerization—Synthesis of Polypropylene

The above catalysts were utilized to produce polypropylene under polymerization conditions. A stainless steel reactor equipped with an inner glass sleeve and a magnetic stir-bar was charged with an exemplary catalyst compound Lig$^{1-12}$ ML$_2$ (M=Ti, Zr, Hf; L=Bn or C$_1$) and 500 equiv of MAO and was cooled with a liquid nitrogen bath. A measured volume of propylene was condensed, the reactor was sealed, and was allowed to warm to R.T. (~25° C.). The polymerization was pursued for 12-14 h. The total weight of the monomer and formed polymer was measured, and the remaining monomer was released. The polymer was treated with an acidified methanol solution (5% HCl solution) and petroleum ether. The insoluble polymers were obtained by filtration and then dried in air. The polymerization results for zirconium, hafnium and titanium catalysts according to embodiments disclosed herein are summarized in Tables 4, 5, and 6 respectively.

TABLE 4

Polymerization of Propylene with Zirconium Catalysts

| Example | Catalyst | Monomer (g) | Polymer (g) | $T_m$ (° C.)$^b$ | $\Delta H$ (J/g)$^b$ | $M_w$ | $M_w/M_n$ | [mmmm] |
|---|---|---|---|---|---|---|---|---|
| 1 | Lig$^1$ZrBn$_2$ | 7.45 | 0.40 | 154 | 11 | 23,000 | 1.94 | |
| 2 | Lig$^2$ZrBn$_2$ | 6.39 | 0.16 | | | | | |
| 3 | Lig$^3$ZrBn$_2$ | 7.29 | 0.28 | | | | | |
| 4 | Lig$^4$ZrBn$_2$ | 6.83 | 1.00 | | | | | 78 |
| 5 | Lig$^5$ZrBn$_2$ | 8.15 | 1.07 | 151.2 | 120 | 32,000 | 3.55 | 95 |
| 6 | Lig$^6$ZrBn$_2$ | 8.16 | 0.14 | | | | | 55 |

$^b$Melting transition and heat of fusion from DSC.

TABLE 5

Polymerization of Propylene with Hafnium Catalysts.

| Example | Catalyst | Monomer (g) | Polymer (g) | $T_m$ (° C.)$^b$ | $\Delta H$ (J/g)$^b$ | $M_w$ | $M_w/M_n$ | [mmmm] |
|---|---|---|---|---|---|---|---|---|
| 7 | Lig$^1$HfBn$_2$ | 7.29 | 0.10 | 143.2 | 17 | | | |
| 8 | Lig$^4$HfBn$_2$ | 6.91 | 0.59 | | | | | 90.7 |
| 9 | Lig$^5$HfBn$_2$ | 7.82 | 0.38 | 147.7 + 153 | 75.7 | 30,000 | 8.9 | 89.4 |
| 10 | Lig$^6$HfBn$_2$ | 6.75 | 0.51 | 159.6 | 98.9 | 35,000 | 6.0 | 98.2 |
| 11 | Lig$^7$HfBn$_2$ | 8.03 | 0.12 | 140 + 146 | 12.4 | | | |
| 12 | Lig$^8$HfBn$_2$ | 8.08 | 0.10 | 144 + 150 | 36.1 | | | |
| 13 | Lig$^9$HfBn$_2$ | 7.34 | 0.20 | 145.7 | 46.0 | | | |

$^b$Melting transition and heat of fusion from DSC.

TABLE 6

Polymerization of Propylene with Titanium Catalysts

| Example | Catalyst | Monomer (g) | Polymer (g) | $T_m$ (° C.)$^b$ | $\Delta H$ (J/g)$^b$ | $M_w$ | $M_w/M_n$ | [mmmm] |
|---|---|---|---|---|---|---|---|---|
| 14 | Lig$^1$TiCl$_2$ | 6.49 | 0.50 | — | — | 408,000 | 3.53 | atac |
| 15 | Lig$^5$TiCl$_2$ | 7.04 | 3.07 | 125 | low | 131,000 | 3.18 | atac |
| 16 | Lig$^5$TiBn$_2$ | 7.53 | 2.90 | | | | | |

$^b$Melting transition and heat of fusion from DSC.

Figure 2:
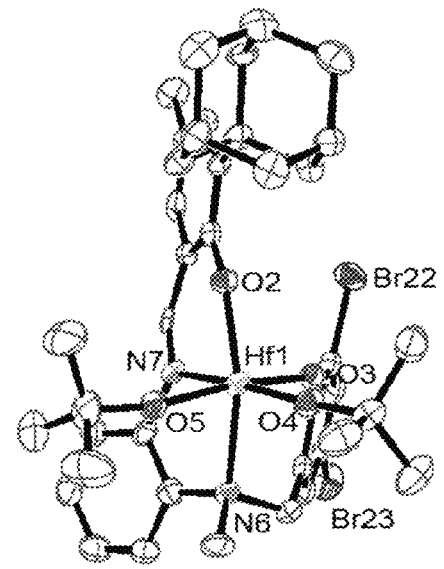
FIG. 2 shows the molecular structure of a catalyst as determined by X-ray diffraction according to another embodiment of the invention.
Figure 3:
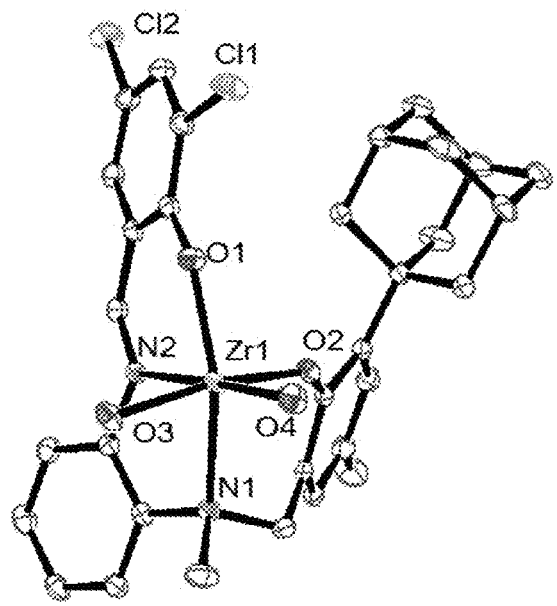
FIG. 3 shows the molecular structure of a catalyst as determined by X-ray diffraction according to another embodiment of the invention.
Figure 4:
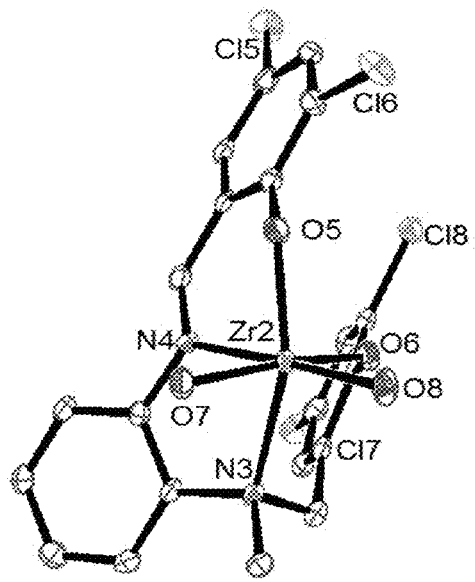
FIG. 4 shows the molecular structure of a catalyst as determined by X-ray diffraction according to another embodiment of the invention.

The molecular structure of Lig⁵Zr(OtBu)₂ as determined by X-ray diffraction is shown in FIG. 1; the molecular structure of Lig⁵Hf(OtBu)₂ is shown in FIG. 2; the molecular structure of Lig⁹Zr(OtBu)₂ is shown in FIG. 3; and the molecular structure of Lig¹²Zr(OtBu)₂ is shown in FIG. 4. In each case, fac-mer wrapping of the Salalen ligand about the Group 4 metal is demonstrated.

As these data show, a very broad variety of phenylene-Salalen catalysts, each having different electronic character and/or bulk (level of steric hindrance) may be prepared according to the instant disclosure. The examples demonstrate the ability to utilize embodiments of the catalyst disclosed herein to control the properties of the resultant polyolefin produced. As the data also show, the catalysts are active in polymerization of propylene in the presence of common co-catalysts and variable degrees of tacticity are obtained by variation of the catalyst substituents. As the data further show, polymers having a very high melting point and a very high isotacticity are obtainable utilizing the inventive catalysts. In particular, a highly isotactic polymer is obtainable utilizing hafnium or zirconium catalysts according to the instant disclosure, which is in contrast to Salalen ligands known in the art which lack the phenylene bridge.

As the data further show, the zirconium and/or hafnium based phenylene bridged Salalen catalysts according to one or more embodiments disclosed herein may be employed to produce a highly isotactic polypropylene polymer. However, the same Salalen ligand system according to one or more embodiments disclosed herein which is useful or which is capable of producing highly isotactic polypropylene when coordinated with hafnium or zirconium may be employed to produce an atactic polypropylene polymer when coordinated with titanium.

As the data show, embodiments of the catalyst comprising a titanium based phenylene bridged Salalen catalyst according to one or more embodiments disclosed herein are useful to produce an atactic polypropylene polymer wherein the catalyst comprises a phenylene Salalen ligand system according to one or more embodiments disclosed herein which is selected based on the usefulness or ability of the phenylene bridged Salalen ligand system according to one or more embodiments disclosed herein to produce a highly isotactic polypropylene polymer when coordinated with hafnium or zirconium.

Polymerization—Synthesis of Poly(1-hexene)

The above catalysts Lig¹ZrBn₂ and Lig⁵ZrBn₂ were utilized to produce poly(1-hexene) under polymerization conditions. A dibenzylzirconium complex of the series Lig¹,⁵ZrBn₂ (10 μmol) was dissolved in 1 mL of 1-hexene and added to a stirred solution of MAO (500 equiv) in 4 mL 1-hexene. The resulting mixture was stirred until the resulting polymer solution had become viscous. The polymer was treated with acidified methanol solution (5% HCl solution) and extracted with chloroform. The organic solvent was removed under vacuum yielding poly(1-hexene) as a yellow gum. The 1-hexene polymerization results for the zirconium catalysts according to embodiments disclosed herein are summarized in Table 7.

TABLE 7

Polymerization of 1-Hexene with Zirconium Catalysts

| Example | Catalyst | Monomer (g) | Polymer (g) | Activity (g mmol⁻¹h⁻¹) | $M_w$ | $M_w/M_n$ | [mmmm] |
|---|---|---|---|---|---|---|---|
| 17 | Lig¹ZrBnl₂ | 3.36 | 1.83 | 10 | | | 66% |
| 18 | Lig⁵ZrBn₂ | 3.36 | 2.30 | 13 | 40,100 | 1.83 | >99% |

As these data show, phenylene-Salalen catalysts in these examples are active in polymerization of 1-hexene in the presence of a common co-catalyst and variable degrees of tacticity are obtained by variation of the catalyst substituents. As the data further show, 1-hexene polymers having a very high isotacticity are obtainable utilizing the inventive catalysts. In particular, a highly isotactic polymer is obtainable utilizing zirconium catalysts according to the instant disclosure. As the data further show, the zirconium based phenylene bridged Salalen catalysts according to one or more embodiments disclosed herein may be employed to produce a highly isotactic poly(1-hexene) polymer at high activity and in very high yield.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments according to the invention, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A catalyst compound represented by the formula:

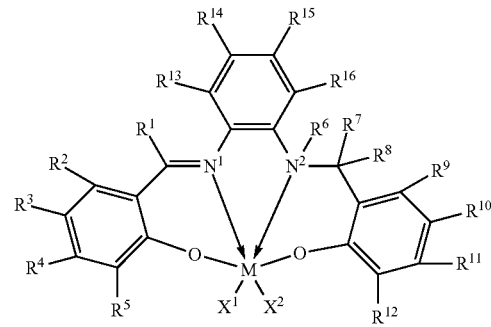

wherein each solid line represents a covalent bond and each arrow represents a bond having a varying degree of covalency and a varying degree of coordination;
wherein M is a Group 4 metal;
$N^1$ and $N^2$ are nitrogen;
O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

2. The catalyst compound of claim 1, wherein M is Hf, Ti, Zr, or a combination thereof.

3. The catalyst compound of claim 1, wherein each of $X^1$ and $X^2$ is, independently, a halogen or a benzyl radical.

4. The catalyst compound of claim 1, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a halogen, or a $C_1$ to $C_{20}$ hydrocarbyl radical.

5. The catalyst compound of claim 1, wherein at least one of $R^3$, $R^5$, $R^{10}$, and $R^{12}$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

6. The catalyst compound of claim 1, at least one of $R^3$, $R^5$, $R^{10}$, and $R^{12}$ is, independently, a $C_1$-$C_{10}$ aliphatic radical or a $C_1$-$C_{10}$ alicyclic radical.

7. The catalyst compound of claim 1, wherein at least one of $R^3$, $R^5$, $R^{10}$, and $R^{12}$ is, independently, a bulky functional group radical having a molecular size greater than or equal to a molecular size of an isopropyl functional group radical.

8. The catalyst compound of claim 1, wherein at least one of $R^3$, $R^5$, $R^{10}$, and $R^{12}$ is, independently, a substituted or unsubstituted aliphatic radical having four carbons or more, a substituted or unsubstituted alicyclic radical having six carbons or more, or a combination thereof.

9. The catalyst compound of claim 1, wherein at least one of $R^3$, $R^5$, $R^{10}$, and $R^{12}$ is, independently, a methyl radical, an adamantyl radical or a tert-butyl radical.

10. The catalyst compound of claim 1, wherein at least one of $R^5$ and $R^{12}$ is, independently, a substituted or unsubstituted carbazolyl radical.

11. The catalyst compound of claim 1, wherein each of $R^3$ and $R^5$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and wherein each of $R^{10}$ and $R^{12}$ is, independently, a $C_1$-$C_{10}$ aliphatic radical or a $C_1$-$C_{10}$ alicyclic radical; or
wherein each of $R^3$ and $R^5$ is, independently, a $C_1$-$C_{10}$ aliphatic radical or a $C_1$-$C_{10}$ alicyclic radical, and wherein each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

12. The catalyst compound of claim 1, wherein each of $R^3$ and $R^5$ is, independently, an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical, and wherein each of $R^{10}$ and $R^{12}$ is, independently, a bulky functional group radical having a molecular size greater than or equal to a molecular size of an isopropyl functional group radical; or
wherein each of $R^3$ and $R^5$ is, independently, a bulky functional group radical having a molecular size greater than or equal to a molecular size of an isopropyl functional group radical, and wherein each of $R^{10}$ and $R^{12}$ is, independently an electron withdrawing functional group radical comprising —$NO_2$, —$CF_3$, —$CCl_3$, —$CBr_3$, —$CI_3$, —CN, —$SO_3H$, —COOH, —CHO, —F, —Cl, —Br, —I, —$COOR^\alpha$, —$COR^\alpha$, —$NR^\alpha_3{}^+$, or a combination thereof, wherein each $R^\alpha$ is independently hydrogen or a $C_1$-$C_{20}$ alkyl radical.

13. The catalyst compound of claim 1, wherein $R^2$ is identical in composition to $R^9$, $R^3$ is identical in composition to $R^{10}$, $R^4$ is identical in composition to $R^{11}$, $R^5$ is identical in composition to $R^{12}$, or a combination thereof.

14. The catalyst compound of claim 1, wherein $R^2$ is different in composition than $R^9$, $R^3$ is different in composition than $R^{10}$, $R^4$ is different in composition than $R^{11}$, $R^5$ is different in composition than $R^{12}$, or a combination thereof.

15. The catalyst compound of claim 1, wherein M is Ti, Zr, or Hf; each of $X^1$ and $X^2$ is independently halogen or benzyl; each of $R^1$, $R^2$, $R^4$, $R^7$, $R^8$, $R^9$, $R^{11}$, $R^{13}$, $R^{14}$, $R^{15}$, and $R^{16}$ is hydrogen, and wherein: i) each of $R^3$ and $R^5$ is tert-butyl, $R^6$ is methyl, and each of $R^{10}$ and $R^{12}$ is independently F, Cl, Br, or I; or ii) each of $R^3$ and $R^6$ is methyl, $R^5$ is adamantyl, and each of $R^{10}$ and $R^{12}$ is independently F, Cl, Br, or I; or iii) each of $R^3$, $R^6$, and $R^{10}$ is methyl, and each of $R^5$ and $R^{10}$ is adamantyl; or iv) each of $R^3$, $R^5$, $R^{10}$ and $R^{12}$ is tert-butyl, and $R^6$ is methyl; or v) each of $R^3$ and $R^5$ is independently F, Cl, Br, or I, each of $R^6$ and $R^{10}$ is methyl, and $R^{12}$ is adamantyl; or vi) each of $R^3$, $R^5$, $R^{10}$, and $R^{12}$ is independently F, $C_1$, Br, or I, and $R^6$ is methyl; or vii) each of $R^3$ and $R^6$ is methyl, $R^5$ is adamantyl, $R^{10}$ is tert-butyl, and $R^{12}$ is 4,4'-di-tert-butyl carbazolyl.

16. A catalyst system comprising:
an activator and a catalyst compound represented by the formula:

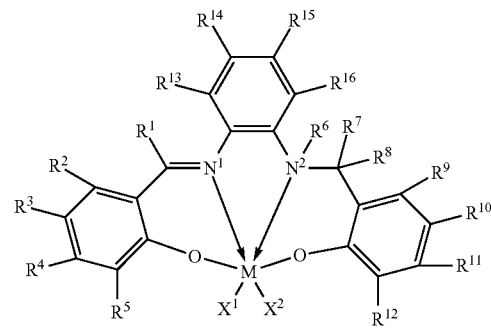

wherein each solid line represents a covalent bond and each arrow represents a bond having a varying degree of covalency and a varying degree of coordination;
wherein M is a Group 4 metal;
$N^1$ and $N^2$ are nitrogen and O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

17. The catalyst system of claim 16, wherein: M is Ti, Zr, or Hf; each of $X^1$ and $X^2$ is independently halogen or benzyl, each of $R^1$, $R^2$, $R^4$, $R^7$, $R^8$, $R^9$, $R^{11}$, $R^{13}$, $R^{14}$, $R^{15}$, and $R^{16}$ is hydrogen, and wherein: i) each of $R^3$ and $R^5$ is tert-butyl, $R^6$ is methyl, and each of $R^{10}$ and $R^{12}$ is independently F, Cl, Br, or I; or ii) each of $R^3$ and $R^6$ is methyl, $R^5$ is adamantyl, and each of $R^{10}$ and $R^{12}$ is independently F, Cl, Br, or I; or iii) each of $R^3$, $R^6$, and $R^{10}$ is methyl, and each of $R^5$ and $R^{10}$ is adamantyl; or iv) each of $R^3$, $R^5$, $R^{10}$ and $R^{12}$ is tert-butyl, and $R^6$ is methyl; or v) each of $R^3$ and $R^5$ is independently F, Cl, Br, or I, each of $R^6$ and $R^{10}$ is methyl, and $R^{12}$ is adamantyl; or vi) each of $R^3$, $R^5$, $R^{10}$, and $R^{12}$ is independently F, $C_1$, Br, or I, and $R^6$ is methyl; or vii) each of $R^3$ and $R^6$ is methyl, $R^5$ is adamantyl, $R^{10}$ is tert-butyl, and $R^{12}$ is 4,4'-di-tert-butyl carbazolyl.

18. The catalyst system of claim 16, wherein the activator is an alumoxane.

19. The catalyst system of claim 16, wherein the activator is a non-coordinating anion activator.

20. The catalyst system of claim 16, wherein the activator is a non-coordinating anion activator selected from the group consisting of: N,N-dimethylanilinium tetrakis(perfluorophenyl)borate, methyldioctadecylammonium tetrakis(perfluorophenyl)borate, methyldi($C_{14-20}$ alkyl)ammonium tetrakis (perfluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, and [4-t-butyl-PhNMe$_2$H][($C_6F_3$($C_6F_5$)$_2$)$_4$B], where Ph is phenyl, and Me is methyl.

21. A process comprising:
contacting one or more olefins with a catalyst system at a temperature, a pressure, and for a period of time sufficient to produce a polyolefin;
the catalyst system comprising an activator and a catalyst compound represented by the formula:

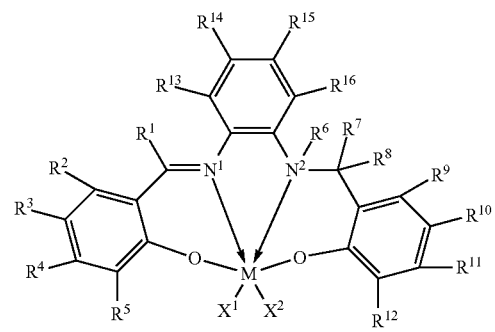

wherein each solid line represents a covalent bond and each arrow represents a bond having a varying degree of covalency and a varying degree of coordination;
wherein M is a Group 4 metal;
$N^1$ and $N^2$ are nitrogen and O is oxygen;
each of $X^1$ and $X^2$ is, independently, a univalent $C_1$ to $C_{20}$ hydrocarbyl radical, a functional group comprising elements from Groups 13 to 17 of the periodic table of the elements, or $X^1$ and $X^2$ join together to form a $C_4$ to $C_{62}$ cyclic or polycyclic ring structure;
wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is independently, hydrogen, a $C_1$-$C_{40}$ hydrocarbyl radical, a functional group comprising elements from Groups 13 to 17 of the periodic table of the elements, two or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ independently join together to form a $C_4$ to $C_{62}$ cyclic or polycyclic ring structure, or a combination thereof.

22. The process of claim 21, wherein the catalyst compound is disposed on a support.

23. The process of claim 21, wherein the one or more olefins includes propylene, wherein the polyolefin is a propylene polymer having a melting point of greater than 145° C. determined by differential scanning calorimetry, and wherein the polyolefin comprises a meso-pentad [mmmm] content of greater than or equal to about 89%, as determined by $^{13}$C NMR.

24. The process of claim 23, wherein: M is Hf; $R^3$ is a methyl radical; $R^5$ is an adamantyl radical; and $R^{10}$ and $R^{12}$ are each independently a bromine radical or an iodine radical.

25. The process of claim 24, wherein the one or more olefins includes propylene, wherein the polyolefin is a propylene polymer having a melting point of greater than 150° C. determined by differential scanning calorimetry, and wherein the polyolefin comprises a meso-pentad [mmmm] content of greater than or equal to about 95%, as determined by $^{13}$C NMR.

26. The process of claim 25, wherein: M is Zr; $R^3$ is a methyl radical; $R^5$ is an adamantyl radical; and $R^{10}$ and $R^{12}$ are each independently a bromine radical.

27. The process of claim 21, wherein the one or more olefins includes propylene; wherein the polyolefin is an atactic propylene polymer, and wherein the polyolefin comprises a weight average molecular weight (Mw) greater than 100,000 g/mol and a molecular weight distribution (Mw/Mn) of less than 5, wherein Mw and Mn are each determined by gel permeation chromatography.

28. The process of claim 27, wherein: M is Ti; $R^3$ is a $C_1$-$C_{10}$ aliphatic radical; $R^5$ is an aliphatic or alicyclic bulky functional group radical having a molecular size greater than or equal to a molecular size of an isopropyl functional group radical; and $R^{10}$ and $R^{12}$ are each independently a halogen radical.

* * * * *